US007868000B2

United States Patent
Zhu et al.

(10) Patent No.: US 7,868,000 B2
(45) Date of Patent: Jan. 11, 2011

(54) ASPARTYL PROTEASE INHIBITORS

(75) Inventors: Zhaoning Zhu, Plainsboro, NJ (US); Brian McKittrick, New Vernon, NJ (US); Andrew Stamford, Chatham Township, NJ (US); William J. Greenlee, Teaneck, NJ (US); Xiaoxiang Liu, River Vale, NJ (US); Mihirbaran Mandal, Scotch Plains, NJ (US); Johannes H. Voigt, Cranford, NJ (US); Corey O. Strickland, Martinsville, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 11/451,541

(22) Filed: Jun. 12, 2006

(65) Prior Publication Data

US 2007/0060575 A1 Mar. 15, 2007

Related U.S. Application Data

(60) Provisional application No. 60/690,537, filed on Jun. 14, 2005.

(51) Int. Cl.
*A61K 31/55* (2006.01)
*A61K 31/53* (2006.01)
*A61K 31/519* (2006.01)
*A01N 43/62* (2006.01)
*A01N 43/64* (2006.01)
*A01N 43/90* (2006.01)
*C07D 253/08* (2006.01)
*C07D 487/00* (2006.01)
*C07D 491/00* (2006.01)
*C07D 513/00* (2006.01)
*C07D 515/00* (2006.01)

(52) U.S. Cl. .................... 514/221; 514/242; 514/265.1; 544/183; 544/280; 540/568

(58) Field of Classification Search ........................ None
See application file for complete search history.

(56) References Cited

U.S. PATENT DOCUMENTS

| | | | |
|---|---|---|---|
| 5,610,294 A | 3/1997 | Lam et al. | |
| 2005/0171112 A1 | 8/2005 | Schulz et al. | |
| 2005/0282825 A1 | 12/2005 | Malamas et al. | |
| 2005/0282826 A1 | 12/2005 | Malamas et al. | |
| 2006/0111370 A1 | 5/2006 | Zhu et al. | |
| 2007/0004730 A1 | 1/2007 | Zhou et al. | |
| 2007/0004786 A1 | 1/2007 | Malamas et al. | |
| 2007/0027199 A1 | 2/2007 | Malamas et al. | |
| 2007/0072852 A1 | 3/2007 | Zhu et al. | |
| 2007/0072925 A1 | 3/2007 | Malamas et al. | |
| 2007/0099875 A1 | 5/2007 | Zhu et al. | |
| 2007/0203116 A1 | 8/2007 | Quagliato et al. | |
| 2007/0232642 A1 | 10/2007 | Baxter et al. | |
| 2007/0259898 A1 | 11/2007 | Baxter et al. | |
| 2007/0287692 A1 | 12/2007 | Wu et al. | |
| 2007/0299087 A1 | 12/2007 | Berg et al. | |
| 2008/0051420 A1 | 2/2008 | Berg et al. | |
| 2008/0058349 A1 | 3/2008 | Berg et al. | |
| 2008/0161269 A1 | 7/2008 | Berg et al. | |
| 2008/0200445 A1 | 8/2008 | Zhu et al. | |
| 2008/0214577 A1 | 9/2008 | Berg et al. | |
| 2008/0287460 A1 | 11/2008 | Burrows et al. | |
| 2008/0287462 A1 | 11/2008 | Chessari et al. | |
| 2009/0023762 A1 | 1/2009 | Berg et al. | |
| 2009/0062282 A1 | 3/2009 | Albert et al. | |
| 2009/0209529 A1 | 8/2009 | Andreini et al. | |

FOREIGN PATENT DOCUMENTS

| | | |
|---|---|---|
| EP | 1942105 | 7/2006 |
| WO | WO90/04917 | 5/1990 |
| WO | WO93/04047 | 3/1993 |
| WO | WO 93/04047 | 3/1993 |
| WO | WO 96/09307 | 3/1996 |
| WO | WO01/07440 | 2/2001 |
| WO | WO02/12243 | 2/2002 |
| WO | WO 02/074719 | 9/2002 |
| WO | WO2005/014540 | 2/2005 |

(Continued)

OTHER PUBLICATIONS

Vippagunta et al. Advanced Drug Delivery Reviews 48 (2001) 3-26.*

(Continued)

*Primary Examiner*—James O Wilson
*Assistant Examiner*—Jeffrey H Murray
(74) *Attorney, Agent, or Firm*—Keith D. MacMillan; William Y. Lee; Gerard M. Devlin

(57) ABSTRACT

Disclosed are compounds of the formula I or a stereoisomer, tautomer, or pharmaceutically acceptable salt or solvate thereof, wherein j, k, U, W, R, $R^1$, $R^2$, $R^3$, $R^4$, $R^6$, $R^7$ and $R^{7a}$ are as described above in the specification.

Also disclosed is the method of inhibiting aspartyl protease, and in particular, the methods of treating cardiovascular diseases, cognitive and neurodegenerative diseases. Also disclosed are methods of treating cognitive or neurodegenerative diseases using the compounds of formula I in combination with a cholinesterase inhibitor or a muscarinic $m_1$ agonist or $m_2$ antagonist.

45 Claims, No Drawings

FOREIGN PATENT DOCUMENTS

| | | |
|---|---|---|
| WO | WO2005/016876 | 2/2005 |
| WO | WO 2005/058311 | 6/2005 |
| WO | WO2005/108391 | 11/2005 |
| WO | WO 2006/009653 | 1/2006 |
| WO | WO2006/009655 | 1/2006 |
| WO | WO2006/014762 | 2/2006 |
| WO | WO2006/014944 | 2/2006 |
| WO | WO 2006/017836 A2 | 2/2006 |
| WO | WO 2006/017844 A1 | 2/2006 |
| WO | WO 2006/024932 A1 | 3/2006 |
| WO | WO 2006/041404 | 4/2006 |
| WO | WO2006/041405 | 4/2006 |
| WO | WO 2006/044492 | 4/2006 |
| WO | WO2006/076284 | 7/2006 |
| WO | WO 2006/076284 A2 | 7/2006 |
| WO | WO2006/138192 | 12/2006 |
| WO | WO2006/138195 | 12/2006 |
| WO | WO2006/138217 | 12/2006 |
| WO | WO2006/138230 | 12/2006 |
| WO | WO2006/138264 | 12/2006 |
| WO | WO2006/138265 | 12/2006 |
| WO | WO2006/138266 | 12/2006 |
| WO | WO 2007/005366 | 1/2007 |
| WO | WO 2007/005404 | 1/2007 |
| WO | WO 2007/016012 | 2/2007 |
| WO | WO 2007/038271 | 4/2007 |
| WO | WO 2007/049532 A1 | 5/2007 |
| WO | WO 2007/050612 A1 | 5/2007 |
| WO | WO2007/050721 | 5/2007 |
| WO | WO2007/053506 | 5/2007 |
| WO | WO2007/058580 | 5/2007 |
| WO | WO2007/058582 | 5/2007 |
| WO | WO2007/058583 | 5/2007 |
| WO | WO2007/058601 | 5/2007 |
| WO | WO2007/058602 | 5/2007 |
| WO | WO2007/073284 | 6/2007 |
| WO | WO2007/078813 | 7/2007 |
| WO | WO 2007/092839 A2 | 8/2007 |
| WO | WO 2007/092846 A2 | 8/2007 |
| WO | WO 2007/092854 A2 | 8/2007 |
| WO | WO2007/100536 | 9/2007 |
| WO | WO 2007/114771 | 10/2007 |
| WO | WO 2007/114771 A1 | 10/2007 |
| WO | WO 2007/145568 | 12/2007 |
| WO | WO 2007/145569 | 12/2007 |
| WO | WO 2007/145570 | 12/2007 |
| WO | WO 2007/145571 | 12/2007 |
| WO | WO2007/146225 | 12/2007 |
| WO | WO 2007/149033 | 12/2007 |
| WO | WO 2007/149033 A1 | 12/2007 |
| WO | WO2008/022024 | 2/2008 |
| WO | WO 2008/022024 A2 | 2/2008 |
| WO | WO2008/063114 | 5/2008 |
| WO | WO2008/073365 * | 6/2008 |
| WO | WO2008/073370 * | 6/2008 |
| WO | WO2008/076043 | 6/2008 |
| WO | WO2008/076044 | 6/2008 |
| WO | WO2008/076045 | 6/2008 |
| WO | WO2008/076046 | 6/2008 |
| WO | WO2008/103351 | 8/2008 |
| WO | WO 2008/103351 A2 | 8/2008 |
| WO | WO2008/115552 | 9/2008 |
| WO | WO2008/118379 | 10/2008 |
| WO | WO 2008/133273 A1 | 11/2008 |
| WO | WO 2008/133274 A1 | 11/2008 |
| WO | WO 2009/005470 A1 | 1/2009 |
| WO | WO 2009/005471 A1 | 1/2009 |
| WO | WO 2009/022961 A1 | 2/2009 |
| WO | WO 2009/007300 A2 | 7/2009 |
| WO | WO 2009/091016 A1 | 7/2009 |
| WO | WO 2009/092566 A1 | 7/2009 |
| WO | WO 2009/097278 A1 | 8/2009 |
| WO | WO 2009/097401 A1 | 8/2009 |
| WO | WO 2009/108560 A1 | 9/2009 |
| WO | WO 2009/131974 A1 | 10/2009 |
| WO | WO 2009/131975 A1 | 10/2009 |
| WO | WO 2009/134617 A1 | 11/2009 |
| WO | WO 2009/151098 A1 | 12/2009 |
| WO | WO 2010/013302 A1 | 2/2010 |
| WO | WO 2010/013794 A1 | 2/2010 |
| WO | WO 2010/038686 A1 | 4/2010 |
| WO | WO 2010/047372 A1 | 4/2010 |
| WO | WO 2010/056194 A1 | 5/2010 |
| WO | WO 2010/059953 A1 | 5/2010 |

OTHER PUBLICATIONS

Borisy, et. al., Proceedings of the National Academy of Sciences of the United States of America, 2003, 100(13) 7977-7982.*

Barton, H.J., et al., "On the Structure of some Substituted 4,6-Pyrimidinediones", Polish J. Chem., (1995), pp. 235-245, vol. 69.

Garratt, Peter, J., et al., "A Novel Synthesis of Dihydropyrimidines", J. Chem. Soc., Chem. Commun., (1987), pp. 568-569.

Keana, John, F.W. et al., "Diels-Alder Reactions Involving Heterocyclic Dienophiles. Synthesis of Substituted Hydroquinazolines and 1,3-Diazaspiro[4.5] Decadienes", J. Org. Chem., (1976), pp. 2124-2129, vol. 41, No. 12.

Keana, John, F.W., et al., "Synthetic Intermediates Potentially Useful for the Synthesis of Tetrodotoxin and Derivatives", Journal of Organic Chemistry, (1969), pp. 3705-3707, vol. 34, No. 11.

Kwon, Chul-Hoon, et al., "Facile Synthesis of Substituted 2-Iminohydantoins", Synthetic Communications, (1987), pp. 1677-1682, vol. 17, No. 14.

Na, Byoung-Kuk, et al., "Aspartic Protease of Plasmodium Vivax are Highly Conserved in Wild Isolates", The Korean Journal of Parasitology, (2004), pp. 61-66, vol. 42, No. 2.

Weber, W. et al., "First Synthesis of the Main Metabolite of Secobarbital", Pharmazie, (1998), pp. 771-775, vol. 53, No. 11.

PCT International Search Report dated Nov. 14, 2006 for corresponding PCT Application No. PCT/US2006/022918, 5 pages.

Keana et al., "Diels-Alder Reactions Involving Heterocyclic Dienophiles. Synthesis of Substituted Hydroquinazolines and 1,3,-Diazaspiro[4.5] decadinenes", J. Org. Chem., 1976, pp. 2124-2129, vol. 41, No. 12.

Keana et al, "Synthetic Intermediates Potentially Useful for the Synthese of Tetrodotoxin and Derivatives", The Journal of Organic Chemistry, 1969, pp. 3705-3707, vol. 34, No. 11.

Baxter, Ellen, et. al.; Journal of Medicinal Chemistry; vol. 50, No. 18, Sept. 6, 2007; "2-Amino3, 4-dihydroquinazolines as Inhibitors of BACE-1 . . . ; "; Published on Web on Aug. 8, 2007.

Buteau, Kristen C.; "Deuterated Drugs: Unexpectedly Nonobvious?", 10 J. High Tech L. 22 (2009).

Zhu, Zhaoning, et. al.; Journal of Medicinal Chemistry, vol. 53, No. 3, " Discovery of Cyclic Acylguanidines as Highly Potent and Selective . . . "; Sep. 21, 2009, pp. 951-965.

Nowak, Paweit, et. al.; Biiorganic and Medicinal Chemistry Letters; 20 (2010); "Discovery and initial optimization of 5, 5'-disubstituted aminohydantoins as potent . . . "; pp. 632-635.

Zhou, Ping, et. al.; Biiorganic and Medicinal Chemistry Letters; 20 (2010); "Pyridinyl aminohydantoins as small molecule BACE1 inhibitors"; pp. 2326-2329.

Malamas, Michael S.; et. al.; Biiorganic and Medicinal Chemistry Letters; 18 (2010); "Di-substituted pyridinyl aminohydantoins as potent and highly selective human . . . "; pp. 630-639.

Zhou, Ping; et. al.; "Pyridinylaminohydantoins as small molecule BACE-1 Inhibitors: Explorations of the S3 pocket", AN 2007:883652; 234TH ACS Conference Meeting Abstract; 2010 ACS on SciFinder.

Baxter, Ellen, et. al.; "BACE (Beta-Amyloid site Cleaving Enzyme, β-Secretase) Inhibitors for the treatment of Alzheimer's disease"; AN 2007:883605; 234TH ACS Conference Meeting Abstract; 2010 ACS on SciFinder.

Albert, Jeffrey S.; et. al.; "Fragment based lead generation approaches for inhibitors of beta-secretase: Development of a novel series of isocytosine-based inhibitors"; AN 2007:295744.

Yan, Yinfa; et. al.; Piperidinyl-2-aminohydantoin derivatives for the inhibition of beta-secretase; AN 2007:295742; 233rd ACS National Meeting Abstract; 2010 ACS on SciFinder.

Erdel, Jim; et. al.; "Carbocylic substituted aminohydatoins as BACE-1 Inhibitors"; AN 2007: 295741; 233rd ACS National Meeting Abstract; 2010 ACS on SciFinder.

Nowak, Pawei; et. al.; "Hit-to-lead optimization of aminohydantoins as b-Secretase Inhibitors"; AN 2007:295740; 233rd ACS National Meeting Abstract; 2010 ACS on SciFinder.

Malamas, Michael S.; et. al.; "Aminohydantoins as highly potent, selective and orally active BACE 1 Inhibitors", AN 2007-295667; 233RD Conference Meeting Abstract; 2010 ACS on SciFinder.

Malamas, Michael S.; et. al.; "Thienyl aminohydantoins as potent BACE1 Inhibitors", AN 2008:953770; 236th Conference Meeting Abstract; 2010 ACS on SciFinder.

Malamas, Michael S.; et. al.; "Pyrazinyl aminohydantoins as potent BACE1 Inhibitors", AN 2008:953771; 236th Conference Meeting Abstract; 2010 ACS on SciFinder.

Malamas, Michael S.; et. al.;"Pyrrolyl2-aminopyridines as potent BACE1 Inhibitors", 238th Conference Meeting Abstract; 2010 ACS on SciFinder.

Zhou, Ping; et. al.; "Substituted-pyrrole 2-amino-3.5-dihydro-4H-imidazol-4-ones as highly potent BACE1 Inhibitors: Optimization of the S3 pocket"; 235th Conference Meeting Abstract; 2010 ACS on SciFinder.

Yan, Yinfa; et. al.; "Syntheses and biological properties of carbocylic substituted aminohydantoin derivatives", AN 2008:389811; 235th Conference Meeting Abstract; 2010 ACS on SciFinder.

Quagliato, Dominick; et. al.; "Rigid analogs of 4, 4-diaryl-iminohydantoins as potent inhibitors of Beta-secretase", AN 2008:389810; 235th Conference Meeting Abstract; 2010 ACS on SciFinder.

Solvibile, William R.; et. al.; "2-Substituted-pyrrole 2 —amino-3, 5-dihydro-4H-imidazol-4-ones: Highly potent and selective BACE1 Inhibitors", AN 2008:389809; 235th Conference Meeting Abstract; 2010 ACS on SciFinder.

Erdel, Jim; et. al.; "N-Alkyl substituted-pyrrole 2-amino-3, 5-dihydro-4H-imidazol-4-ones as potent, and selective Bace 1 Inhibitors", AN 2008:389808; 235th Conference Meeting Abstract; 2010 ACS on SciFinder.

Fobare, William F. et. al.; "Substituted-pyrrole 2-amino-3, 5-dihydro-4h-imidazol-4-ones as highly potent and selective BACE1 Inhibitors", AN 2008:389736; 235th Conference Meeting Abstract; 2010 ACS on SciFinder.

Fan, Kristi Yi; et. al.; "Structure-based lead optimization of small molecule β-secretase(BACE1) Inhibitors", AN 2008:387238; 235th Conference Meeting Abstract; 2010 ACS on SciFinder.

Zhu, Zhaoning, et. al.; "Discovery of cyclic-aciguanidines as potent and selective BACE1 Inhibitors", AN 2009: 984464; 238th Conference Meeting Abstract; 2010 ACS on SciFinder.

Cuming, Jared, et. al.; Optimization of the iminohydantoin series of BACE1 Inhibitors. Part 4: Explorations of the F' subsite in the C5-aryl series; AN 2009:984451; 2010 ACS on SciFinder.

Smith, Elizabeth, et. al.; "Optimization of the iminohydantoin series of BACE1 Inhibitors. Part 5: Exploration of the S1' and S2-S3 binding sites"; AN 2009:984450; 238th Conference Meeting Abstract; 2010 ACS on SciFinder.

Mazzola, Robert, D.; et. al.; Design and synthesis of novel iminohydatoin β-secretase (BACE) Inhibitors. Part 3: Discovery and Exploration of the "A-site"; AN 2009:984449; 238th Conference Meeting Abstract; 2010 ACS on SciFinder.

Mazzola, Robert, D.; et. al.; "Novel iminopyrimidinone β-secretase (BACE)Inhibitors: Part 3: C5 Substititution"; AN 2010:345058; 239th Conference Meeting Abstract; 2010 ACS on SciFinder.

Caldwell, John, et. al.; Design and synthesis of novel iminohydatoin β-secretase (BACE) Inhibitors. Part 2: the S1 to S3 approach; AN 2009:984447; 238th Conference Meeting Abstract; 2010 ACS on SciFinder.

Sun Zhong-Yue, et. al.; "2- iminohydatoin as potential BACE1 Inhibitors"; AN 2009:984446; 238th Conference Meeting Abstract; 2010 ACS on SciFinder.

Efremov, Ivan V., et. al.; "Identificaiton of spirocycli pyrrolidines as novel BACE Inhibitors"; AN2010:345057; 239th Conference Meeting Abstract; 2010 ACS on SciFinder.

Iserloh, Ulrich; et. al.; Novel iminopyrimidinone β-secretase (BACE)Inhibitors: Part 2. P1-azoles AN 2010:345056; 239th Conference Meeting Abstract; 2010 ACS on SciFinder.

Robichaud, Albert J.; et. al.; Identification of selective BACE1 inhibitors as potential disease modifying treatments for Alzheimer's disease: AN 2010:344829; 239th Conference Meeting Abstract; 2010 ACS on SciFinder.

Brodney, Michael a.; et. al.; "Beta-secretase inhibitors for the treatment of Alzheimer's disease", AN2010:344828; 239th Conference Meeting Abstract; 2010 ACS on SciFinder.

Stamford, Andrew.W.; et. al.; "Discovery of small molecule, orally active and brain penetrant BACE 1 Inhibitors", AN 2010: 344827; 239th Conference Meeting Abstract; 2010 ACS on SciFinder.

O'Neill, Brian T.; et. al.; "Pyrrolidine ss-secretase inhibitors for the treatment of Alzheimer's disease", AN 2010: 344728; 239th Conference Meeting Abstract; 2010 ACS on SciFinder.

Cumming, Jared N.; Novel iminopyrimidinone β-secretase (BACE)Inhibitors: Part 1, P1-P3 SAR; AN 2010:344544; 239th Conference Meeting Abstract; 2010 ACS on SciFinder.

Keana, John F.W.; et. al."Synthetic Intermediates Potentially Useful for the Synthesis of Tetrodotoxin and Derivatives", Journal of Organic Chemistry; 1976, 41, No. 12; pp. 2124-2129.

Keana, John F.W.; et. al."Diels-Alder Reactions Involving Heterocyclic Dienophiles Synthesis of Substituted of Hydroquinazolines . . ."; Journal of Organic Chemistry; 1969, 34, No. 11; pp. 3705-3707.

Bolshaya Sovetskaya Entsicolpediya ("Great Russian Encycolopedia"), Moscow, 1976, vol. 25, p. 981.

N. A. Tukavkina, Yu.l. Baukov, Bioorganitcheskaya Khimiya (Bioorganic Chemistry), Moscow, "Meditsina" publishes, 1991, p. 54).

* cited by examiner

ASPARTYL PROTEASE INHIBITORS

RELATED APPLICATIONS

This application claims priority to provisional application U.S. Ser. No. 60/690,537, filed on Jun. 14, 2005, herein incorporated by reference.

FIELD OF THE INVENTION

This invention relates to aspartyl protease inhibitors, pharmaceutical compositions comprising said compounds, their use in the treatment of cardiovascular diseases, cognitive and neurodegenerative diseases, and their use as inhibitors of the Human Immunodeficiency Virus, plasmepsins, cathepsin D and protozoal enzymes.

BACKGROUND

There are a number of aspartic proteases known to date, including pepsin A and C, renin, BACE, BACE 2, Napsin A, and cathepsin D, which have been implicated in pathological conditions. The role of renin-angiotensin system (RAS) in regulation of blood pressure and fluid electrolyte has been well established (Oparil, S, et al. N Engl J Med 1974; 291: 381-401/446-57). The octapeptide Angiotensin-II, a potent vasoconstrictor and stimulator for release of adrenal aldosterone, was processed from the precursor decapeptide Angiotensin-I, which in turn is processed from angiotensinogen by the renin enzyme. Angiotensin-II is also found to play roles in vascular smooth muscle cell growth, inflammation, reactive oxygen species generation and thrombosis and influence atherogenesis and vascular damage. Clinically, the benefit of interruption of the generation of angiotensin-II through antagonism of conversion of angiotensin-I has been well known and there are a number of ACE inhibitor drugs on the market. The blockade of the earlier conversion of angiotensinogen to angiotensin-I, i.e. the inhibition of renin enzyme, is expected to have similar but not identical effects. Since renin is an aspartyl protease whose only natural substrate is angiotensinogen, it is believed that there would be less frequent adverse effect for controlling high blood pressure and related symptoms regulated by angiotensin-II through its inhibition.

Another protease, Cathepsin-D, is involved in lysosomal biogenesis and protein targeting, and may also be involved in antigen processing and presentation of peptide fragments. It has been linked to numerous diseases including, Alzheimer's, Disease, connective tissue disease, muscular dystrophy and breast cancer.

Alzheimer's Disease (AD) is a progressive neurodegenerative disease that is ultimately fatal. Disease progression is associated with gradual loss of cognitive function related to memory, reasoning, orientation and judgment. Behavioral changes including confusion, depression and aggression also manifest as the disease progresses. The cognitive and behavioral dysfunction is believed to result from altered neuronal function and neuronal loss in the hippocampus and cerebral cortex. The currently available AD treatments are palliative, and while they ameliorate the cognitive and behavioral disorders, they do not prevent disease progression. Therefore there is an unmet medical need for AD treatments that halt disease progression.

Pathological hallmarks of AD are the deposition of extracellular β-amyloid (Aβ) plaques and intracellular neurofibrillary tangles comprised of abnormally phosphorylated protein tau. Individuals with AD exhibit characteristic Aβ deposits, in brain regions known to be important for memory and cognition. It is believed that Aβ is the fundamental causative agent of neuronal cell loss and dysfunction which is associated with cognitive and behavioral decline. Amyloid plaques consist predominantly of Aβ peptides comprised of 40-42 amino acid residues, which are derived from processing of amyloid precursor protein (APP). APP is processed by multiple distinct protease activities. Aβ peptides result from the cleavage of APP by β-secretase at the position corresponding to the N-terminus of Aβ, and at the C-terminus by γ-secretase activity. APP is also cleaved by α-secretase activity resulting in the secreted, non-amyloidogenic fragment known as soluble APP.

An aspartyl protease known as BACE-1 has been identified as the β-secretase activity responsible for cleavage of APP at the position corresponding to the N-terminus of Aβ peptides.

Accumulated biochemical and genetic evidence supports a central role of Aβ in the etiology of AD. For example, Aβ has been shown to be toxic to neuronal cells in vitro and when injected into rodent brains. Furthermore inherited forms of early-onset AD are known in which well-defined mutations of APP or the presenilins are present. These mutations enhance the production of Aβ and are considered causative of AD.

Since Aβ peptides are formed as a result of β-secretase activity, inhibition of BACE-1 should inhibit formation of Aβ peptides. Thus inhibition of BACE-1 is a therapeutic approach to the treatment of AD and other cognitive and neurodegenerative diseases caused by Aβ plaque deposition.

Human immunodeficiency virus (HIV), is the causative agent of acquired immune deficiency syndrome (AIDS). It has been clinically demonstrated that compounds such as indinavir, ritonavir and saquinavir which are inhibitors of the HIV aspartyl protease result in lowering of viral load. As such, the compounds described herein would be expected to be useful for the treatment of AIDS. Traditionally, a major target for researchers has been HIV-1 protease, an aspartyl protease related to renin.

In addition, Human T-cell leukemia virus type I (HTLV-I) is a human retrovirus that has been clinically associated with adult T-cell leukemia and other chronic diseases. Like other retroviruses, HTLV-I requires an aspartyl protease to process viral precursor proteins, which produce mature virions. This makes the protease an attractive target for inhibitor design. (Moore, et al. Purification of HTLV-I Protease and Synthesis of Inhibitors for the treatment of HTLV-I Infection 55th Southeast Regional Meeting of the American Chemical Society, Atlanta, Ga., US Nov. 16-19, 2003 (2003), 1073. CODEN; 69EUCH Conference, AN 2004:137641 CAPLUS).

Plasmepsins are essential aspartyl protease enzymes of the malarial parasite. Compounds for the inhibition of aspartyl proteases plasmepsins, particularly I, II, IV and HAP, are in development for the treatment of malaria. (Freire, et al. WO 2002074719. Na Byoung-Kuk, et al., Aspartic proteases of Plasmodium vivax are highly conserved in wild isolates, Korean Journal of Parasitology (2004 June), 42(2) 61-6. Journal code: 9435800) Furthermore, compounds used to target aspartyl proteases plasmepsins (e.g. I, II, IV and HAP), have been used to kill malarial parasites, thus treating patients thus afflicted.

Compounds that act as aspartyl protease inhibitors are described, for example in application U.S. Ser. No. 11/010, 772, filed on Dec. 13, 2004, herein incorporated by reference.

WO/9304047, herein incorporated by reference, describes compounds having a quinazolin-2-(thi)one nucleus. The document alleges that the compounds described therein are inhibitors of HIV reverse transcriptase.

US Publication No. US 2005/0282826 A1, herein incorporated by reference, describes diphenylimidazopyrimidine or -imidazole amines, which are said to be useful for the therapeutic treatment, prevention or amelioration of a disease or disorder characterized by elevated β-amyloid deposits or β-amyloid levels in a patient. Disease states mentioned in the publication include Alzheimer's disease, mild cognative impairment, Down's syndrome, hereditary cerebral hemorrhage with amyloidosis of the Dutch type, cerebral amyloid angiopathy and degenerative dementia.

US Publication No. US 2005/0282825 A1, herein incorporated by reference, describes amino-5,5-diphenylimidazolones, which are said to be useful for the therapeutic treatment, prevention or amelioration of a disease or disorder characterized by elevated β-amyloid deposits or β-amyloid levels in a patient. Disease states mentioned in the publication include Alzheimer's disease, mild cognative impairment, Down's syndrome, hereditary cerebral hemorrhage with amyloidosis of the Dutch type, cerebral amyloid angiopathy and degenerative dementia.

Other publications that disclosed compounds that are useful for treating Alzheimer's disease include WO 2006/044492, which discloses spiropiperidine compounds that are said to be inhibitors of β-secretase, and WO 2006/041404, which discloses substituted amino compounds that are said to be useful for the treatment or prophylaxix of Aβ related pathologies. Both these publications are incorporated by reference.

SUMMARY OF THE INVENTION

The present invention relates to compounds having the structural formula I

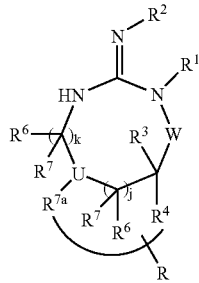

or a stereoisomer, tautomer, or pharmaceutically acceptable salt or solvate thereof, wherein j is 0 or 1;

k is 0 or 1, provided that when k is 1, U cannot be —N—;

W is a bond, —C(=S)—, —S(O)—, —S(O)$_2$—, —C(=O)—, —O—, —C(R$^6$)(R$^7$)—, —N(R$^5$)—, —C(R$^6$)(R$^7$)C(=O)—, or —C(=N(R$^5$))—;

U is —N— or —C(R$^6$)—;

R is 1 to 5 R$^{21}$ groups;

R$^1$, R$^2$ and R$^5$ are independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, —OR$^{15}$, —CN, —C(=NR$^{11}$)R$^8$, —C(O)R$^8$, —C(O)OR$^9$, —S(O)R$^{10}$, —S(O)$_2$R$^{10}$, —C(O)N(R$^{11}$)(R$^{12}$), —S(O)N(R$^{11}$)(R$^{12}$), —S(O)$_2$N(R$^{11}$)(R$^{12}$), —NO$_2$, —N=C(R$^8$)$_2$ and —N(R$^{11}$)(R$^{12}$), provided that R$^1$ and R$^5$ are not both selected from —NO$_2$, —N=C(R$^8$)$_2$ and —N(R$^{11}$)(R$^{12}$);

R$^3$, R$^6$ and R$^7$ are independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, halo, —CH$_2$—O—Si(R$^9$)(R$^{10}$)(R$^{19}$), —SH, —CN, —OR$^9$, —C(O)R$^8$, —C(O)OR$^9$, —C(O)N(R$^{11}$)(R$^{12}$), —SR$^{19}$, —S(O)N(R$^{11}$)(R$^{12}$), —S(O)$_2$N(R$^{11}$)(R$^{12}$), —N(R$^{11}$)(R$^{12}$), —N(R$^{11}$)C(O)R$^8$, —N(R$^{11}$)S(O)R$^{10}$, —N(R$^{11}$)S(O)$_2$R$^{10}$, —N(R$^{11}$)C(O)N(R$^{12}$)(R$^{13}$), —N(R$^{11}$)C(O)OR$^9$ and —C(=NOH)R$^8$;

R$^4$ and R$^{7a}$ are independently selected from the group consisting of a bond, alkylene, arylalkylene, heteroarylalkylene, cycloalkylalkylene, heterocycloalkylalkylene, arylcycloalkylalkylene, heteroarylcycloalkylalkylene, arylheterocycloalkylalkylene, heteroarylheterocycloalkylalkylene, cycloalkylene, arylcycloalkylene, heteroarylcycloalkylene, heterocycloalkylene, arylheterocycloalkylene, heteroarylheterocycloalkylene, alkenylene, arylalkenylene, cycloalkenylene, arylcycloalkenylene, heteroarylcycloalkenylene, heterocycloalkenylene, arylheterocycloalkenylene, heteroarylheterocycloalkenylene, alkynylene, arylalkynylene, arylene, cycloalkylarylene, heterocycloalkylarylene, cycloalkyenylarylene, cycloalkenylarylene, heterocycloalkenylarylene, heteroarylene, cycloalkylheteroarylene, heterocycloalkylheteroarylene, cycloalkenylheteroarylene and heterocycloalkenylheteroarylene, with the proviso that both R$^4$ and R$^{7a}$ are not both a bond;

R$^4$ and R$^{7a}$ together can be a C$_1$ to C$_8$ carbon chain, wherein, optionally, one, two or three ring carbons can be replaced by —O—, —C(O)—, —C(S)—, —S—, —S(O)—, —S(O)$_2$— or —N(R$^5$)—, and R$^4$ and R$^{7a}$ together with the carbon atoms to which they are attached, form a 3 to 8 membered ring, optionally substituted by R, with the following provisos:

that when at least one of the carbons is replaced by —O—, —C(O)—, —C(S)—, —S—, —S(O)—, —S(O)$_2$— or —N(R$^5$)—, then the number of carbons in the R$^4$ and R$^{7a}$ portion of the chain that bonds with U is b, wherein b is 0 to 5, and the number of carbons that are in the R$^4$ and R$^{7a}$ portion of the chain that bonds with the carbon of —C(R$^3$)— is c, wherein c is 0 to 5;

that when j is 0 or 1, at least one of the ring carbons must be replaced by —O—, —C(O)—, —C(S)—, —S—, —S(O)—, —S(O)$_2$— or —N(R$^5$)—;

that when j is 0 or 1 and only one ring carbon is replaced with —O—, —C(O)—, —C(S)—, —S—, —S(O)—, —S(O)$_2$— or —N(R$^5$)—, R$^4$ and R$^{7a}$ cannot form a cycloalkylether;

$R^8$ is independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, —$OR^{15}$, —$N(R^{15})(R^{16})$, —$N(R^{15})C(O)R^{16}$, —$N(R^{15})S(O)R^{16}$, —$N(R^{15})S(O)_2R^{16}$, —$N(R^{15})S(O)_2N(R^{16})(R^{17})$, —$N(R^{15})S(O)N(R^{16})(R^{17})$, —$N(R^{15})C(O)N(R^{16})(R^{17})$ and —$N(R^{15})C(O)OR^{16}$;

$R^9$ is independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, and heterocycloalkenylheteroaryl;

$R^{10}$ is independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl and —$N(R^{15})(R^{16})$;

$R^{11}$, $R^{12}$ and $R^{13}$ are independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, —$C(O)R^8$, —$C(O)OR^9$, —$S(O)R^{10}$, —$S(O)_2R^{10}$, —$C(O)N(R^{15})(R^{16})$, —$S(O)N(R^{15})(R^{16})$, —$S(O)_2N(R^{15})(R^{16})$ and —CN;

$R^{15}$, $R^{16}$ and $R^{17}$ are independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, $R^{18}$-alkyl, $R^{18}$-arylalkyl, $R^{18}$-heteroarylalkyl, $R^{18}$-cyloalkylalkyl, $R^{18}$-heterocycloalkylalkyl, $R^{18}$-arylcycloalkylalkyl, $R^{18}$-heteroarylcycloalkylalkyl, $R^{18}$-arylheterocycloalkylalkyl, $R^{18}$-heteroarylheterocycloalkylalkyl, $R^{18}$-cycloalkyl, $R^{18}$-arylcycloalkyl, $R^{18}$-heteroarylcycloalkyl, $R^{18}$-heterocycloalkyl, $R^{18}$-arylheterocycloalkyl, $R^{18}$-heteroarylheterocycloalkyl, $R^{18}$-alkenyl, $R^{18}$-arylalkenyl, $R^{18}$-cycloalkenyl, $R^{18}$-arylcycloalkenyl, $R^{18}$-heteroarylcycloalkenyl, $R^{18}$-heterocycloalkenyl, $R^{18}$-arylheterocycloalkenyl, $R^{18}$-heteroarylheterocycloalkenyl, $R^{18}$-alkynyl, $R^{18}$-arylalkynyl, $R^{18}$-aryl, $R^{18}$-cycloalkylaryl, $R^{18}$-heterocycloalkylaryl, $R^{18}$-cycloalkenylaryl, $R^{18}$-heterocycloalkenylaryl, $R^{18}$-heteroaryl, $R^{18}$-cycloalkylheteroaryl, $R^{18}$-heterocycloalkylheteroaryl, $R^{18}$-cycloalkenylheteroaryl, and $R^{18}$-heterocycloalkenylheteroaryl; or $R^{15}$, $R^{16}$ and $R^{17}$ are

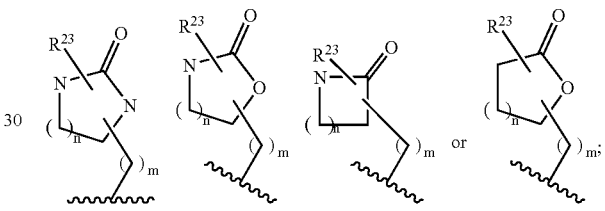

wherein $R^{23}$ numbers 0 to 5 substituents, m is 0 to 6 and n is 0 to 5;

$R^{18}$ is 1-5 substituents independently selected from the group consisting of alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, —$NO_2$, halo, HO-alkoxyalkyl, —$CF_3$, —CN, alkyl-CN, —$C(O)R^{19}$, —C(O)OH, —$C(O)OR^{19}$, —$C(O)NHR^{20}$, —$C(O)NH_2$, —$C(O)NH_2$—$C(O)N(alkyl)_2$, —$C(O)N(alkyl)$(aryl), —C(O)N(alkyl)(heteroaryl), —$SR^{19}$, —$S(O)_2R^{20}$, —$S(O)NH_2$, —S(O)NH(alkyl), —S(O)N(alkyl)(alkyl), —S(O)NH(aryl), —$S(O)_2NH_2$, —$S(O)_2NHR^{19}$, —$S(O)_2NH$(heterocycloalkyl), —$S(O)_2N(alkyl)_2$, —$S(O)_2N(alkyl)$(aryl), —$OCF_3$, —OH, —$OR^{20}$, —O-heterocycloalkyl, —O-cycloalkylalkyl, —O-heterocycloalkylalkyl, —$NH_2$, —$NHR^{20}$, —$N(alkyl)_2$, —$N(arylalkyl)_2$, —N(arylalkyl)-(heteroarylalkyl), —$NHC(O)R^{20}$, —$NHC(O)NH_2$, —NHC(O)NH(alkyl), —NHC(O)N(alkyl)(alkyl), —N(alkyl)C(O)NH(alkyl), —N(alkyl)C(O)N(alkyl)(alkyl), —$NHS(O)_2R^{20}$, —$NHS(O)_2NH(alkyl)$, —$NHS(O)_2N(alkyl)(alkyl)$, —$N(alkyl)S(O)_2NH(alkyl)$ and —$N(alkyl)S(O)_2N(alkyl)(alkyl)$;

or two R$^{18}$ moieties on adjacent carbons can be linked together to form

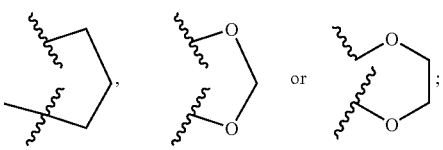

R$^{19}$ is alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl or heterocycloalkenylheteroaryl;

R$^{20}$ is halo substituted aryl, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl or heterocycloalkenylheteroaryl, and wherein each of the alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, in R, R$^1$, R$^2$, R$^3$, R$^4$, R$^5$, R$^6$, R$^7$; R$^8$, R$^9$, R$^{10}$, R$^{11}$, R$^{12}$ and R$^{13}$ are independently unsubstituted or substituted by 1 to 5 R$^{21}$ groups independently selected from the group consisting of alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, halo, —CN, —C(=NR$^{11}$)R$^{15}$, —OR$^{15}$, —C(O)R$^{15}$, —C(O)OR$^{15}$, —C(O)N(R$^{15}$)(R$^{16}$), —SR$^{15}$, —S(O)N(R$^{15}$)(R$^{16}$), —CH(R$^{15}$)(R$^{16}$), —S(O)$_2$N(R$^{15}$)(R$^{16}$), C(=NOR$^{15}$)R$^{16}$, —P(O)(OR$^{15}$)(OR$^{16}$), —N(R$^{15}$)(R$^{16}$), -alkyl-N(R$^{15}$)(R$^{16}$), —N(R$^{15}$)C(O)R$^{16}$, —CH$_2$—N(R$^{15}$)C(O)R$^{16}$, —CH$_2$—N(R$^{15}$)C(O)N(R$^{16}$)(R$^{17}$), —CH$_2$—R$^{15}$; —CH$_2$N(R$^{15}$)(R$^{16}$), —N(R$^{15}$)S(O)R$^{16}$, —N(R$^{15}$)S(O)$_2$R$^{16}$, —CH$_2$—N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$), —CH$_2$—N(R$^{15}$)C(O)N(R$^{16}$)(R$^{17}$), —N(R$^{15}$)C(O)OR$^{16}$, —CH$_2$—N(R$^{15}$)C(O)OR$^{16}$, —S(O)R$^{15}$, —N$_3$, —NO$_2$ and —S(O)$_2$R$^{15}$;

and wherein each of the alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl and heterocycloalkenylheteroaryl groups in R$^{21}$ are independently unsubstituted or substituted by 1 to 5 R$^{22}$ groups independently selected from the group consisting of alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, halo, —CF$_3$, —CN, —C(=NR$^{11}$)R$^{15}$, —OR$^{15}$, —C(O)R$^{15}$, —C(O)OR$^{15}$, -alkyl-C(O)OR$^{15}$, —C(O)N(R$^{15}$)(R$^{16}$), —SR$^{15}$, —S(O)N(R$^{15}$)(R$^{16}$), —S(O)$_2$N(R$^{15}$)(R$^{16}$), —C(=NOR$^{15}$)R$^{16}$, —P(O)(OR$^{15}$)(OR$^{16}$), —N(R$^{15}$)(R$^{16}$), -alkyl-N(R$^{15}$)(R$^{16}$), —N(R$^{15}$)C(O)R$^{16}$, —CH$_2$—N(R$^{15}$)C(O)R$^{16}$, —N(R$^{15}$)S(O)R$^{16}$, —N(R$^{15}$)S(O)$_2$R$^{16}$, —CH$_2$—N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$), —CH$_2$—N(R$^{15}$)C(O)N(R$^{16}$)(R$^{17}$), —N(R$^{15}$)C(O)OR$^{16}$, —CH$_2$—N(R$^{15}$)C(O)OR$^{16}$, —N$_3$, —NO$_2$, —S(O)R$^{15}$ and —S(O)$_2$R$^{15}$;

or two R$^{21}$ or two R$^{22}$ moieties on adjacent carbons can be linked together to form

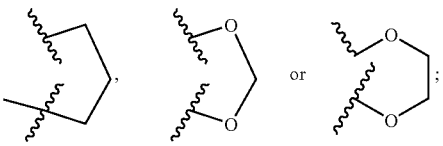

and when R$^{21}$ or R$^{22}$ are selected from the group consisting of —C(=NOR$^{15}$)R$^{16}$, —N(R$^{15}$)C(O)R$^{16}$, —CH$_2$—N(R$^{15}$)C(O)R$^{16}$, —N(R$^{15}$)S(O)R$^{16}$, —N(R$^{15}$)S(O)$_2$R$^{16}$, —CH$_2$—N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$), —CH$_2$—N(R$^{15}$)C(O)N(R$^{16}$)(R$^{17}$), —N(R$^{15}$)C(O)OR$^{16}$ and —CH$_2$—N(R$^{15}$)C(O)OR$^{16}$, R$^{15}$ and R$^{16}$ together can be a C$_2$ to C$_4$ chain wherein, optionally, one, two or three ring carbons can be replaced by —C(O)— or —N(H)— and R$^{15}$ and R$^{16}$, together with the atoms to which they are attached, form a 5 to 7 membered ring, optionally substituted by R$^{23}$;

R$^{23}$ is 1 to 5 groups independently selected from the group consisting of alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, halo, —CN, —OR$^{24}$, —C(O)R$^{24}$, —C(O)OR$^{24}$, —C(O)N(R$^{24}$)(R$^{25}$), —SR$^{24}$, —S(O)N(R$^{24}$)(R$^{25}$), —S(O)$_2$N(R$^{24}$)(R$^{25}$), —C(=NOR$^{24}$)R$^{25}$, —P(O)(OR$^{24}$)(OR$^{25}$), —N(R$^{24}$)(R$^{25}$), -alkyl-N(R$^{24}$)(R$^{25}$), —N(R$^{24}$), C(O)R$^{25}$, —CH$_2$—N(R$^{24}$)C(O) R$^{25}$, —N(R$^{24}$)S(O)R$^{25}$, —N(R$^{24}$)S(O)$_2$R$^{25}$, —CH$_2$—N(R$^{24}$)S(O)$_2$R$^{25}$, —N(R$^{24}$)S(O)$_2$N(R$^{25}$)(R$^{26}$), —N(R$^{24}$)S(O)N(R$^{25}$)(R$^{26}$), —N(R$^{24}$)C(O)N(R$^{25}$)(R$^{26}$), —CH$_2$—N(R$^{24}$)C(O)N(R$^{25}$)(R$^{26}$), —N(R$^{24}$)C(O)OR$^{25}$, —CH$_2$—N(R$^{24}$)C(O)OR$^{25}$, —S(O)R$^{24}$ and —S(O)$_2$R$^{24}$; and wherein each of the alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl and heterocycloalkenylheteroaryl groups in R$^{23}$ are independently unsubstituted or substituted by 1 to 5 R$^{27}$ groups independently selected from the group consisting of alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, halo, —CF$_3$, —CN, —OR$^{24}$, —C(O)R$^{24}$, —C(O)OR$^{24}$, alkyl-C(O)OR$^{24}$, —C(O)N(R$^{24}$)(R$^{25}$), —SR$^{24}$, —S(O)N(R$^{24}$)(R$^{25}$), —S(O)$_2$N(R$^{24}$)(R$^{25}$), —C(=NOR$^{24}$)R$^{25}$, —P(O)(OR$^{24}$)(OR$^{25}$), —N(R$^{24}$)(R$^{25}$), -alkyl-N(R$^{24}$)(R$^{25}$), —N(R$^{24}$)C(O)R$^{25}$, —CH$_2$—N(R$^{24}$)C(O)R$^{25}$, —N(R$^{24}$)S(O)R$^{25}$, —N(R$^{24}$)S(O)$_2$R$^{25}$, —CH$_2$—N(R$^{24}$)S(O)$_2$R$^{25}$, —N(R$^{24}$)S(O)$_2$N(R$^{25}$)(R$^{26}$), —N(R$^{24}$)S(O)N(R$^{25}$)(R$^{26}$), —N(R$^{24}$)C(O)N(R$^{25}$)(R$^{26}$), —CH$_2$—N(R$^{24}$)C(O)N(R$^{25}$)(R$^{26}$), —N(R$^{24}$)C(O)OR$^{25}$, —CH$_2$—N(R$^{24}$)C(O)OR$^{25}$, —S(O)R$^{24}$ and —S(O)$_2$R$^{24}$;

R$^{24}$, R$^{25}$ and R$^{26}$ are independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, R$^{27}$-alkyl, R$^{27}$-arylalkyl, R$^{27}$-heteroarylalkyl, R$^{27}$-cycloalkylalkyl, R$^{27}$-heterocycloalkylalkyl, R$^{27}$-arylcycloalkylalkyl, R$^{27}$-heteroarylcycloalkylalkyl, R$^{27}$-arylheterocycloalkylalkyl, R$^{27}$-heteroarylheterocycloalkylalkyl, R$^{27}$-cycloalkyl, R$^{27}$-arylcycloalkyl, R$^{27}$-heteroarylcycloalkyl, R$^{27}$-heterocloalkyl, R$^{27}$-arylheterocycloalkyl, R$^{27}$-heteroarylheterocycloalkyl, R$^{27}$-alkenyl, R$^{27}$-arylalkenyl, R$^{27}$-cycloalkenyl, R$^{27}$-arylcycloalkenyl, R$^{27}$-heteroarylcycloalkenyl, R$^{27}$-heterocycloalkenyl, R$^{27}$-arylheterocycloalkenyl, R$^{27}$-heteroarylheterocycloalkenyl, R$^{27}$-alkynyl, R$^{27}$-arylalkynyl, R$^{27}$-aryl, R$^{27}$-cycloalkylaryl, R$^{27}$-heterocycloalkylaryl, R$^{27}$-cycloalkenylaryl, R$^{27}$-heterocycloalkenylaryl, R$^{27}$-heteroaryl, R$^{27}$-cycloalkylheteroaryl, R$^{27}$-heterocycloalkylheteroaryl, R$^{27}$-cycloalkenylheteroaryl and R$^{27}$-heterocycloalkenylheteroaryl;

R$^{27}$ is 1-5 substituents independently selected from the group consisting of alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, —NO$_2$, halo, —CF$_3$, —CN, alkyl-CN, —C(O)R$^{28}$, —C(O)OH, —C(O)OR$^{28}$, —C(O)NHR$^{29}$, —C(O)N(alkyl)$_2$, —C(O)N(alkyl)(aryl), —C(O)N(alkyl)(heteroaryl), —SR$^{28}$, —S(O)$_2$R$^{29}$, —S(O)NH$_2$, —S(O)NH(alkyl), —S(O)N(alkyl)(alkyl), —S(O)NH(aryl), —S(O)$_2$NH$_2$, —S(O)$_2$NHR$^{28}$, —S(O)$_2$NH(aryl), —S(O)$_2$NH(heterocycloalkyl), —S(O)$_2$N(alkyl)$_2$, —S(O)$_2$N(alkyl)(aryl), —OH, —OR$^{29}$ —O-heterocycloalkyl, —O-cycloalkylalkyl, —O-heterocycloalkylalkyl, —NH$_2$, —NHR$^{29}$, —N(alkyl)$_2$, —N(arylalkyl)$_2$, —N(arylalkyl)(heteroarylalkyl), —NHC(O)R$^{29}$, —NHC(O)NH$_2$, —NHC(O)NH(alkyl), —NHC(O)N(alkyl)(alkyl), —N(alkyl)C(O)NH(alkyl), —N(alkyl)C(O)N(alkyl)(alkyl), —NHS(O)$_2$R$^{29}$, —NHS(O)$_2$NH(alkyl), —NHS(O)$_2$N(alkyl)(alkyl), —N(alkyl)S(O)$_2$NH(alkyl) and —N(alkyl)S(O)$_2$N(alkyl)(alkyl);

R$^{28}$ is alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl or heterocycloalkenylheteroaryl;

R$^{29}$ is alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl or heterocycloalkenylheteroaryl;

$R^{30}$ is alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl or heterocycloalkenylheteroaryl;

and $R^{31}$ is alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl;

with the following proviso, that when U, $R^{7a}$ and $R^4$ cyclize to form the following bicyclic structure:

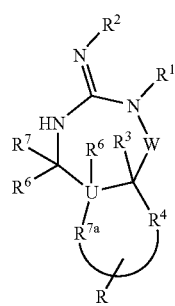

W cannot be a bond.

In another aspect, the invention relates to a pharmaceutical composition comprising at least one compound of formula I and a pharmaceutically acceptable carrier.

In another aspect, the invention comprises the method of inhibiting aspartyl proteases comprising administering at least one compound of formula I to a patient in need of such treatment.

More specifically, the invention comprises: the method of treating a cardiovascular disease such as hypertension, renal failure, congestive heart failure or another disease modulated by renin inhibition; the method of treating Human Immunodeficiency Virus; the method of treating a cognitive or neurodegenerative disease such as Alzheimer's Disease; the method of inhibiting plasmepsins I and II for treatment of malaria; the method of inhibiting Cathepsin D for the treatment of Alzheimer's Disease, breast cancer, and ovarian cancer; and the method of inhibiting protozoal enzymes, for example inhibition of plasmodium falciparnum, for the treatment of fungal infections. Said method of treatment comprise administering at least one compound of formula I to a patient in need of such treatment. In particular, the invention comprises the method of treating Alzheimer's Disease comprising administering at least one compound of formula I to a patient in need of such treatment.

In another aspect, the invention comprises the method of treating Alzheimer's Disease comprising administering to a patient in need of such treatment a combination of at least one compound of formula I and a cholinesterase inhibitor or a muscarinic $m_1$ agonist or $m_2$ antagonist.

In a final aspect, the invention relates to a kit comprising in separate containers in a single package pharmaceutical compositions for use in combination, in which one container comprises a compound of formula I in a pharmaceutically acceptable carrier and a second container comprises a cholinesterase inhibitor or a muscarinic $m_1$ agonist or $m_2$ antagonist in a pharmaceutically acceptable carrier, the combined quantities being an effective amount to treat a cognitive disease or neurodegenerative disease such as Alzheimer's Disease.

DETAILED DESCRIPTION

In general, it is understood that divalent groups are to be read left to right.

Preferred compounds of formula I wherein R, $R^1$, $R^2$, $R^3$, $R^4$, $R^6$, $R^7$, $R^{7a}$ and W are as defined above include the following structures:

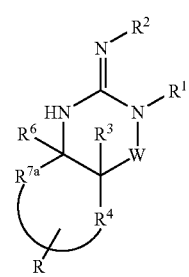

I

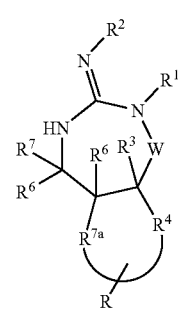

II

-continued

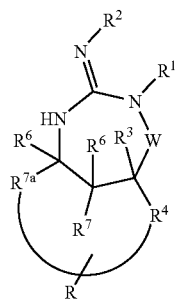

III

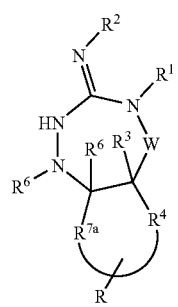

IV provided that in structure II, W is not a bond.

Compounds of formula I wherein R, R¹, R², R³, R⁵, R⁶, R⁷ and W are as defined above also include the following structures:

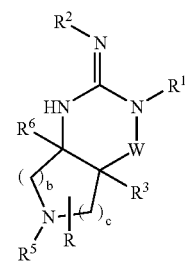

wherein b is 1 to 5 and c is 0 to 5.

or

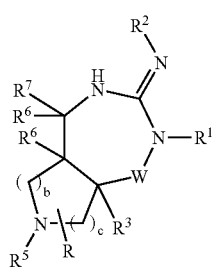

wherein R, R¹, R², R³, R⁵, R⁶, R⁷ and W, wherein b is 1 to 5 and c is 0 to 5 or wherein R, R¹, R², R³, R⁵, R⁶, R⁷ and W are as defined above, b is 1 to 4 and c is 0 to 4.

Preferred compounds of formula I are those compounds wherein R¹ is alkyl or more preferably, R¹ is methyl.

More preferred compounds of the invention are those of formula I wherein R² is H.

Another group of preferred compounds of formula I are those compounds wherein R⁶ is aryl, (R²¹)₁₋₅-aryl, heteroaryl or (R²¹)₁₋₅-heteroaryl or even more preferably, R⁶ is Preferred compounds of formula I are those compounds wherein R²¹ is —CN, halo, aryl, (R²²)₁₋₂-aryl, heteroaryl or (R²²)₁₋₂-heteroaryl.

Preferred compounds of formula I are those compounds wherein R²² is —CN, halo or alkyne, or more preferably, R²² is F or Preferred compounds of formula I are those compounds wherein R²¹ is

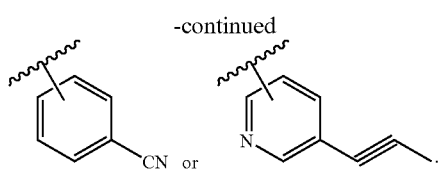

More preferred compounds of formula I are those compounds wherein W is —C(O)—.

Another group of preferred compounds of formula I are those compounds wherein $R^4$ and $R^{7a}$ form $R^4$ and $R^{7a}$ form

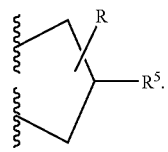

Preferred compounds of formula I are those compounds wherein R is halo, more preferably where R is F.

Preferred compounds of formula I are those compounds wherein

R is H or halo;
$R^1$ is alkyl;
$R^2$ is H;
$R^6$ is $R^{21}$-aryl;
$R^{21}$ is $R^{22}$-aryl;
$R^{22}$ is halo or CN;
W is —C(O)—;

and
$R^4$ and $R^{7a}$ form

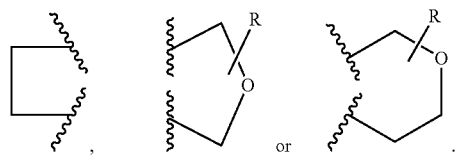

Another group of preferred compounds of formula I are those compounds wherein
$R^1$ is alkyl;
$R^2$ is H;
$R^6$ is $R^{21}$-aryl;
$R^{21}$ is $R^{22}$-aryl;
$R^{22}$ is halo or CN;
W is —C(O)—;

and
$R^4$ and $R^{7a}$ form

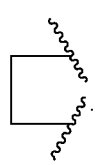

An even further group of preferred compounds of formula I are those compounds wherein $R^1$ is methyl;
$R^2$ is H;
$R^6$ is

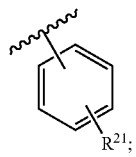

$R^{21}$ is

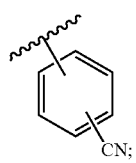

W is —C(O)—;
and
$R^4$ and $R^{7a}$ form

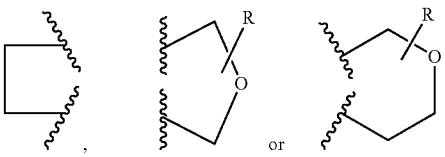

In a group of preferred compounds of formula I are those compounds having the structure:

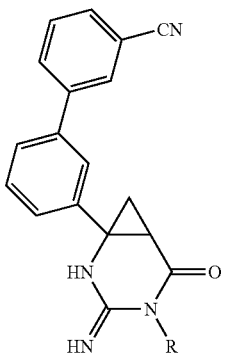

wherein R is defined herein.

The following preferred compounds of formula I have the following structures;

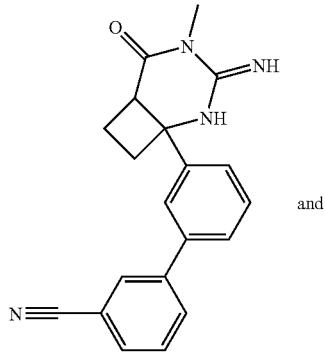

and

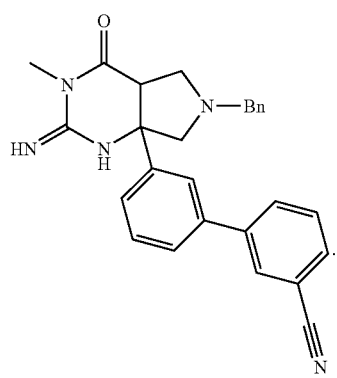

An further group of preferred compounds of formula I are those compounds where $R^4$ and $R^{7a}$ form

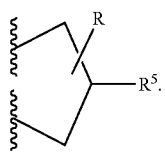

A further group of preferred compounds of formula I are those compounds having the following structure

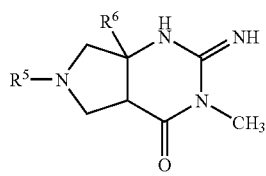

wherein $R^5$ and $R^6$ are as defined as above.

A group of preferred compounds of formula I are those compounds where $R^5$ is independently selected from the group consisting of arylalkyl, aryl, heteroaryl, —C(=NR$^{11}$)R$^8$, —C(O)R$^8$, —C(O)OR$^9$, aryl-R$^{21}$ and heteroaryl-R$^{21}$, or more preferably, $R^5$ is

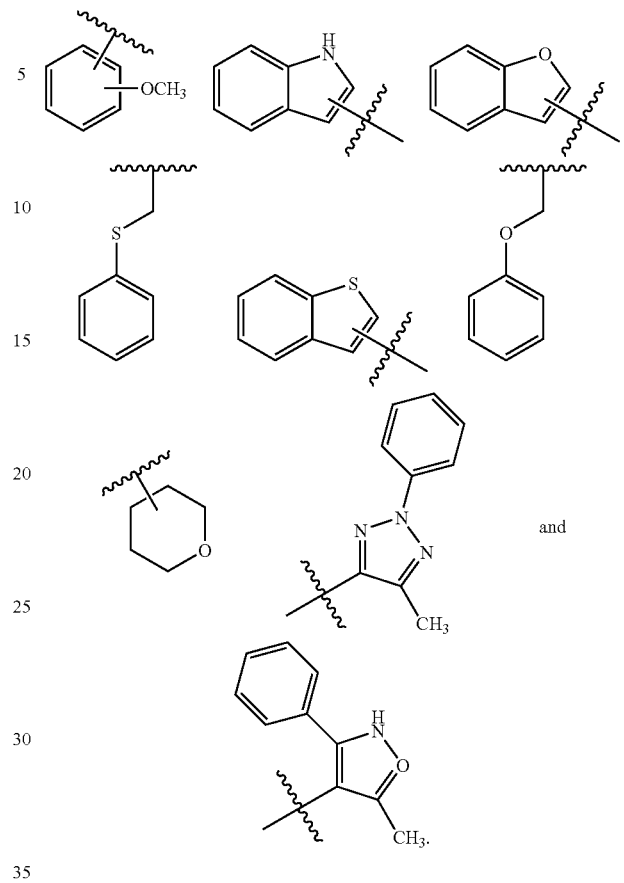

and

An even further group of preferred compounds of formula I are those compounds where $R^{18}$ is 1-5 substituents independently selected from the group consisting of alkyl, halo, —CF$_3$, —CN, —SR$^{19}$ and —OR$^{20}$, or even more preferably, $R^{18}$ is 1-5 substituents independently selected from the group consisting of halo, —CN, —OCH(CH$_3$)$_2$, —OCH$_3$, —CH$_3$,

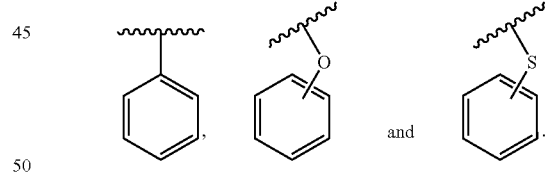

An even further group of preferred compounds of formula I are those compounds wherein $R^{21}$ is 1-5 substituents independently selected from the group consisting of halo, —OCH (CH$_3$)$_2$, —CH$_3$, —CF$_3$, —OCH$_3$, —CH(CH$_3$)$_2$ and —CN.

It is noted that the carbons of formula I may be replaced with 1 to 3 silicon atoms so long as all valency requirements are satisfied.

As used above, and throughout the specification, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. Non-limiting examples of suitable alkyl groups include methyl, ethyl, n-propyl, isopropyl, n-butyl, t-butyl, n-pentyl, heptyl, nonyl and decyl. $R^{21}$-substituted alkyl groups include fluoromethyl, trifluoromethyl and cyclopropylmethyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl, 3-methylbutynyl, n-pentynyl, and decynyl.

"Aryl" means an aromatic monocyclic or multicyclic ring system comprising about 6 to about 14 carbon atoms, preferably about 6 to about 10 carbon atoms. The aryl group can be optionally substituted with one or more substituents (e.g., $R^{18}$, $R^{21}$, $R^{22}$, etc.) which may be the same or different, and are as defined herein or two substituents on adjacent carbons can be linked together to form

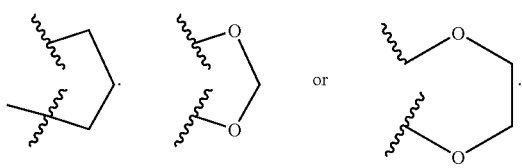

Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one to four of the ring atoms is an element other than carbon, for example nitrogen, oxygen or sulfur, alone or in combination. Preferred heteroaryls contain about 5 to about 6 ring atoms. The "heteroaryl" can be optionally substituted by one or more $R^{21}$ substituents which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Cycloalkyl" means a non-aromatic mono- or multicyclic ring system comprising about 3 to about 15 carbon atoms, preferably about 5 to about 10 carbon atoms. Preferred cycloalkyl rings contain about 5 to about 7 ring atoms. The cycloalkyl can be optionally substituted with one or more $R^{21}$ substituents which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalin, norbornyl, adamantyl and the like. Further non-limiting examples of cycloalkyl include the following

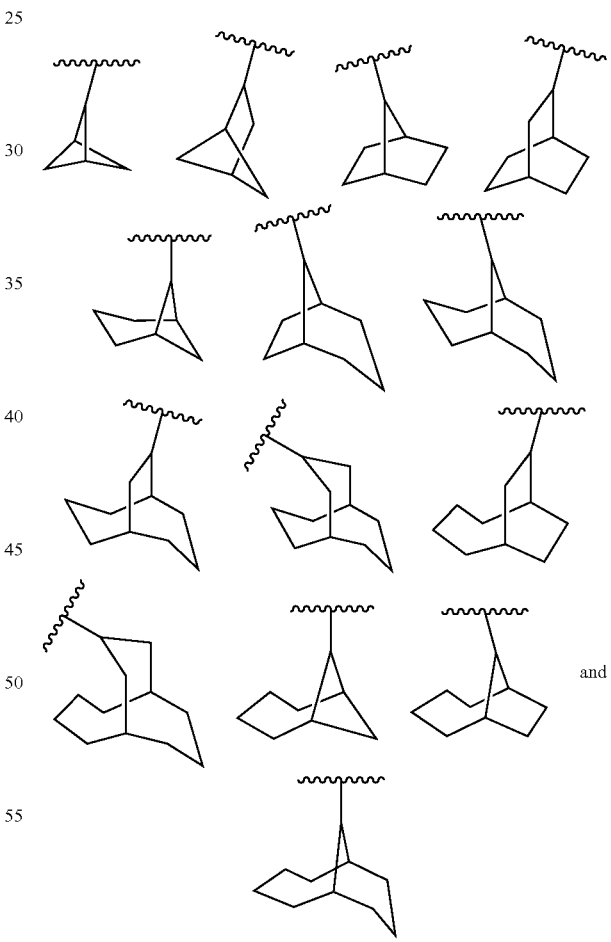

"Cycloalkylether" means a non-aromatic ring of 3 to 15 atoms comprising an oxygen atom and 2 to 14 carbon atoms. Ring carbon atoms can be substituted, provided that substituents adjacent to the ring oxygen do not include halo or substituents joined to the ring through an oxygen, nitrogen or sulfur atom.

"Cycloalkenyl" means a non-aromatic mono or multicyclic ring system comprising about 3 to about 15 carbon atoms, preferably about 5 to about 10 carbon atoms which contains at least one carbon-carbon double bond. The cycloalkenyl ring can be optionally substituted with one or more $R^{21}$ substituents which may be the same or different, and are as defined above. Preferred cycloalkenyl rings contain about 5 to about 7 ring atoms. Non-limiting examples of suitable monocyclic cycloalkenyls include cyclopentenyl, cyclohexenyl, cycloheptenyl, and the like. Non-limiting example of a suitable multicyclic cycloalkenyl is norbornylenyl.

"Heterocyclenyl" (or "heterocycloalkenyl") means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable monocyclic azaheterocyclenyl groups include 1,2,3,4-tetrahydropyridyl, 1,2-dihydropyridyl, 1,4-dihydropyridyl, 1,2,3,6-tetrahydropyridyl, 1,4,5,6-tetrahydropyrimidyl, 2-pyrrolinyl, 3-pyrrolinyl, 2-imidazolinyl, 2-pyrazolinyl, and the like. Non-limiting examples of suitable oxaheterocyclenyl groups include 3,4-dihydro-2H-pyran, dihydrofuranyl, fluorodihydrofuranyl, and the like. Non-limiting example of a suitable multicyclic oxaheterocyclenyl group is 7-oxabicyclo[2.2.1]heptenyl. Non-limiting examples of suitable monocyclic thiaheterocyclenyl rings include dihydrothiophenyl, dihydrothiopyranyl, and the like.

"Halo" means fluoro, chloro, bromo, or iodo groups. Preferred are fluoro, chloro or bromo, and more preferred are fluoro and chloro.

"Haloalkyl" means an alkyl as defined above wherein one or more hydrogen atoms on the alkyl is replaced by a halo group defined above.

"Heterocyclyl" (or heterocycloalkyl) means a non-aromatic saturated monocyclic or multicyclic ring system comprising about 3 to about 10 ring atoms, preferably about 5 to about 10 ring atoms, in which 1-3, preferably 1 or 2 of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The heterocyclyl can be optionally substituted by one or more $R^{21}$ substituents which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"Arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Arylcycloalkyl" means a group derived from a fused aryl and cycloalkyl as defined herein. Preferred arylcycloalkyls are those wherein aryl is phenyl and cycloalkyl consists of about 5 to about 6 ring atoms. The arylcycloalkyl can be optionally substituted by 1-5 $R^{21}$ substituents. Non-limiting examples of suitable arylcycloalkyls include indanyl and 1,2,3,4-tetrahydronaphthyl and the like. The bond to the parent moiety is through a non-aromatic carbon atom.

"Arylheterocycloalkyl" means a group derived from a fused aryl and heterocycloalkyl as defined herein. Preferred arylcycloalkyls are those wherein aryl is phenyl and heterocycloalkyl consists of about 5 to about 6 ring atoms. The arylheterocycloalkyl can be optionally substituted by 1-5 $R^{21}$ substituents. Non-limiting examples of suitable arylheterocycloalkyls include

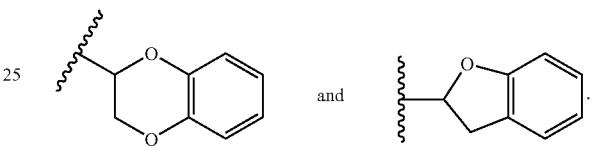

The bond to the parent moiety is through a non-aromatic carbon atom.

Similarly, "heteroarylalkyl" "cycloalkylalkyl" and "heterocycloalkylalkyl" mean a heteroaryl-, cycloalkyl- or heterocycloalkyl-alkyl- group in which the heteroaryl, cycloalkyl, heterocycloalkyl and alkyl are as previously described. It is also understood that the terms "arylcycloalkylalkyl", "heteroarylcycloalkylalkyl", "arylheterocycloalkylalkyl", "heteroarylheterocycloalkylalkyl", "heteroarylcycloalkyl", "heteroarylheterocycloalkyl", "arylcycloalkenyl", "heteroarylcycloalkenyl", "heterocycloalkenyl", "arylheterocycloalkenyl", "heteroarylheterocycloalkenyl", "cycloalkylaryl", "heterocycloalkylaryl", "heterocycloalkenylaryl", "heterocycloalkylheteroaryl", "cycloalkenylaryl" "cycloalkenylheteroaryl", "heterocycloalkenylaryl" and "heterocycloalkenylheteroaryl" similarly represented by the combination of the groups aryl-, cycloalkyl-, alkyl-, heteroaryl-, heterocycloalkyl-, cycloalkenyl- and heterocycloalkenyl- as previously described. Preferred groups contain a lower alkyl group. The bond to the parent moiety is through the alkyl.

"Acyl" means an H—C(O)—, alkyl-C(O)—, alkenyl-C(O)—, alkynyl-C(O)— or cycloalkyl-C(O)— group in which the various groups are as previously described. The bond to the parent moiety is through the carbonyl. Preferred acyls contain a lower alkyl. Non-limiting examples of suitable acyl groups include formyl, acetyl, propanoyl, 2-methylpropanoyl, butanoyl and cyclohexanoyl.

"Alkoxy" means an alkyl-O— group in which the alkyl group is as previously described. Non-limiting examples of suitable alkoxy groups include methoxy, ethoxy, n-propoxy, isopropoxy, n-butoxy and heptoxy. The bond to the parent moiety is through the ether oxygen.

"Alkoxyalkyl" means a group derived from an alkoxy and alkyl as defined herein. The bond to the parent moiety is through the alkyl.

"Arylalkenyl" means a group derived from aryl and alkenyl as defined herein. Preferred arylalkenyls are those wherein aryl is phenyl and the alkenyl consists of about 3 to about 6 atoms. The arylalkenyl can be optionally substituted by one or more $R^{27}$ substituents. The bond to the parent moiety is through a non-aromatic carbon atom.

"Arylalkynyl" means a group derived from aryl and alkynyl as defined herein. Preferred arylalkynyls are those wherein aryl is phenyl and the alkynyl consists of about 3 to about 6 atoms. The arylalkynyl can be optionally substituted by one or more $R^{27}$ substituents. The bond to the parent moiety is through a non-aromatic carbon atom.

The suffix "ene" on alkyl, aryl, hetercycloalkyl, etc. indicates a divalent moiety, e.g., —CH₂CH₂— is ethylene, and

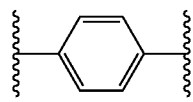

is para-phenylene.

It is understood that multicyclic divalent groups, for example, arylheterocycloalkylene, can be attached to other groups via bonds that are formed on either ring of said group. For example,

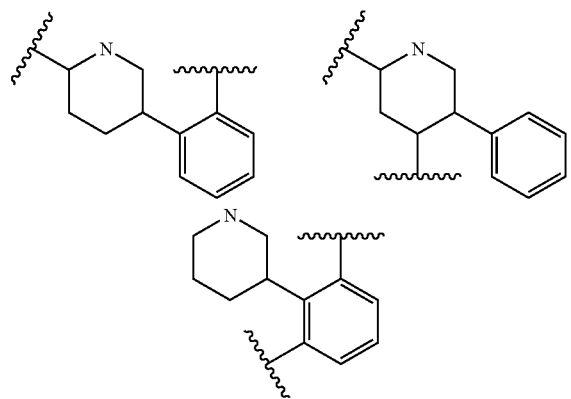

The term "optionally substituted" means optional substitution with the specified groups, radicals or moieties, in available position or positions.

Substitution on a cycloalkylalkyl, heterocycloalkylalkyl, arylalkyl, or heteroarylalkyl moiety includes substitution on the ring portion and/or on the alkyl portion of the group.

When a variable appears more than once in a group, e.g., $R^8$ in —N=C($R^8$)₂, or a variable appears more than once in the structure of formula I, e.g., $R^{15}$ may appear in both $R^1$ and $R^3$, the variables can be the same or different.

With reference to the number of moieties (e.g., substituents, groups or rings) in a compound, unless otherwise defined, the phrases "one or more" and "at least one" mean that there can be as many moieties as chemically permitted, and the determination of the maximum number of such moieties is well within the knowledge of those skilled in the art. With respect to the compositions and methods comprising the use of "at least one compound of formula I," one to three compounds of formula I can be administered at the same time, preferably one.

As used herein, the term "composition" is intended to encompass a product comprising the specified ingredients in the specified amounts, as well as any product which results, directly or indirectly, from combination of the specified ingredients in the specified amounts.

The wavy line ~~~ as a bond generally indicates a mixture of, or either of, the possible isomers, e.g., containing (R)- and (S)-stereochemistry. For example,

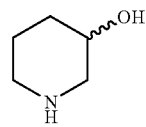

means containing both

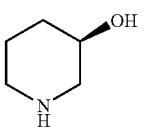 and 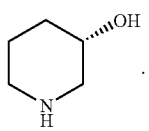

Lines drawn into the ring systems, such as, for example:

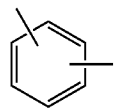

indicate that the indicated line (bond) may be attached to any of the substitutable ring carbon atoms.

As well known in the art, a bond drawn from a particular atom wherein no moiety is depicted at the terminal end of the bond indicates a methyl group bound through that bond to the atom, unless stated otherwise. For example:

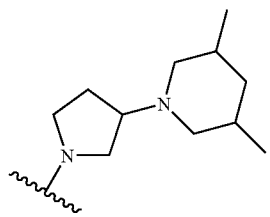

represents

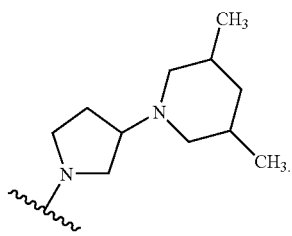

It should also be noted that any heteroatom with unsatisfied valences in the text, schemes, examples, structural formulae, and any Tables herein is assumed to have the hydrogen atom or atoms to satisfy the valences. Those skilled in the art will recognize that certain compounds of formula I are tautomeric, and all such tautomeric forms are contemplated herein as part of the present invention. For example, a compound wherein $R^1$ is H, said compound can be represented by any of the following structures:

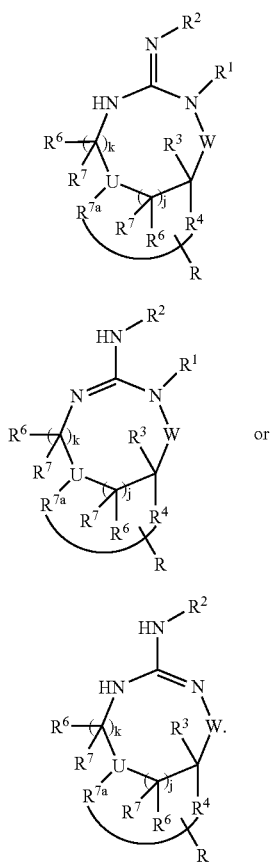

When, $R^8$, for example is, —N($R^{15}$)S(O)$_2$N($R^{16}$)($R^{17}$), and $R^{16}$ and $R^{17}$ form a ring, the moiety formed, is, for example

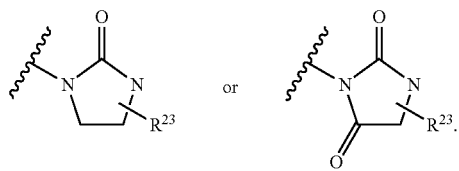

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-(C1-C2)alkyl and piperidino-, pyrrolidino- or morpholino($C_2$-$C_3$) alkyl, and the like.

Similarly, if a compound of Formula (I) contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N-($C_1$-$C_6$)alkoxycarbonylaminomethyl, succinoyl, ($C_1$-$C_6$)alkanoyl, α-amino($C_1$-$C_4$)alkanyl, arylacyl and α-aminoacyl, or α-aminoacyl-α-aminoacyl, where each α-aminoacyl group is independently selected from the naturally occurring L-amino acids, P(O)(OH)$_2$, —P(O)(O($C_1$-$C_6$)alkyl)$_2$ or glycosyl (the radical resulting from the removal of a hydroxyl group of the hemiacetal form of a carbohydrate), and the like.

If a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently ($C_1$-$C_{10}$)alkyl, ($C_3$-$C_7$) cycloalkyl, benzyl, or R-carbonyl is a natural α-aminoacyl or natural α-aminoacyl, —C(OH)C(O)O$Y^1$ wherein $Y^1$ is H, ($C_1$-$C_6$)alkyl or benzyl, —(O$Y^2$)$Y^3$ wherein $Y^2$ is ($C_1$-$C_4$) alkyl and $Y^3$ is ($C_1$-$C_6$)alkyl, carboxy($C_1$-$C_6$)alkyl, amino ($C_1$-$C_4$)alkyl or mono-N- or di-N,N-($C_1$-$C_6$)alkylaminoalkyl, —C($Y^4$)$Y^5$ wherein $Y^4$ is H or methyl and $Y^5$ is mono-N- or di-N,N-($C_1$-$C_6$)alkylamino morpholino, piperidin-1-yl or pyrrolidin-1-yl, and the like.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting aspartyl protease and/or inhibiting BACE-1 and thus producing the desired therapeutic effect in a suitable patient.

The compounds of formula I form salts which are also within the scope of this invention. Reference to a compound of formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the formula I may be formed, for example, by reacting a compound of formula I with an amount of acid or base, such as an equivalent amount, in a medium such as one in which the salt precipitates or in an aqueous medium followed by lyophilization. Acids (and bases) which are generally considered suitable for the formation of pharmaceutically useful salts from basic (or acidic) pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; in *The Orange Book* (Food & Drug Administration, Washington, D.C. on their website); and P. Heinrich Stahl, Camille G. Wermuth (Eds.), *Handbook of Pharmaceutical Salts: Properties, Selection, and Use*, (2002) Int'l. Union of Pure and Applied Chemistry, pp. 330-331. These disclosures are incorporated herein by reference thereto.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, bisulfates, sulfates, sulfonates (such as those mentioned herein), tartarates, thiocyanates, toluenesulfonates (also known as tosylates), undecanoates, and the like.

Exemplary basic salts include ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis(dehydroabietyl)ethylenediamine), N-methyl-D-glucamines, N-methyl-D-glucamides, t-butyl amines, piperazine, phenylcyclohexylamine, choline, tromethamine, and salts with amino acids such as arginine, lysine and the like. Basic nitrogen-containing groups may be quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "prodrug" and the like, is intended to equally apply to the salt, solvate and prodrug of enantiomers, stereoisomers, rotamers, tautomers, racemates or prodrugs of the inventive compounds.

Polymorphic forms of the compounds of formula I, and of the salts, solvates and prodrugs of the compounds of formula I, are intended to be included in the present invention Compounds of formula I can be made using procedures known in the art. The following reaction schemes show typical procedures, but those skilled in the art will recognize that other procedures can also be suitable.

In the Schemes and in the Example below, the following abbreviations are used:
  room temperature: r.t.
  high pressure liquid chromatography: HPLC
  reverse-phase HPLC: RP-HPLC
  liquid chromatography mass spectrometry: LCMS
  mass spectrometry: MS
  polytetrafluoroethylene: PTFE
  hour: h
  minute: min
  retention time: tR
  ethyl: Et
  methyl: Me
  benzyl: Bn
  lithium diisopropylamide: LDA
  1-(3-dimethylaminopropyl)-3-ethyl carbodiimide hydrochloride: EDCI
  DIEA means N,N-diisopropylethylamine
  ethyl acetate: EtOAc
  N,N-dimethylformamide: DMF
  methanol: MeOH
  Ethanol: EtOH
  acetonitrile: $CH_3CN$
  acetic acid: AcOH
  magnesium sulfate: $MgSO_4$
  copper iodide: CuI
  diisopropylamine: $iPr_2NH$
  Dichlorobis(triphenylphosphine)palladium: $PdCl_2(PPh_3)_2$
  ammonium hydroxide: $NH_4OH$
  trifluoroacetic acid: TFA
  benzyloxycarbonyl: Cbz
  tert-butoxycarbonyl: Boc
  DCM: Dichloromethane
  $TMSCHN_2$: Trimethylsilyldiazomethane
  Teoc-OSu: O-Trimethylsilylethoxycarbonyl N-hydroxylsuccinate
  TBAF: Tetrabutylammonium Flouride
  THF: Tetrahydrofurane MCPBA: meta-Chloroperbenzoic acid
TsOH: Toluenesulfonic acid.
PhIO: iodosobenzene
Pb(OAc)$_4$: Lead tetra-acetate Method A, Step 3, A literature procedure is adapted (Tetrahedron Letters 2003). To a mixture of A4 in CCl$_4$/Acetonitrile/H$_2$O (5/5/1) is added RuCl$_3$ (0.1 eq), NaIO$_4$ (10 eq) and NaHCO$_3$ (10 eq) and

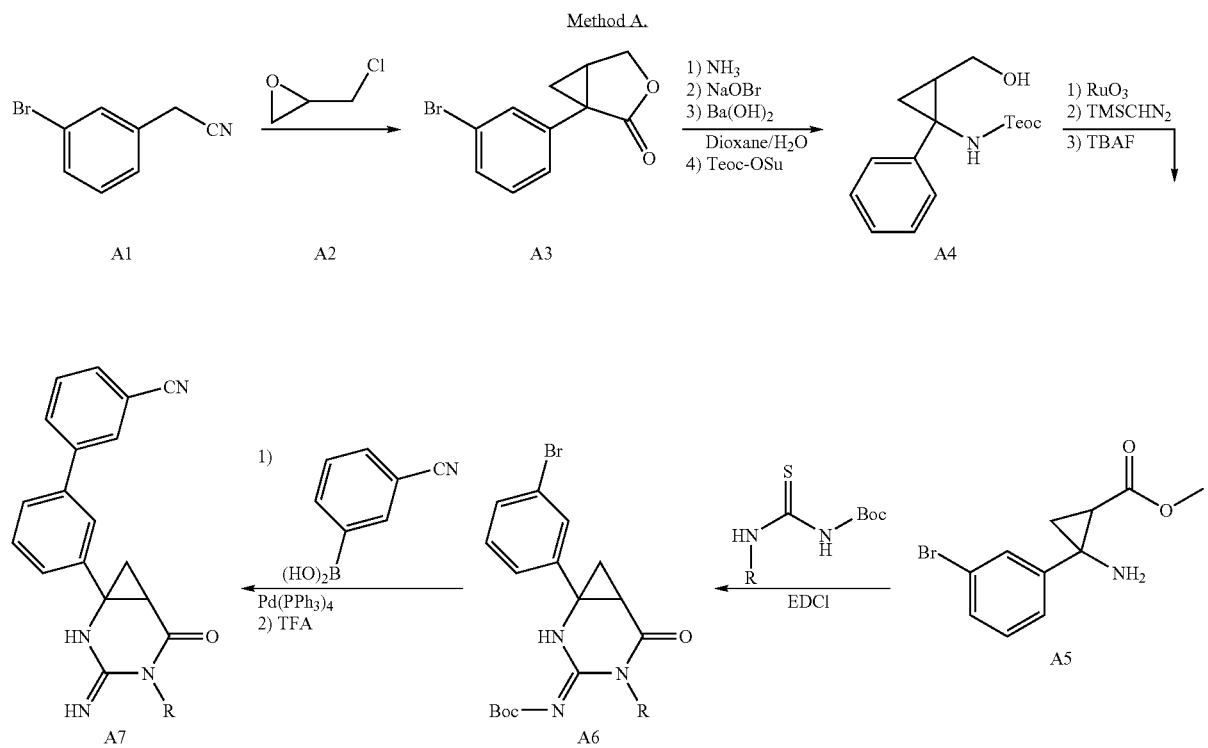

Method A, Step 1

A literature procedure is adapted (Y. Kazuta, et. al. Bioorganic & Medicinal Chemistry, 10 (2002), 3829-3848). Thus, to a suspension of NaNH$_2$ (22.0 mmol) in benzene (20 mL) is added a solution of 3-bromophenylacetonitrile (10 mmol) in benzene (10 ml) at 0° C., and the reaction is stirred at r.t. for 2 h. After the solvent is evaporated the residue is chromatographed to give product A3.

Method A, Step 2

A similar literature procedure is adapted (Casadio, S. et. al. Bollettino Chimico Farmaceutico (1978), 117(6), 331-42). Compound A3 is dissolved in 7N NH$_3$/MeOH and the solution is heated in a sealed tube to 70 0° C. for 1 h. before the solvent is evaporated. The result amide (10 mmol) redissolved in MeOH is treated with aq NaOBr (5 eq) overnight before the reaction mixture is partitioned between DCM/water. The organic layer is washed with brine and dried with Na$_2$SO$_4$ and evaporated to give the crude cyclic carbamate which is hydrolyzed with Ba(OH)$_2$ in dioxane/water under heat overnight to give the aminoalcohol. The solution is cooled to r.t. and its pH is adjusted to 9 using aq NaHSO$_4$ before TEOC-OSu (1.1 eq) is added. The reaction is stirred for 5 h before the solution is partitioned between DCM/water. The organic solution is washed with brine and dried over Na$_2$SO$_4$ and subsequently evaporated to give crude product which is purified via a silica gel column to compound A4.

the reaction is stirred overnight before the mixture is acidified to pH 3 and partitioned in DCM/water. The organic layer is dried and solvent evaporated to give the amino acid product which is dissolved in MeOH and treated with TMSCHN$_2$ to give the corresponding amino ester after evaporation of the solvent. The amino ester is treated with 1 N TBAF in THF for 20 min before the reaction mixture is diluted with Ether and filtered through a silica gel pad to give the amino ester product A5.

Method A, Step 4,

To a DMF solution of A5 is added N-methyl-N'-Boc-thiourea (1 eq) followed by addition of EDCI (1 eq) and DIEA (2 eq) and the solution is stirred overnight. The solvent is evaporated under vacuum and residue chromatographed to give the boc-ed iminopyrimidinone A6.

Method A, Step 5.

A mixture of compound A6, 3-cyanophenylboronic acid, Fibrecat (4.26% of Pd, 0.7 g) and 1 N aq. K$_2$CO$_3$ (0.5 mL) in tert-butanol (10 mL) is heated at 110° C. for 15 min. After cooling, the reaction mixture is transferred to a pre-packed Si-Carbonate column and eluted with MeOH/CH$_2$Cl$_2$ (1:1). The eluant is collected and concentrated under reduced pressure to give a crude product which is purified by silica gel chromatography (20-50% EtOAc/hexanes gradient) to yield the product. After treatment of the product with 30% TFA in DCM for 20 min followed by evaporation of solvent, product A7 is obtained.

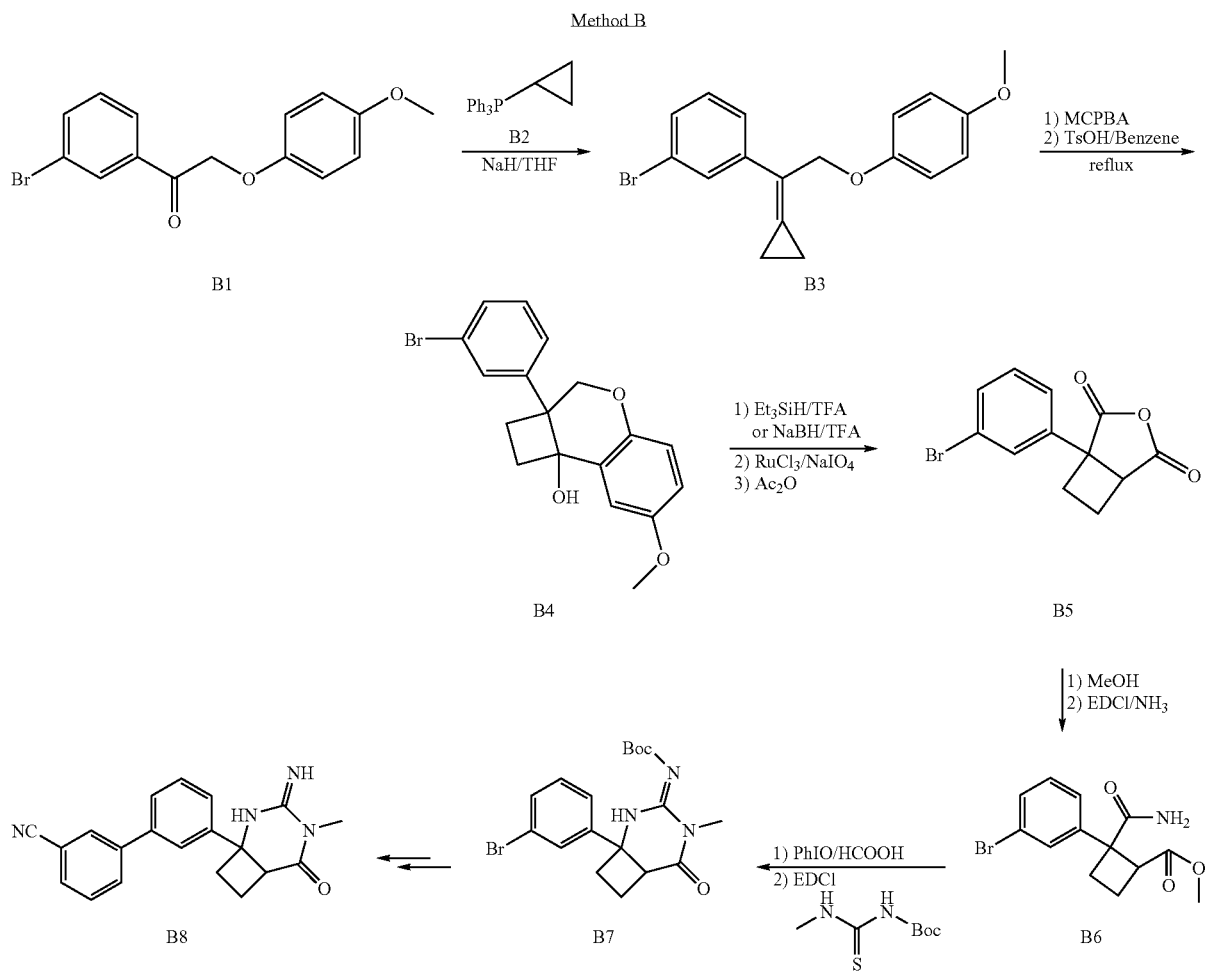

Method B, Step 1:

A literature procedure is adapted (Bernard, A. et. al Tetrahedron (2004), 60(2), 449-457). Compound B1 (1 g) and B2 (1.1 eq) in anhydrous THF is treated with NaH (1.5 eq) and the mixture is stirred at r.t. overnight. After evaporation of solvent the residue is purified via silica gel column to give compound B3.

Method B, Step 2:

A mixture of compound B3 (1 g), MCPBA (2 eq) and NaHCO$_3$ (5 eq) is stirred overnight before it is diluted with DCM and washed with aq NaHCO$_3$, brine and dried. The solvent is evaporated to give a crude epoxide. This crude product is dissolved in anhydrous benzene and 100 mg of p-toluenesulfonic acid is added. The reaction is refluxed overnight before it is cooled to r.t., washed with aq NaHCO$_3$ and concentrated to give product B4.

Method B, Step 3;

A solution of B4 (1 g) in 20% TFA in DCM is treated with triethylsilane (3 eq) or with NaBH$_4$. After removal of the volatiles, the residue is chromatographed to give a product which is dissolved in a mixture of CCl$_4$/Acetonitrile/water (5/5/1) and RuCl$_3$ (0.1 eq)/NaIO$_4$ (10 eq). The reaction mixture is stirred over night before the solid is filtered and the liquid mixture is concentrated. The residue is stirred with 10 ml acetic anhydride for 30 min before the volatile is evaporated to give a crude product B5.

Method B, Step 4.

The crude product anhydride is redissolved in MeOH. The reaction is refluxed for 1 h and solvent evaporated. The residue is redissolved in DMF followed by addition of NH$_4$Cl (5 eq) and EDCI hydrochloric salt (1.5 eq) and DIEA (5 eq). The reaction mixture is stirred overnight before it is partitioned in DCM/Water. The organic layer is dried, solvent evaporated and the residue is chromatographed to give the primary amide B6.

Method B, Step 5.

To a solution of B6 in acetonitrile/water/formic acid (3/1/6) is added PhIO (2 eq) and the mixture is stirred overnight before said mixture is made basic (pH 10) using aq Na$_2$CO$_3$ and partitioned between DCM and water. The organic layer is dried and solvent evaporated. The residue is redissolved in DMF and EDCI (1.1 eq), N-methyl-N'-Boc-thiourea (1.1 eq) and DIEA (2 eq) is added. The reaction is stirred overnight before it is partitioned between DCM and water. The organic layer is washed with brine and dried over Na$_2$SO$_4$ and solvent evaporated. The residue is purified with a silica gel column to give product B7.

Method B, Step 6

Product B8 is obtained using method similar to Method A step 5.

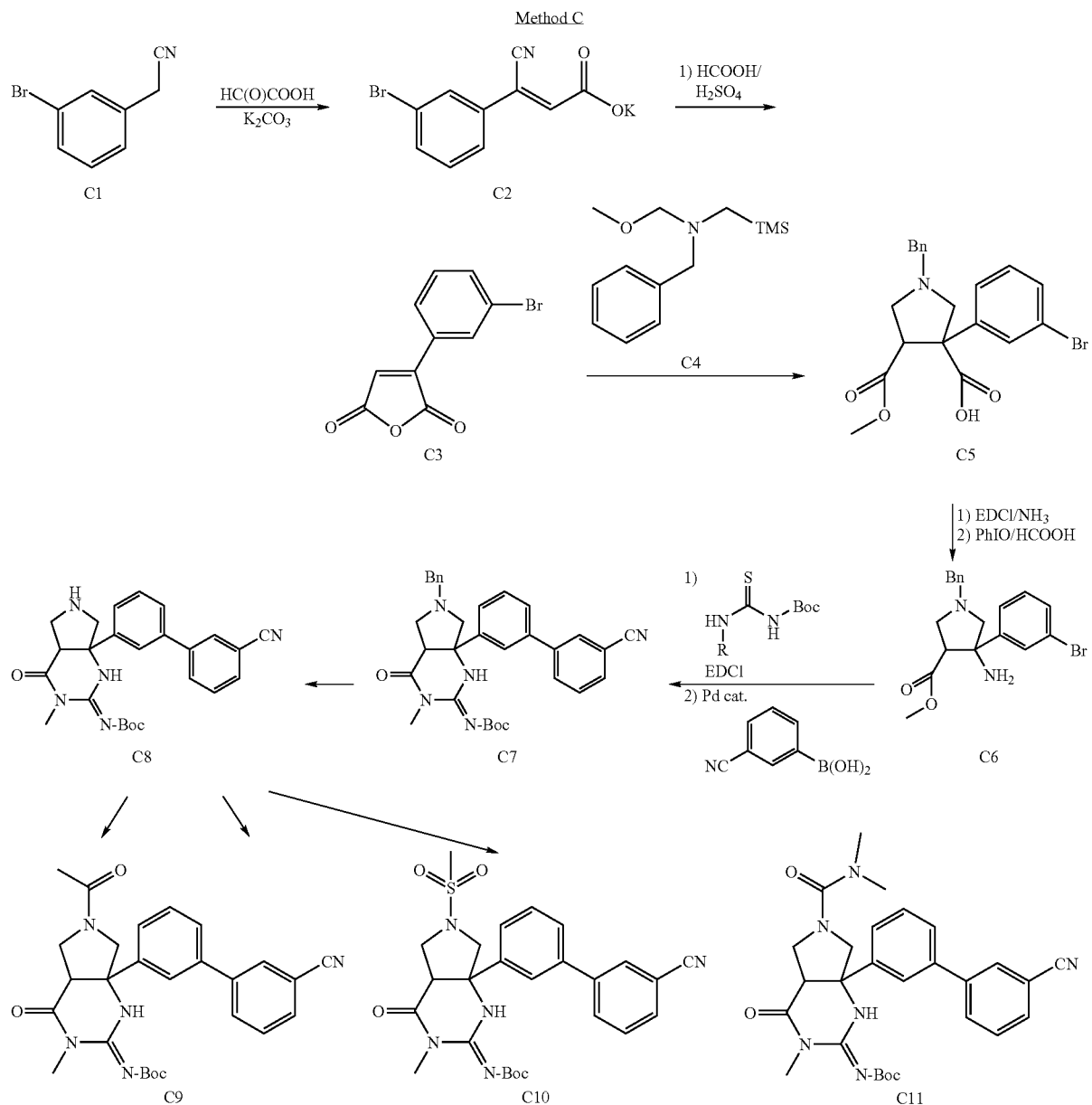

Method C, Step 1.

A literature procedure is adapted (JOC, 1993, (58), 7916). To a solution of 36 g of m-bromophenylacetonitrile and glyoxaldehyde (44.4 m l 50% aq solution) in 350 ml of MeOH is added 63 g (2.5 eq) of $K_2CO_3$ and the reaction mixture is stirred at r.t. for 4 h. The solid is filtered and washed with ether before it is resuspended in cold water and stirred vigorously for 1 h. The white solid is filtered to give crude product C2.

Method C, Step 2;

The crude product C2 (50 g) is dissolved in 400 ml of formic acid and 40 ml conc. sulfuric acid and the solution is refluxed overnight. After the reaction is cooled down, the mixture is poured into ice water and the solid filtered to give product C3.

Method C, Step 3;

To a solution of C3 (0.27 g) and C4 (1.0 eq) in 3 ml of anhydrous DCM is added 0.5 of TFA and the solution is stirred at r.t. overnight. After removal of solvent, the residue is purified using a reverse phase C-18 column to give product C5.

Method C, Step 4.

Compound C6 is obtained using a procedure similar to Method B, step 5

Method C. Step 5.

Product C7 is obtained using procedure similar to Method A step 4,5.

Method C, Step 6

Compound C8 is obtained through debenzylation of C7 under Pd hydrogenation conditions.

Method C, Step 7,8,9

Conventional amide, sulfonamide and urea formation conditions are used for compound C9, C10 and C11.

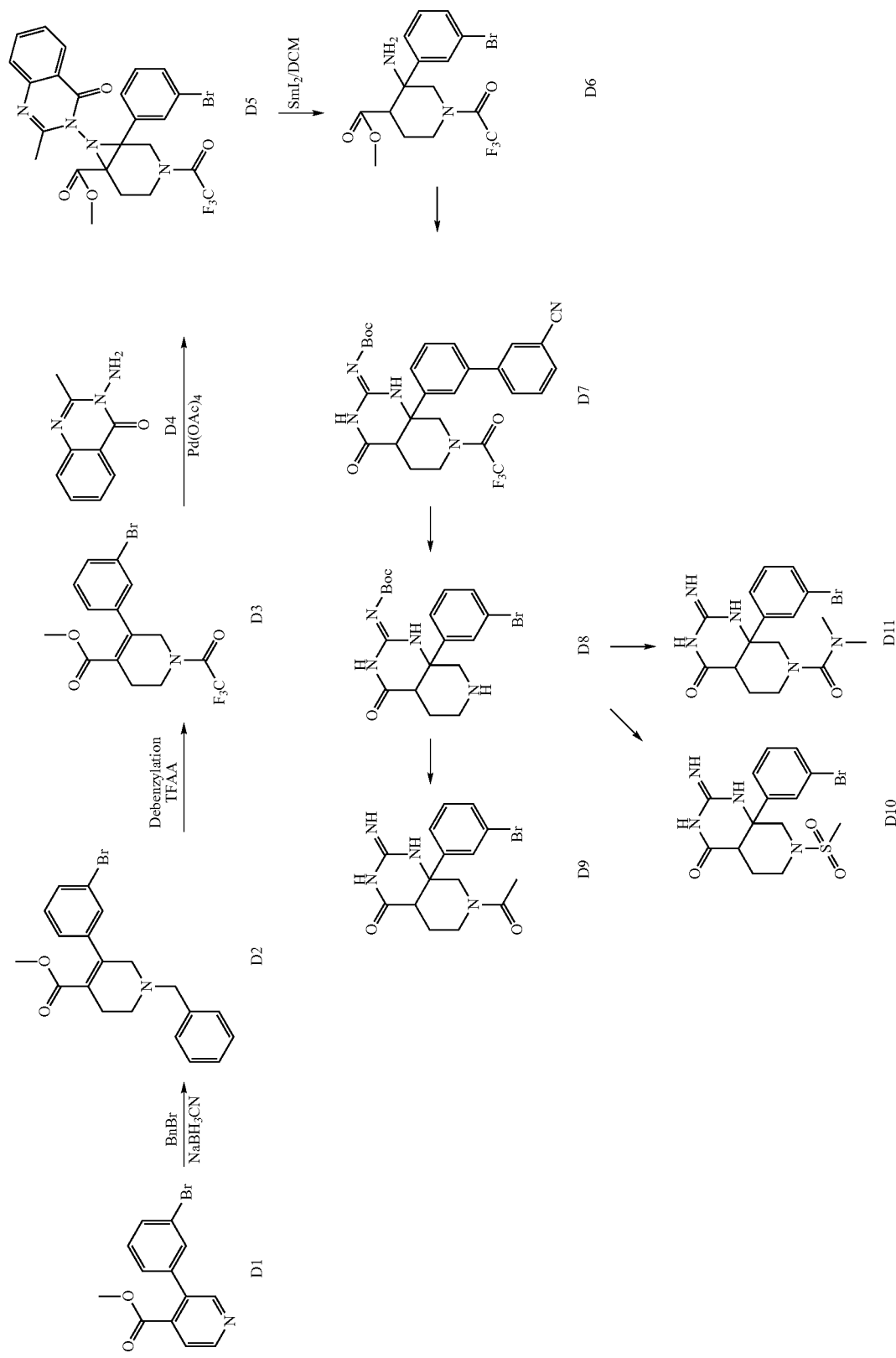

Method D, Step 1

A literature procedure is used for generation of compound D2 and D3 (Gwaltney, S. et. al Bioorganic & Medicinal Chemistry Letters (2003), 13(7), 1359-1362). 3-m-bromophenylisonicotinic acid methyl ester (D1) is treated with BnBr in DCM for 3 h at 50° C. before it is cooled to r.t. and NaBH$_3$CN (6 eq) is added. The reaction is stirred overnight before it is diluted with DCM and washed with water and brine. The residue after removal of organic solvent is purified via a silica gel column to afford D2.

Method D, Step 2.

Compound D2 is treated with 1-Chloroethylchloroformate in DCM for 2 h at r.t. before it is quenched with MeOH. After dilution with DCM, the reaction mixture is washed with aq Na$_2$CO$_3$. The organic layer is dried and solvent evaporated to give a crude product which is treated with Trifluroacetic anhydride (2 eq) and TEA (2 ea) in DCM. The reaction is stirred for 1 h before it is quenched with water and the DCM solution is dried and concentrated to give compound D3 after purification.

Method D, Step 3

A literature procedure is adapted (Selective aziridination of olefinic esters. Deshmukh, M.; Chavan, P.; Kharade, D Monatshefte fuer Chemie (1994), 125(6-7), 743-6). To a DCM solution of D3 and D4 (1.2 eq) is added Lead tetraacetate (2 eq) and the reaction is stirred overnight before it is diluted with DCM and washed with aq NaHCO$_3$, brine. The DCM layer is dried and solvent evaporated. The residue is chromatographed to give compound D5.

Method D, Step 4

A literature procedure is adapted (Atkinson, R et. al. Tetrahedron Letters (2002), 43(11), 2083-2085). To a THF solution of D5 is added SmI2 in THF (4 eq) before the reaction is quenched with water and reaction is adjusted to pH 9. The reaction mixture is partitioned between DCM and water. The organic solution is dried and solvent evaporated to give crude product D6.

Method D, Step 5.

Product D7 is obtained using a procedure similar to Method A Step 4 followed by Method Step 5 for the Suzuki coupling.

Method D, Step 6,

Compound D8 is obtained by treatment of D7 with 2N ammonia in MeOH.

Method D, Step 7, 8 and 9

Conventional amide, sulfonamide and urea formation procedures are used for generation of D9, D10 and D11 after TFA deprotection of the Boc group.

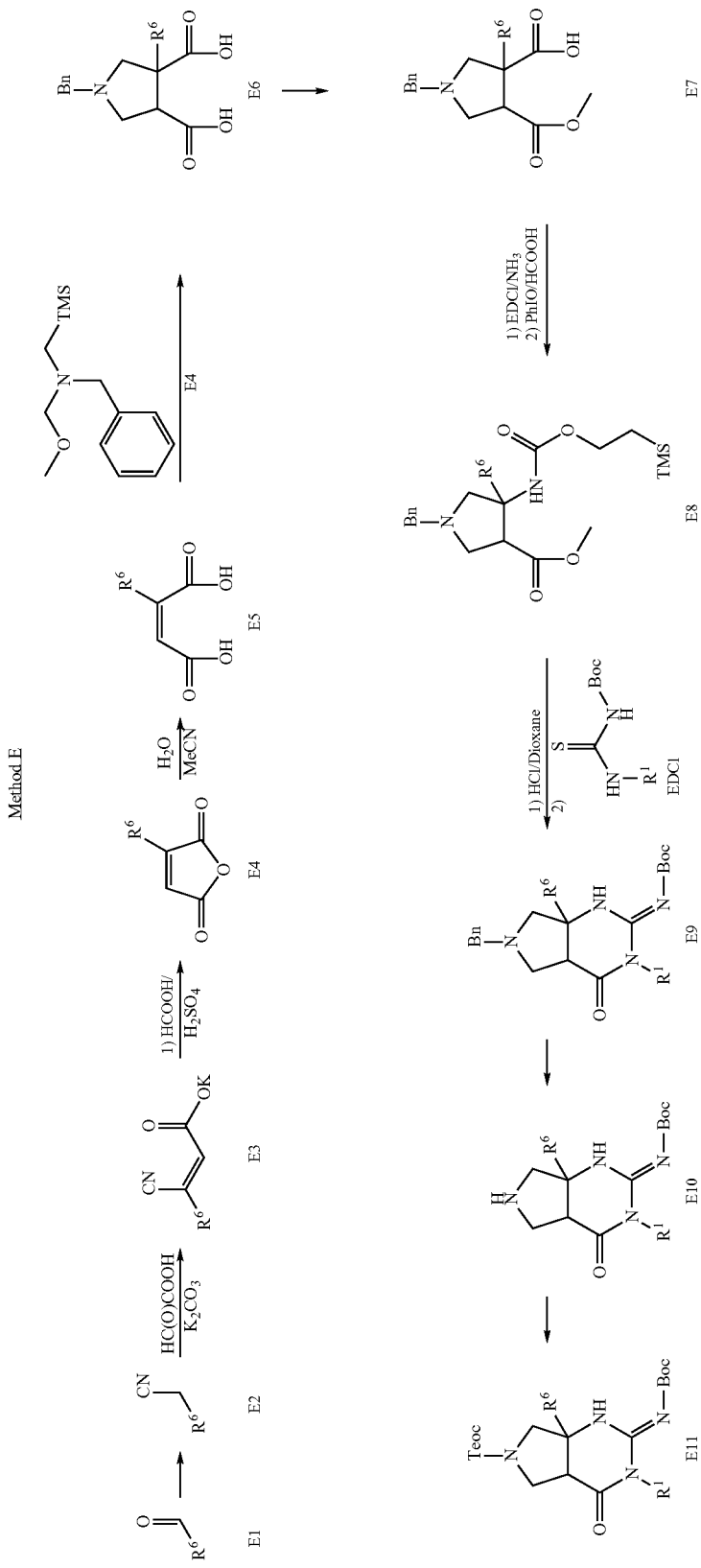

Method E, Step 1.

To a solution of aldehyde E1 ($R^6$=4-Bromothien-2-yl, 20 g) in 100 mL methanol was added 4 g of $NaBH_4$ at 0° C. and the resulting solution was stirred until the reaction was completed at 0° C. To the reaction was quenched with water (100 mL) before the solvent was evaporated. The residue was extracted with ethyl acetate/water, and the organic layers were combined and washed with brine, dried with $MgSO_4$, evaporated to provide a alcohol which was used without further purification.

NMR($H^1$, $CDCl_3$) of product alcohol ($R^6$=4-Bromothien-2-yl): δ 7.17, s, 1H; 6.93 s, 1H; 4.80, d (J=6.0 Hz), 2H; 1.84, t (J=6.0 Hz), 1H.

To a solution of the above alcohol in 10 mL $CH_2Cl_2$ was added 1.2 equiv. of $SOCl_2$ at 0° C. The resulting reaction mixture was stirred at 0° C. for 30 min and at rt for 2 h. The reaction mixture was extracted with ethyl acetate/water and the organic layers were washed with brine, dried with MgSO4 and evaporated to yield a chloride.

NMR($H^1$, $CDCl_3$) of product chloride ($R^6$=4-Bromothien-2-yl): δ 7.15-7.30, m, 2H; 4.73, s, 2H.

To the chloride (4.4 g, 21 mmol) in 50 mL of AcCN was added KCN (3.6 equiv, 5 gm, 76 mmol) and the resulting reaction mixture was stirred at rt for 1 hr before it was heated under reflux until the disappearance of starting. The reaction mixture was diluted with ethyl acetate, filtered and the solid was washed with ethyl acetate. The combined filtrate was washed with water, brine, dried and concentrated. The residue was chromatographed using ethyl acetate/hexane to give product E2 ($R^6$=4-Bromothien-2-yl, 75%).

NMR ($H^1$, $CDCl_3$) of E2 ($R^6$=4-Bromothien-2-yl): δ 7.18, s, 1H; 7.00, s, 1H, 3.89, s, 2H.

Method E, Step 2;

A literature procedure was adapted (JOC, 1993, (58), 7916). To a solution of 4 g of E2 ($R^6$=4-Bromothien-2-yl) and glyoxaldehyde (1.5 eq, 50% aq solution) in 50 ml of MeOH was added 6.9 g (2.5 eq) of $K_2CO_3$ and the reaction mixture was stirred at r.t. for 4 h. The solid was filtered and washed with ether before it was resuspended in cold water and stirred vigorously for 1 h. The white solid is filtered and dried to give crude product E3 ($R^6$=4-Bromothien-2-yl) which was used without further purification. A small quantity of E3 was extracted with EtOAc/1N HCl and the organic solution was evaporated to give the corresponding free acid of E3 ($R^6$=4-Bromothien-2-yl).

NMR($H^1$, $CDCl_3$) of E3 ($R^6$=4-Bromothien-2-yl) as a free acid: δ 7.69, s, 1H; 7.56, s, 1H; 6.96, s, 1H.

Method E, Step 3;

The crude product E3 ($R^6$=4-Bromothien-2-yl) (50 g) was dissolved in 400 ml of formic acid and 40 ml conc. sulfuric acid. The solution was refluxed for 2 h. before it was cooled down to rt. The solution was poured into ice water and the solid filtered to give product E4 ($R^6$=4-Bromothien-2-yl) (80%).

NMR($H^1$, $CDCl_3$) of E4 ($R^6$=4-Bromothien-2-yl): δ 7.88, s, 1H; 7.84, s, 1H; 7.09, s, 1H.

Method E, Step 4;

A solution of E4 ($R^6$=4-Bromothien-2-yl) (27 g) in 300 ml mixture of acetonitril and water (10%) was heated at 40° C. until the starting material disappeared. The reaction solution was concentrated and the residue dried in vaccuo to give compound E5 ($R^6$=4-Bromothien-2-yl) in quantitative yield.

NMR($H^1$, $CDCl_3$) of E4 ($R^6$=4-Bromothien-2-yl): δ 7.66, s, 1H; 7.40, s, 1H; 6.42, s, 1H.

Method E, Step 5.

To solution of E5 ($R^6$=4-Bromothien-2-yl) (5 g, 18.17 mmol) in 72 mL anhydrous THF was added E4 (2.0 equiv. 6 mL) at 0° C. and the resulting solution was stirred at 0° C. for 90 min. before the reaction was quenched with 10 mL 1N HCl at 0° C. and the reaction mixture was extracted with ethyl acetate and the organic layers were combined, dried with anhydrous $Na_2SO_4$, then concentrated to yield 6 g of E6 ($R^6$=4-Bromothien-2-yl), which was used for next step without further purification.

NMR($H^1$, $CD_3O$ D) of E6 ($R^6$=4-Bromothien-2-yl): δ 7.45-7.60, m, 7H; 4.49, m, 2H; 4.30, d (J=12 Hz), 1H; 3.8-4.0, m, 4H.

Method E, Step 6.

To a oven-dried flask containing E6 ($R^6$=4-Bromothien-2-yl) (6 g) was added acetic anhydride (100 mL) at rt. The resulting solution was heated for 30 min at 90° C. before the reaction mixture was cooled to rt, poured into a flask containing 500 mL methanol at 0° C. and the solution was evaporated to dryness. The crude product was dissolved in 200 mL $CH_2Cl_2$, washed with 1H HCl, brine, dried with $Na_2SO_4$ and concentrated to obtain 6 g of product E7 ($R^6$=4-Bromothien-2-yl) as a HCl salt (yield 96%) which was taken for next step without purification.

NMR($H^1$, $CDCl_3$) of E7 ($R^6$=4-Bromothien-2-yl): δ 7.10-7.60, m, 7H; 4.3, m, 2H; 4.12, d (J=12 Hz), 1H; 3.7-3.9, m, 4H; 3.6, s, 3H.

Method E. Step 7.

To an oven-dried flask containing Compound E7 ($R^6$=4-Bromothien-2-yl) (4.67 gm) in 10 mL toluene was added DPPA (2 equiv, 14.18 mmol, 3 mL) followed by triethyl amine (2.2 equiv, 2.16 mL) at 0° C. before the mixture was stirred at rt overnight. To the reaction mixture was added trimethylsilylethanol (4 equiv. 4 mL) and the reaction mixture was refluxed for 1 hr before it was cooled to rt, diluted with ethyl acetate (150 mL), washed with brine, water, dried with $Na_2SO_4$ and concentrated. The crude product was chromatographed using a silica gel column eluted with (30% ethyl acetate in hexanes) to obtain 1.5 g of E8 ($R^6$=4-Bromothien-2-yl) (40%)

NMR($H^1$, $CDCl_3$) of E8 ($R^6$=4-Bromothien-2-yl): δ 7.20-7.40, m, 5H; 7.07, d (J=1.5 Hz), 1H; 6.94, d (J=1.5 Hz), 1H; 4.11, m, 2H; 3.79, AB (J=11 Hz), 1H; 3.70, s, 3H; 3.69, AB (J=11 Hz), 1H; 3.54, AB (J=10 Hz), 1H; 3.32, t (J=8 Hz), 1 H; 3.21, AB (J=10 Hz), 1H; 3.16, t (J=8 Hz), 1H; 2.88, t (J=8 Hz), 1H; 0.97, m, 2H; 0.03, s, 9H.

Method E. Step 8.

To a solution of 35.2 g of E8 ($R^6$=4-Bromothien-2-yl) in 200 ml dioxane was added 20 ml of 4N HCl in dioxane at 0 C and the solution was allowed to warm to rt over 14 h before ether (400 ml) was added. The white precipitate was collected and washed with 200 ml of ether, dried in a vacuum oven overnight to give 36.7 g of a HCl salt, which was used without further purification.

NMR($H^1$, $CDCl_3$) of the product amine HCl salt ($R^6$=4-Bromothien-2-yl): δ 7.17, d (J=1.5 Hz), 1H; 6.86, d (J=6.86 Hz), 1H; 3.65-2.71, m, 1H; 3.45-3.31, m, 6H; 3.29, s, 3H.

To a DMF solution (300 ml) of the HCl salt (76 mmol) was added DIEA (5 eq), and N-methyl-N'-Boc-thiourea (1 eq) followed by addition of EDCI.HCl (1.05 eq) and the solution was stirred at rt for 48 h before it was extracted with EtOAc/water. After removal of organic solvent, the residue was chromatographed via a silica gel column to give product E11 ($R^6$=4-thien-2-yl, $R^1$=Me).

NMR(H¹, CDCl₃) for E11 (R⁶=4-thien-2-yl, R¹=Me): δ 7.25-7.34, m, 5 H; 7.15, d (J=1.5 Hz), 1H; 6.91, d (J=1.5 Hz), 1H; 3.75, m, 2H; 3.42, m, 1H; 3.34, m, 1H; 3.31, S, 3H; 3.22, AB (J=10 Hz), 1H; 3.09, AB (J=10 Hz), 1H; 3.02, M, 1H; 1.54, S, 9H.

Method E. Step 9

To a mixture of DCM solution (10 ml) of E11 (R⁶=4-thien-2-yl, R¹=Me; 1 g) and potassium carbonate (300 mg) was added 1-chloroethylchloroformate at −15° C. and the solution was stirred for 1.5 h at r.t. before the mixture was filtered followed by evaporation of the solvent. The residue was redissolved in 10 ml methanol and the reaction left overnight. After removal of methanol in vaccuo, the residue was chromatographed to give E12 as a solid (R⁶=4-thien-2-yl, R¹=Me; 70% yield).

NMR(H¹, CDCl₃) for E12 (R⁶=4-thien-2-yl, R¹=Me): δ 10.30, br, s, 1H; 7.17, d (J=1.5 Hz), 1H; 6.86, d (J=1.5 Hz), 1H; 3.68, m, 1H; 3.42, d(J=12 Hz), 1H, 3.31-3.40, m, 3H, 3.29, s, 3H; 1.52, s, 9H.

Method E. Step 10

To a solution of 13 g of E12 (R⁶=4-thien-2-yl, R¹=Me) in 100 ml DCM was added Teoc-OSu (1.03 eq) and DIEA (1.1 eq) at 0° C. The reaction was stirred until disappearance of E12 (R⁶=4-thien-2-yl, R¹=Me) before it was extracted with EtOAc/water. The organic layer was dried and solvent evaporated and the residue chromatographed to give E13 (R⁶=4-thien-2-yl, R¹=Me) as an oil.

NMR(H¹, CDCl₃) for E13 (R⁶=4-thien-2-yl, R¹=Me): δ 10.40, br, m, 1H; 7.22, br. s, 1H; 6.90, 1H; 4.20, m, 2H; 3.68-4.06, m, 4H; 3.47, m, 1H; 3.30, s, 3H; 1.29, s, 9H; 1.01, m, 2H; 0.03, s, 9H.

E13 (R⁶=4-thien-2-yl, R¹=Me) was resolved using a semi-prep ChiralPak AS column eluted with 50% isopropanol in hexane (50 ml/min): t=19.3 min, enantiomer I, E19 (R⁶=4-thien-2-yl, R¹=Me), [D]=−94° mL g⁻¹ dm⁻¹ (MeOH, C=1, 23° C.); t=39.5 min, enantiomer II, E20 (R⁶=4-thien-2-yl, R¹=Me), [D]=+105° mL g⁻¹ dm⁻¹ (MeOH, C=1, 23° C.).

The following compounds were produced using similar methods:

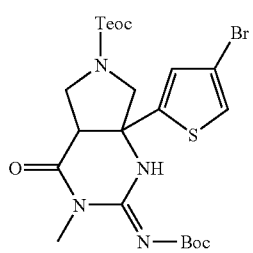

E14

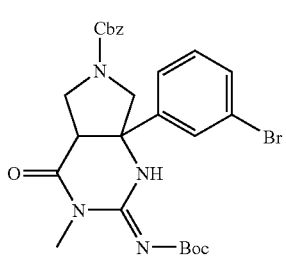

E15

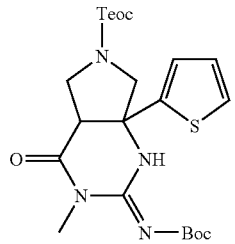

E16

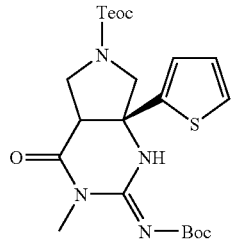

E17

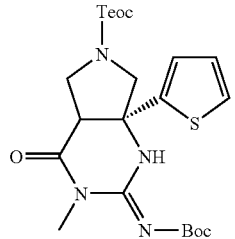

E18

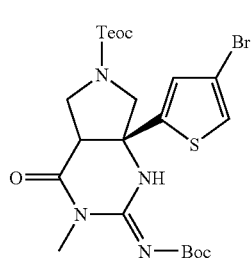

E19

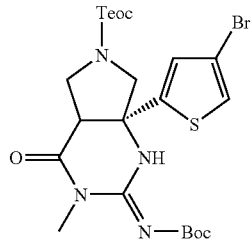

E20

The following compounds were generated using method similar to Method E followed by deprotection of Boc using 20% TFA in DCM.

| Structure | Obs. Mass | Structure | Obs. Mass |
|---|---|---|---|
| 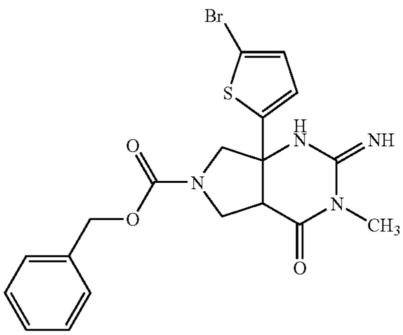 | 463.25 | 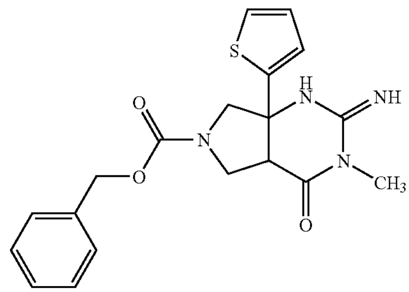 | 385.21 |
| 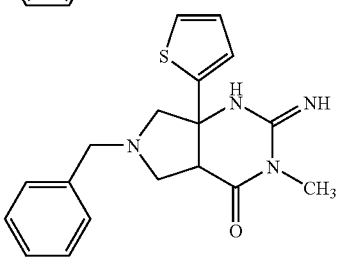 | 341.19 | 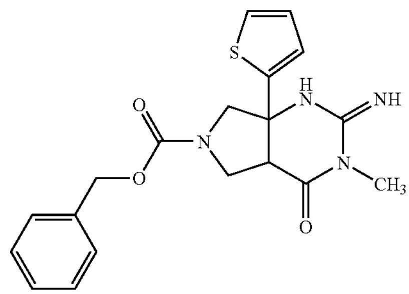 | 385.21 |
| 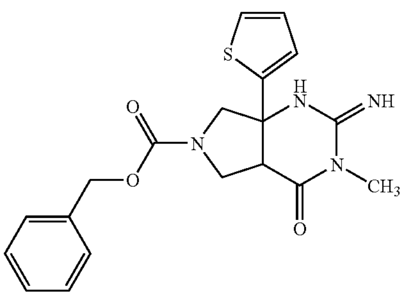 | 385.21 | | |
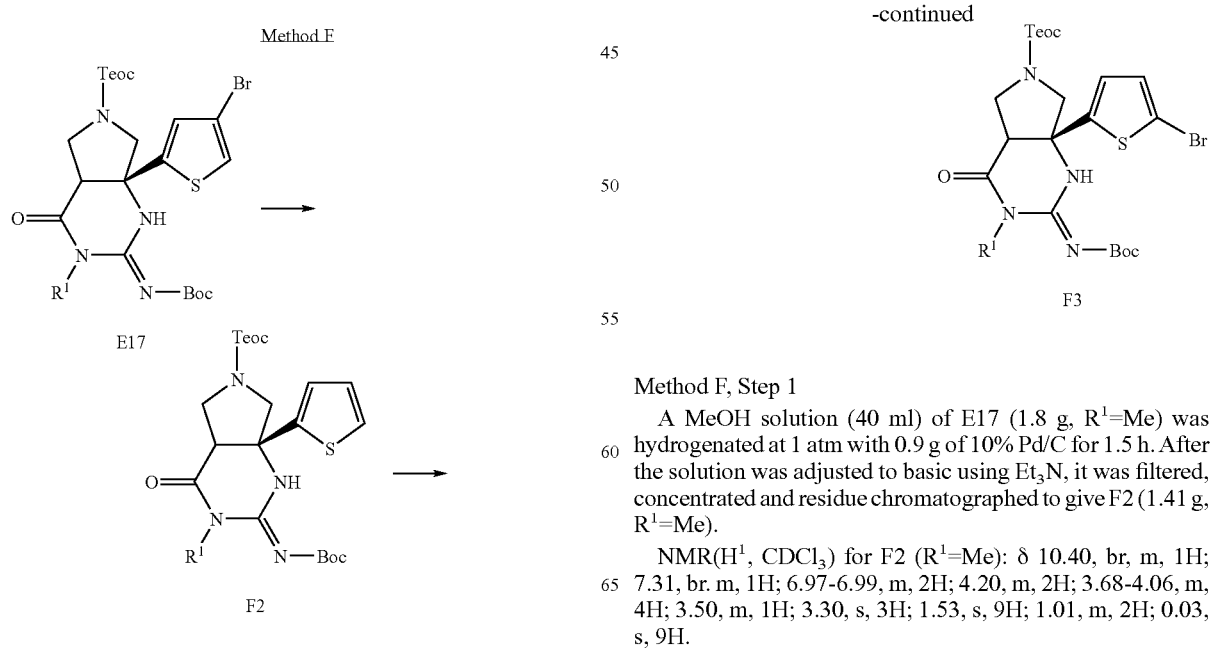
Method F, Step 1
A MeOH solution (40 ml) of E17 (1.8 g, $R^1$=Me) was hydrogenated at 1 atm with 0.9 g of 10% Pd/C for 1.5 h. After the solution was adjusted to basic using $Et_3N$, it was filtered, concentrated and residue chromatographed to give F2 (1.41 g, $R^1$=Me).
NMR($H^1$, $CDCl_3$) for F2 ($R^1$=Me): δ 10.40, br, m, 1H; 7.31, br. m, 1H; 6.97-6.99, m, 2H; 4.20, m, 2H; 3.68-4.06, m, 4H; 3.50, m, 1H; 3.30, s, 3H; 1.53, s, 9H; 1.01, m, 2H; 0.03, s, 9H.

Method F, Step 2

A DMF solution (15 ml) of F2 (1.41 g, $R^1$=Me) was treated with NBS (1.2 eq) and the reaction was stirred overnight before it was extracted using EtOAc/water. The organic solution was evaporated and the residue chromatographed to give F3 ($R^1$=Me).

NMR($H^1$, CDCl$_3$) for F3 ($R^1$=Me): δ 10.39, br, m, 1H; 6.94, d (J=4 Hz), 1H; 6.76, m, 1H; 4.20, m, 2H; 3.68-4.04, m, 4H; 3.43, m, 1H; 3.29, s, 3H; 1.53, s, 9H; 1.01, m, 2H; 0.03, s, 9H.

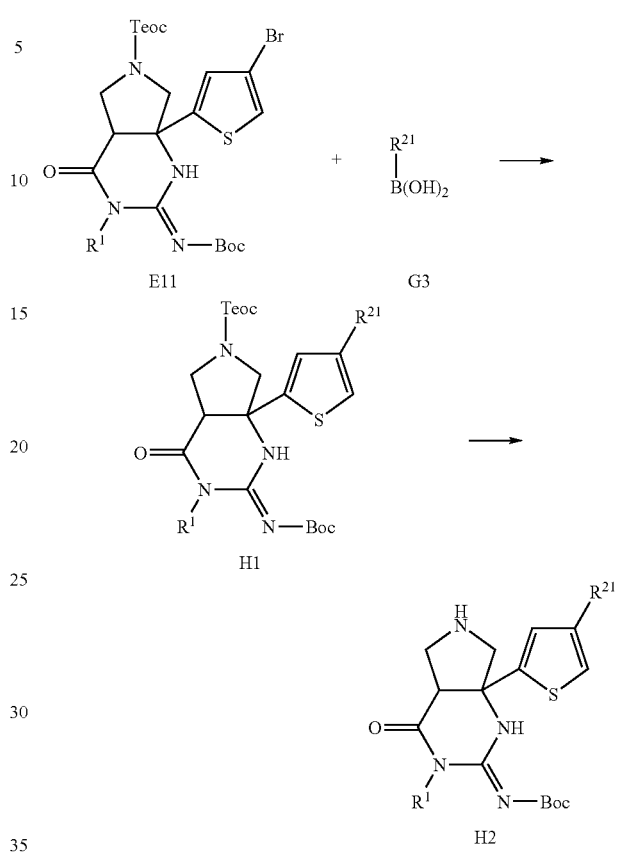

Method G, Step 1;

A mixture of G1 (2.5 g), CuI (0.3 eq), palladium tetrakistriphenylphosphine (0.05 eq), TBAF (1 N in THF, 1 eq), TMS-propyne (1 eq) and triethylamine (3.3 eq) in 400 mL of toluene was stirred at rt for 3 h before it was extracted with DCM and water. The organic layer was dried, evaporated and the residue chromatographed to give compound G2 in 68% yield.

NMR($H^1$, CDCl$_3$) for G2: δ 8.54, m, 1H; 8.51, m, 1H; 7.81, m, 1H; 2.08, s, 3H.

Method G. Step 2;

To A 1000 mL flame dried flask charged with anhydrous toluene (1.6 mL/mmol, 188 mL) and anhydrous THF (0.4 mL/mmol 47 mL) under nitrogen was added triisopropyl borate (32 mL, 141.36 mmol, 1.2 equiv.) and 3-bromo-3-propynylpyridine (23 gm, 117.8 mmol). The mixture was cooled to –40° C. followed by addition of n-Butyllithium (2.5 M in hexanes, 56 mL, 141.36 mmol) via a syringe pump over 1 hr. The mixture was stirred for an additional 0.5 hr while the temperature was held at –40° C. before it was warmed to –20° C. followed by addition of 2 N aq. HCl (120 mL). After removal of the organic layer, the pH of the aqueous phase was adjusted to pH7 using a 5 N NaOH solution. A white solid product precipitated as the pH approached 7. The aq. mixture was then saturated with NaCl using solid NaCl, and extracted three times with THF (150 mL). The combined THF extracts were evaporated in vacuo to provide a solid, (18 gm, 95% yield).

NMR($H^1$, CDCl$_3$) for G3: δ 8.67, s, 1H; 8.48, s, 1H; 8.09, s, 1H; 2.06, s, 3H.

Method H, Step 1,

To a solution of bromide E11 (1 g, 1.74 mmol, $R^1$=Me) and boronic acid G3 (1.5 eq, $R^{21}$=m-propynylpyridin-3-yl) in 7 mL tBuOH was added dichloro[1,1'-bis(diphenylphosphino)-ferrocene]palladium(II) dichloromethane (0.15 eq) followed by aqueous $K_2CO_3$ (1N, 1.5 equiv.). The resulting mixture was heated at 60° C. for 1 h before it was cooled, diluted with ethyl acetate and washed with water. The organic layer was dried, concentrated and the residue was chromatographed using a silica gel column eluted with ethyl acetate in hexanes to give H1 ($R^1$=Me, $R^{21}$=m-propynylpyridin-3-yl; Yield 90%).

NMR($H^1$, CDCl$_3$) for H1 ($R^1$=Me, $R^{21}$=m-propynylpyridin-3-yl): δ 10.45, br. 1H; 8.63, br. s, 1H; 8.53, br. s, 1H; 7.76, br s, 1H; 7.46, br s, 1H; 7.20, m, 1H; 4.20, m, 2H; 3.90-4.13, m, 3H; 3.74, m, 1H; 3.73, m, 1H; 3.31, s, 3H; 2.08, s, 3H; 1.53, s, 9H; 1.01, m, 2H; 0.03, s, 9H.

Method H, Step 2,

Into a 25 mL flask containing H1 (1 gm, 1.64 mmol, $R^1$=Me, $R^{21}$=m-propynylpyridin-3-yl) was added 5 mL of 1 M TBAF in THF at 0° C. and the solution was stirred at rt for 4 h. The reaction mixture was poured into saturated solution of NaHCO$_3$, extracted with ethyl acetate. The organic layer was concentrated and residue purified with 2% MeOH/CH$_2$Cl$_2$ to give H2 ($R^1$=Me, $R^{21}$=m-propynylpyridin-3-yl) in 70% yield.

NMR($H^1$, CDCl$_3$) for H2 ($R^1$=Me, $R^{21}$=m-propynylpyridin-3-yl): 810.36, s, 1H; 8.65, s, 1H; 8.53, s, 1H; 7.77, s, 1H; 7.43, br s, 1H; 7.18, m, 1H; 3.73, m, 1H; 3.49, m, 2H; 3.40, m, 2H; 3.32, s, 3H; 2.09, s, 3H; 1.54, s, 9H.

The following compounds were generated using similar method:
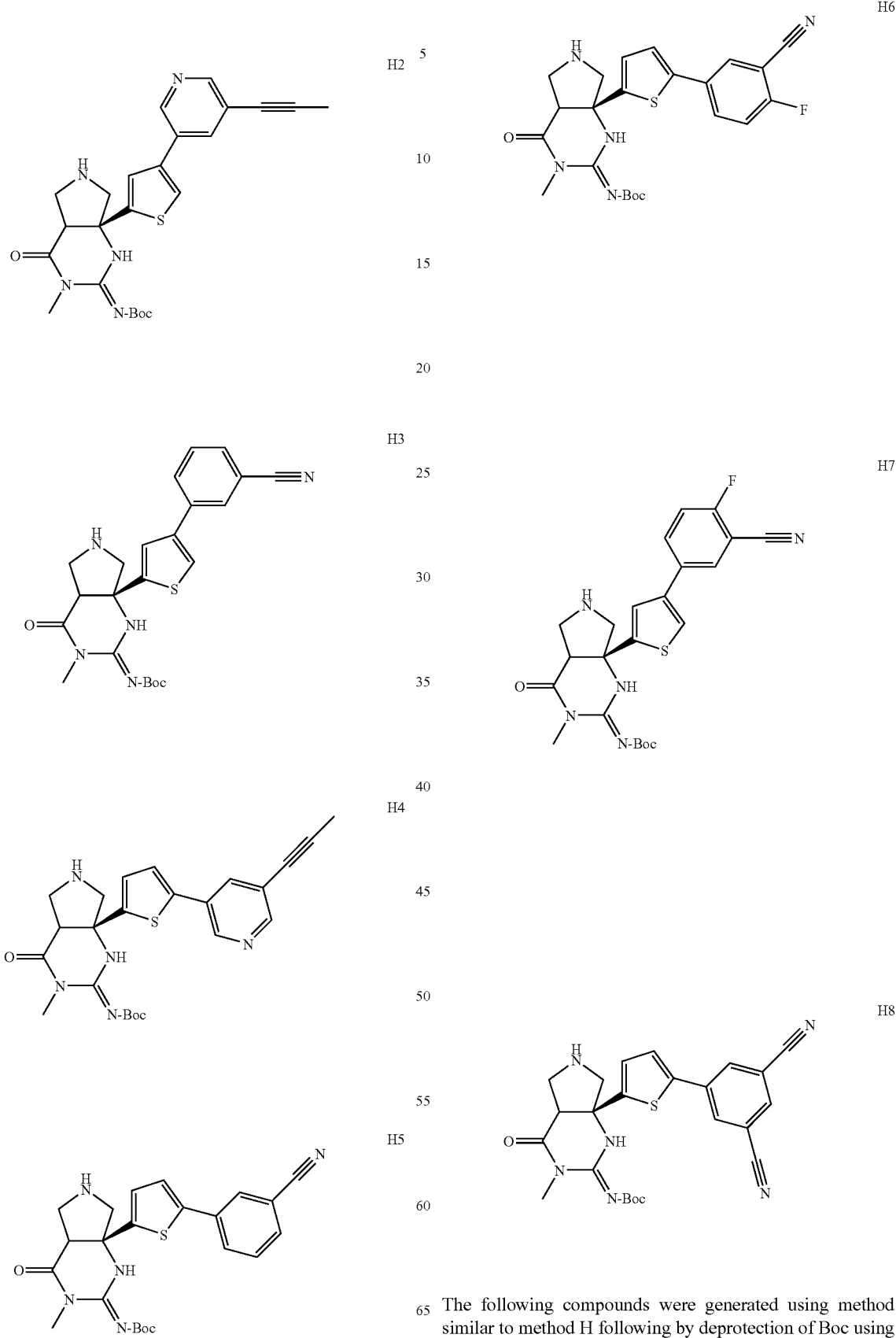
The following compounds were generated using method similar to method H following by deprotection of Boc using 20% TFA in DCM.

| Structure | Obs. Mass | Structure | Obs. Mass |
|---|---|---|---|
| 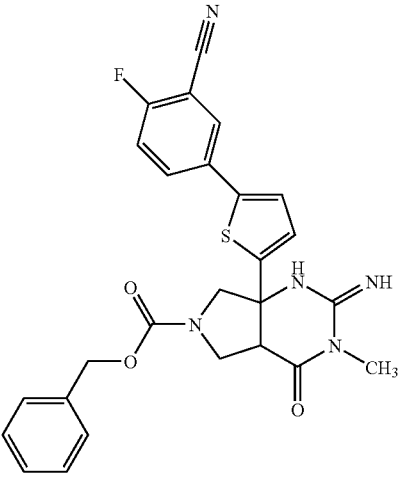 | 504.3 | 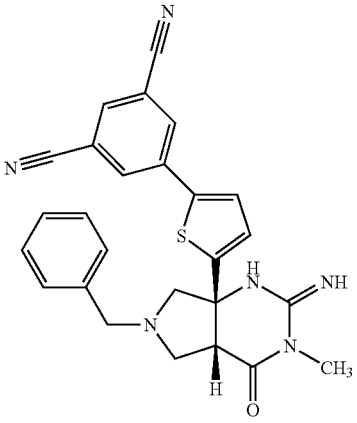 | 467.3 |
| 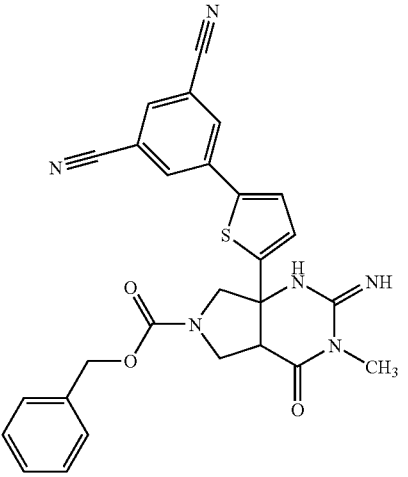 | 511.3 | 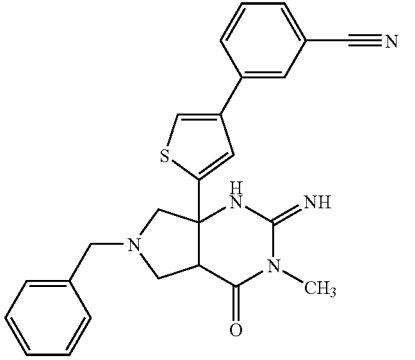 | NA |
| 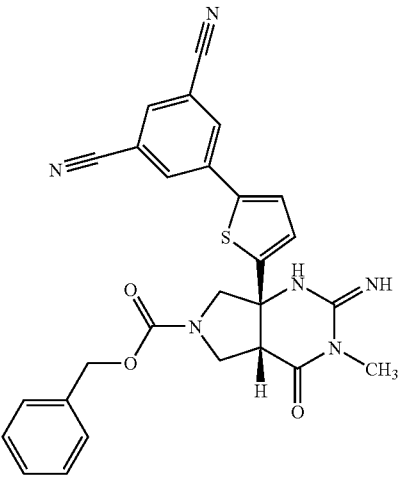 | 511.3 | 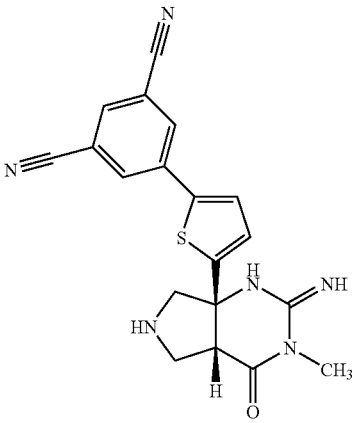 | 377.2 |

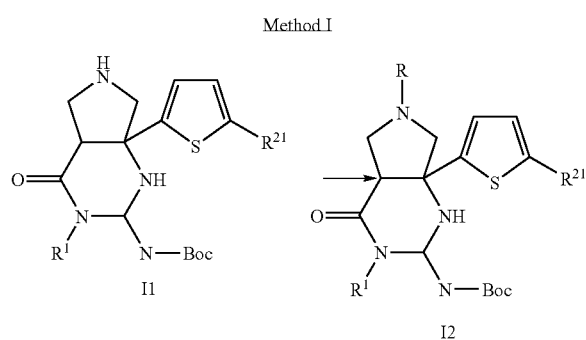

Method I

Method I, Step A:

To a DCM (2 ml) solution of I1 (35 mg) was added HOBt (15 mg), m-Fluorobenzoic acid (15.8 mg), DIEA (28 mg) followed by EDCI (21.5 mg) and the solution was stirred for 3 h. before it was extracted with EtOAc. The organic layer was dried, concentrated and residue chromatographed to give a product which was deprotected with 20% TFA/DCM to give product I1 after reverse phase purification.

NMR(H[1], CDCl$_3$) for H2 (R=m-F-benzoyl, R[1]=Me, R[21]=m-propynylpyridin-3-yl): δ10.71, br s, 1H; 8.85, s, 1H; 8.58, s, 1H; 8.20, s, 1H; 7.01-7.66, m, 6H; 3.80-4.45, m, 5H; 3.38, s, 3H; 2.13, s, 3H.

The following compounds were generated using similar method:

| Structure | Obs. Mass | Structure | Obs. Mass |
|---|---|---|---|
| 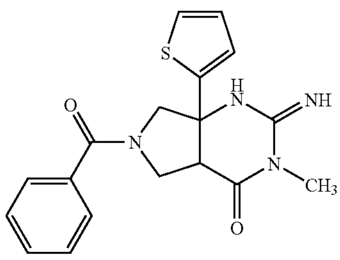 | 355.2 | 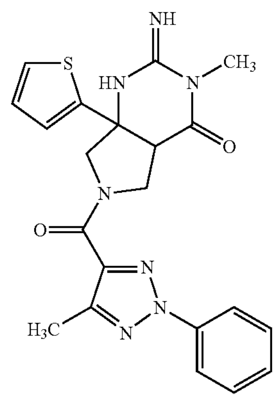 | 436.2 |
| 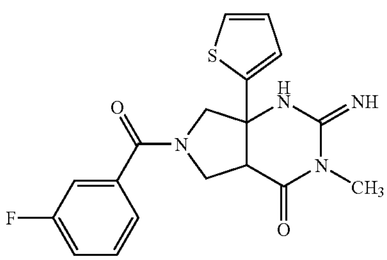 | 373.2 | 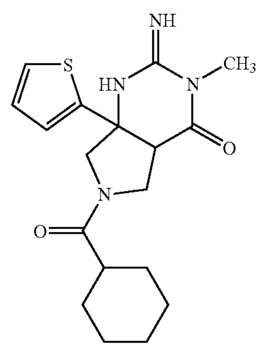 | 361.2 |
| 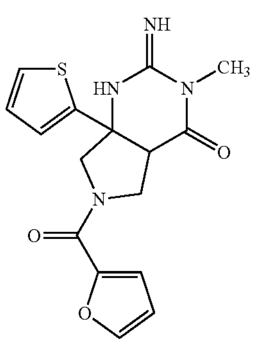 | 345.2 | 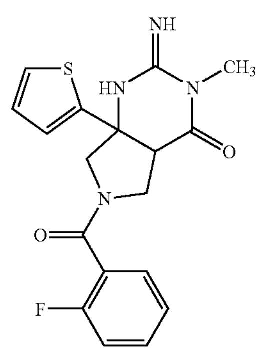 | 373.2 |

-continued

| Structure | Obs. Mass | Structure | Obs. Mass |
|---|---|---|---|
| 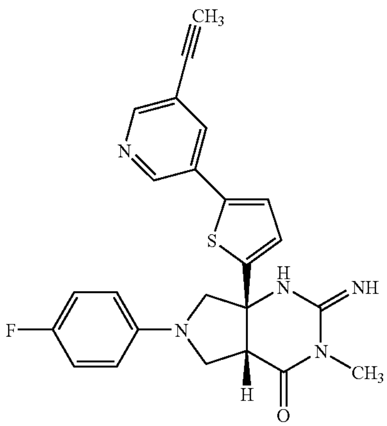 | 345.2 | 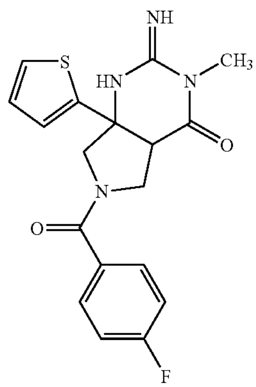 | 373.2 |
| 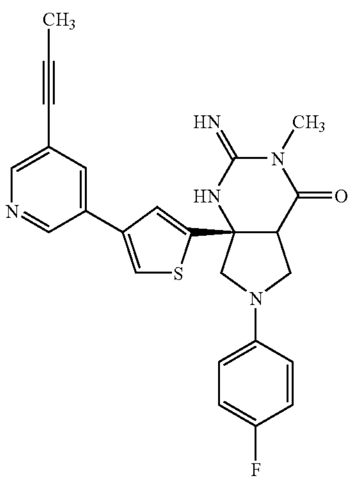 | 356.2 | 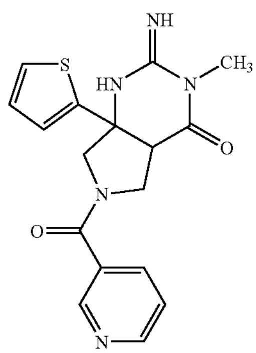 | 356.2 |
| 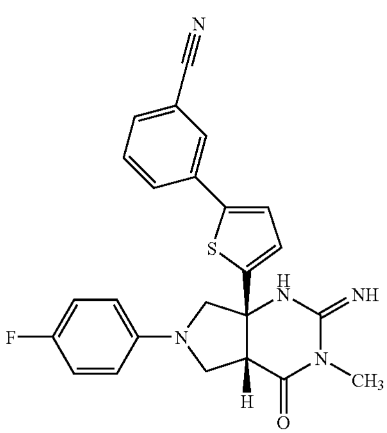 | 361.2 | 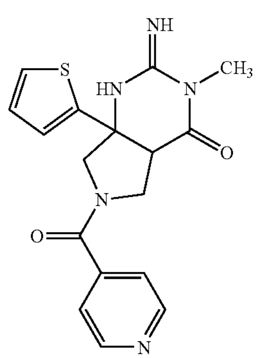 | 356.2 |

-continued
| Structure | Obs. Mass | Structure | Obs. Mass |
|---|---|---|---|
| 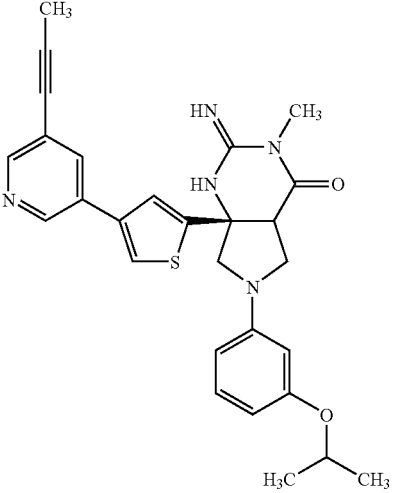 | 361.2 | 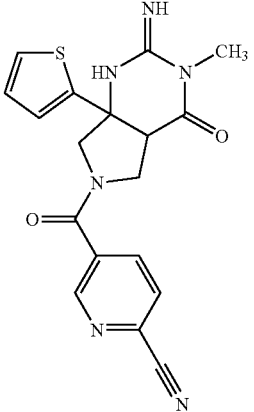 | 381.2 |
| 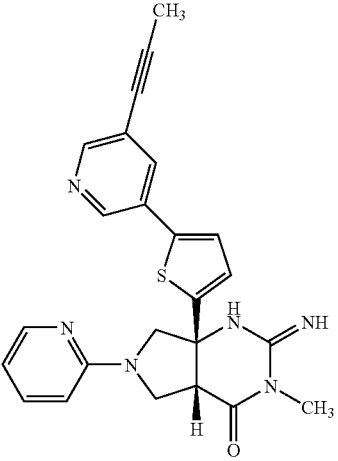 | 369.2 | 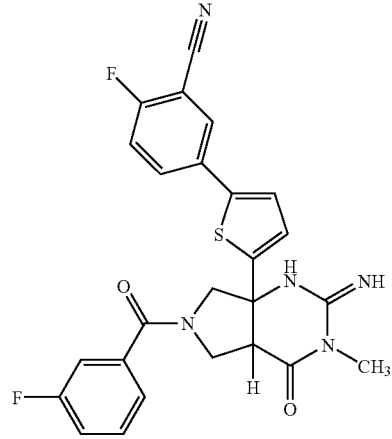 | 492.3 |
| 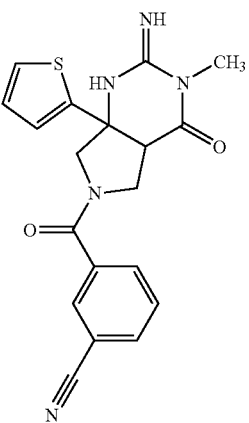 | 380.2 | 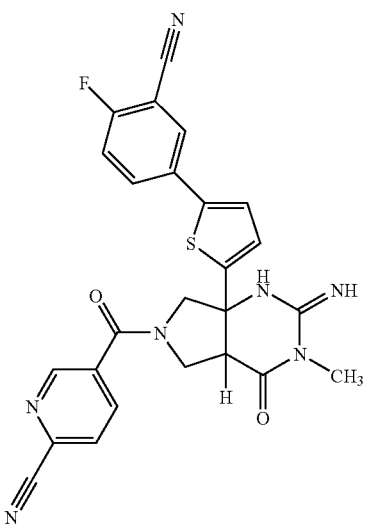 | 500.3 |

| Structure | Obs. Mass | Structure | Obs. Mass |
|---|---|---|---|
| 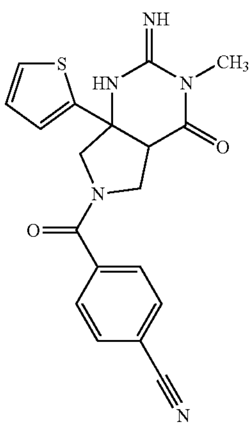 | 380.2 | 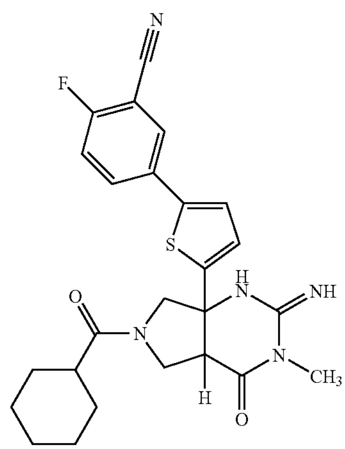 | 480.3 |
| 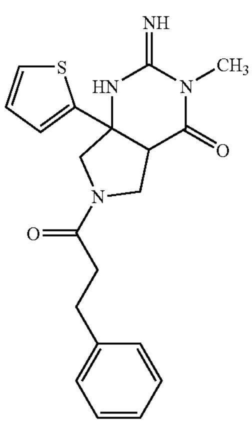 | 383.2 | 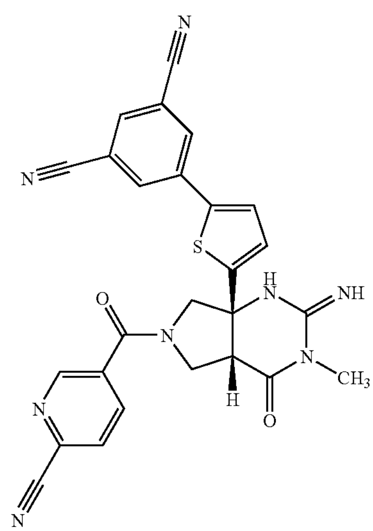 | 507.3 |
| 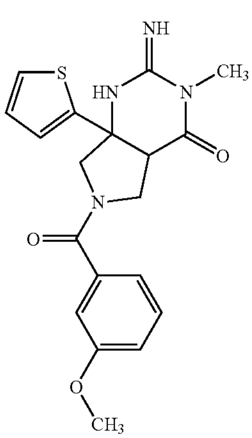 | 385.2 | 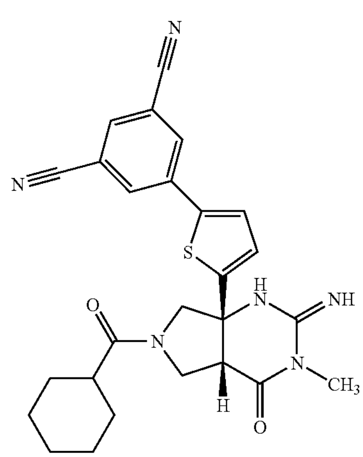 | 487.3 |

-continued
| Structure | Obs. Mass | Structure | Obs. Mass |
|---|---|---|---|
| 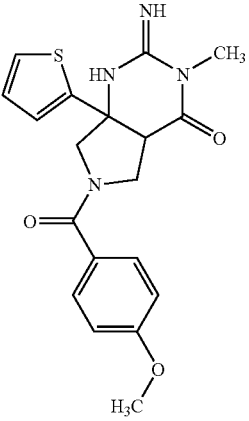 | 385.2 | 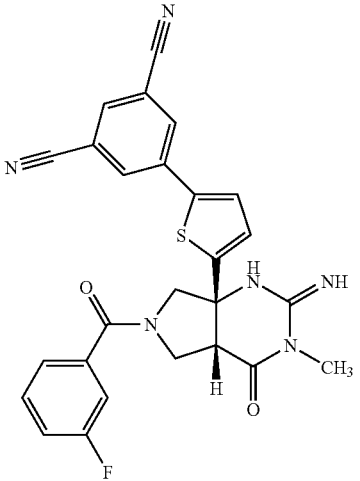 | 499.3 |
| 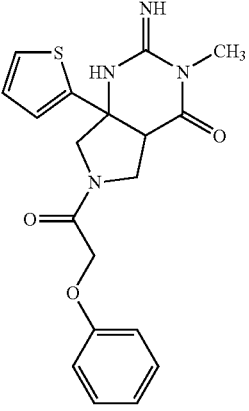 | 385.2 | 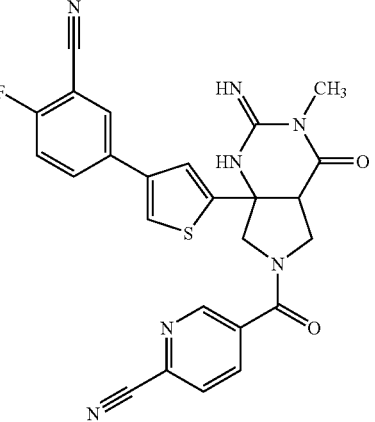 | 500.3 |
| 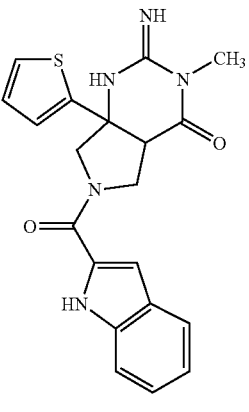 | 394.2 | 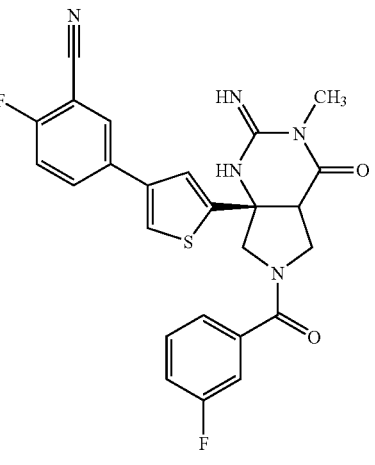 | 492.3 |

-continued

| Structure | Obs. Mass | Structure | Obs. Mass |
|---|---|---|---|
| 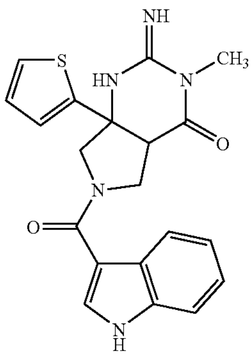 | 394.2 | 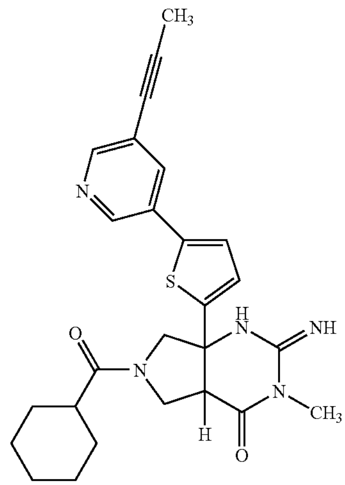 | 476.3 |
| 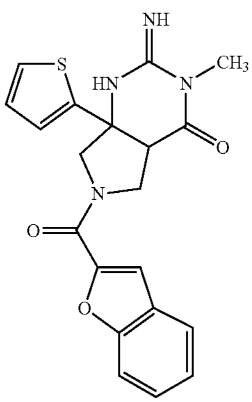 | 395.2 | 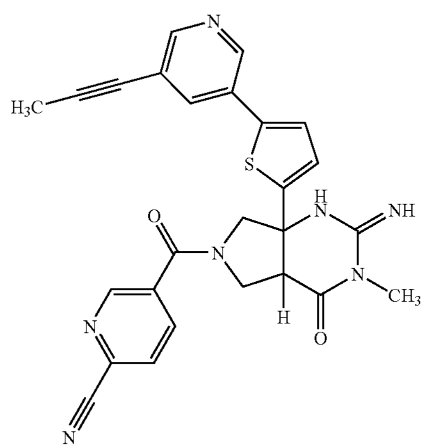 | 496.3 |
| 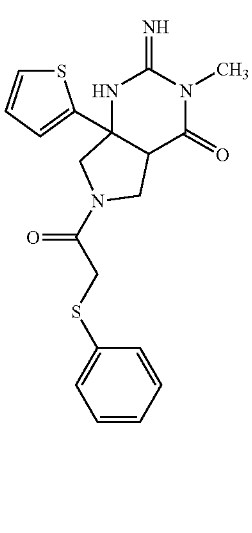 | 401.2 | 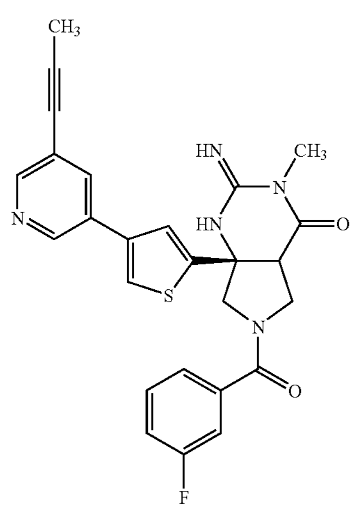 | 488.3 |

-continued
| Structure | Obs. Mass | Structure | Obs. Mass |
|---|---|---|---|
| 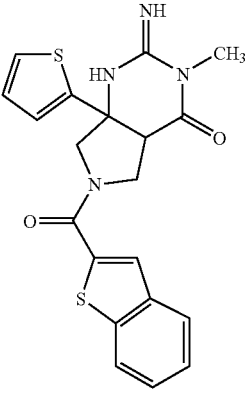 | 411.2 | 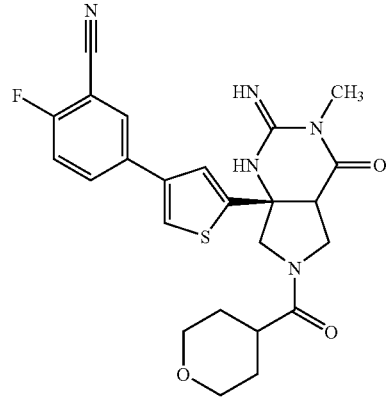 | 482.3 |
| 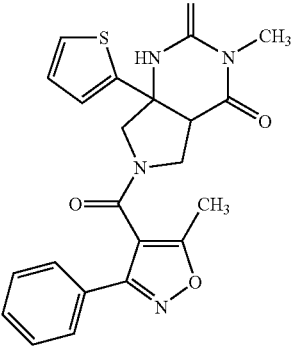 | 436.2 | 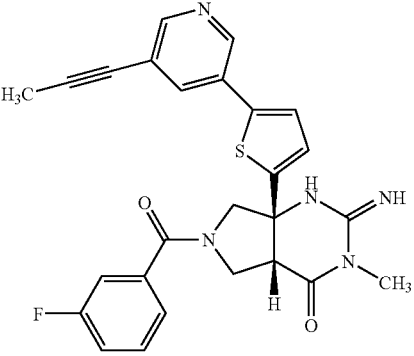 | 488.3 |
| 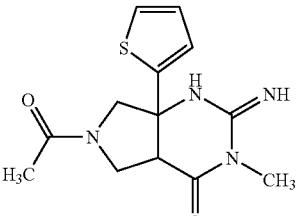 | 293.2 | 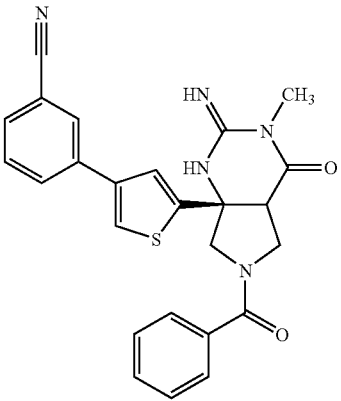 | 456.3 |

| Structure | Obs. Mass | Structure | Obs. Mass |
|---|---|---|---|
| (structure) | 470.3 | (structure) | 474.3 |
| (structure) | 506.3 | | |

To a DCM solution (2 ml) of H2 (25 mg, R²¹=m-propynylpyridin-3-yl, R¹=Me), p-F-phenylboronic acid (20 mg), Cu(OAc)₂, and 0.1 ml triethylamine was added preactivated 4 Å molecular sieves (5 micron, 20 mg). The reaction was stirred for 48 h before the solid was filtered and the organic solution concentrated and the residue chromatographed to give a product which was deprotected using 20% TFA/DCM to give J1 (R²¹=m-propynylpyridin-3-yl, R¹=Me and R=p-fluorophenyl) after reverse phase purification.

The following compounds were generated using similar method:

| Structure | Obs. Mass | Structure | Obs. Mass |
|---|---|---|---|
| (structure) | 341.2 | (structure) | 446.2 |

-continued
| | The following compounds were generated using similar method: | | |
|---|---|---|---|
| Structure | Obs. Mass | Structure | Obs. Mass |
| 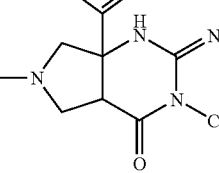 | 327.2 | 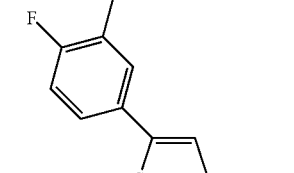 | 464.3 |
| 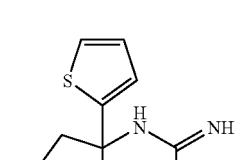 | 328.2 | 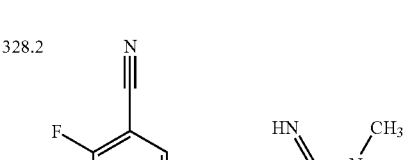 | 464.3 |
| 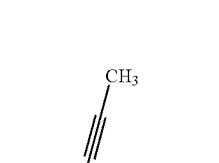 | 460.3 | 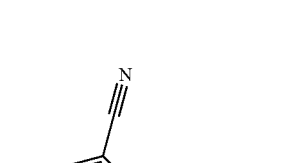 | 446.3 |

-continued

The following compounds were generated using similar method:

| Structure | Obs. Mass | Structure | Obs. Mass |
|---|---|---|---|
| 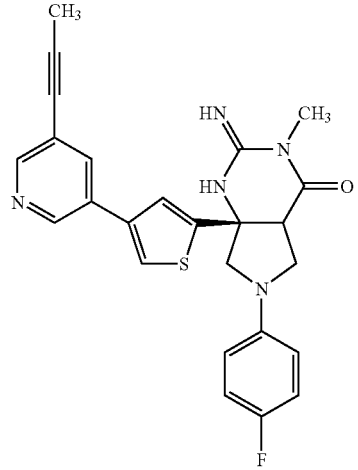 | 460.3 | 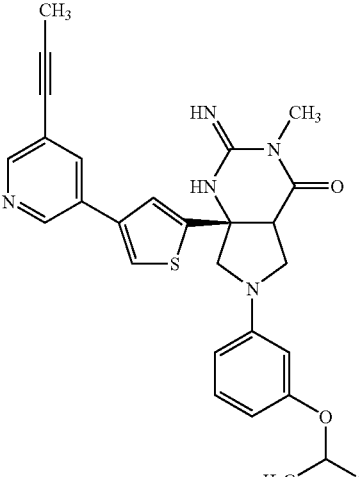 | 500.3 |

Method K, Step 1.

To a solution of K1 (3.5 g) in 60 ml 1:1 ration of DCM/ HOAc was added 1.5 g of NBS at 0° C. and the solution was allowed to warm-up to rt. The reaction mixture was pured into a mixture of DCM and sat. K2CO3/Na2SO3 (1:1) and the organic layer was concentrated, residue chromatographed to give K2 (100 mg) and K3 (750 mg).

| Structure | Obs. Mass |
|---|---|
| 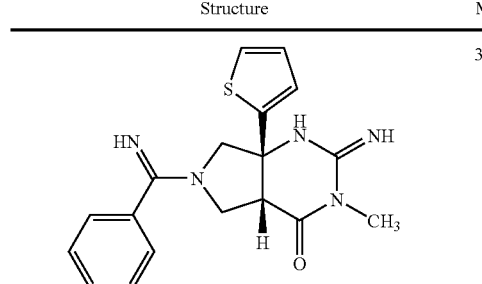 | 354.2 |

Method L

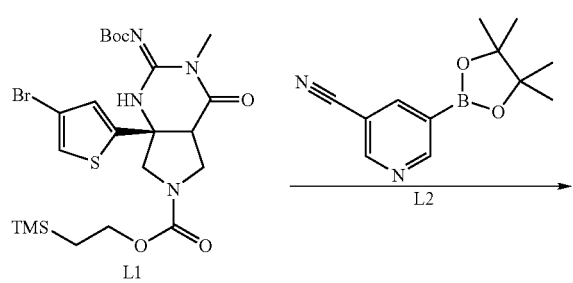

-continued

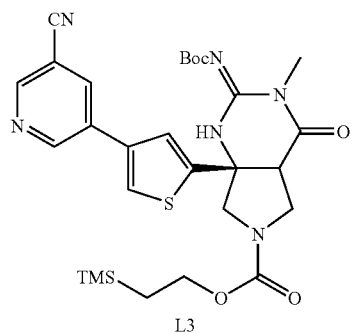

To a solution of bromide L1 (500 mg, 0.872 mmol, 1.0 equiv.) and boronic ester (300 mg, 1.30 mmol, 1.5 equiv.) in 3 mL tBuOH were added Tris-(dibenzylideneacetone)dipalladium (0) (119 mg, 0.130 mmol, 0.15 equiv.) and Tri-t-butylphosphonium tetrafluoroborate (119 mg) followed by aqueous K$_2$CO$_3$ (1M, 1.30 mL, 1.30 mmol, 1.5 equiv.). The resulting mixture was heated at 60° C. for 1 hr and TLC indicated completion of reaction. The reaction mixture was diluted with ethyl acetate and wash with water. The organic layer was dried with MgSO4, concentrated and purified via a silica gel column with ethyl acetate in hexanes.

NMR(H$^1$, CDCl$_3$) for L3: δ10.71, m, 1H; 8.96, s, 1H; 8.80, s, 1H; 8.40, s, 1H; 7.56, s, 1H; 7.24, s, 1H; 4.17-4.22, m, 2H; 3.87-4.11, m, 3H; 3.71-3.80, m, 1H; 3.50-3.60, m, 1H; 3.30, s, 3H; 1.52, s, 9H; 0.98-1.05, m, 2H; 0.07, s, 9H.

Method M

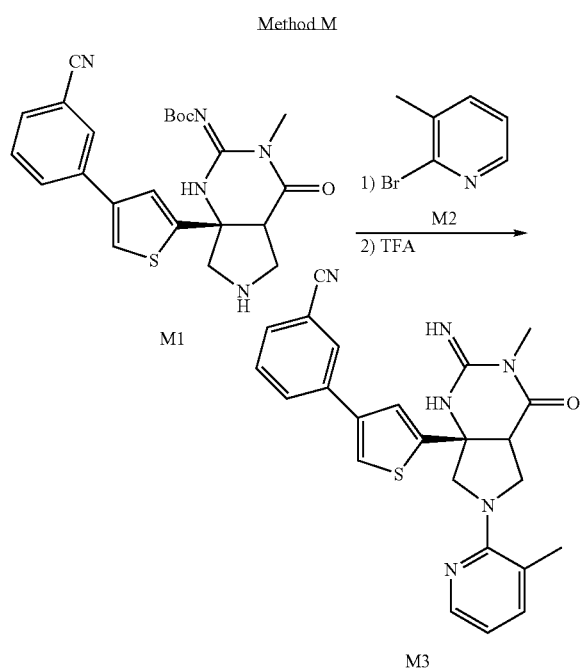

To a solution of amine M1 (15 mg, 0.033 mmol, 1.0 equiv.) and bromide M2 (5 equiv.) in 0.250 mL toluene were added Tris(dibenzylideneacetone)dipalladium (0) (3.0 mg, 0.0032 mmol, 0.10 equiv.) and racemic-2,2'-Bis-(diphenylphosphino)-1.1'-binaphthyl (3.0 mg) followed by 12 mg of NaOtBu. The resulting mixture was heated at 70° C. for 12 hr and the crude product was purified via a silica gel column eluted with EtOAc/Hexane to give a product which was treated with 20% TFA in DCM followed by reverse phase HPLC purification to give product M3.

NMR(H$^1$, CD$_3$OD) for M3: δ7.57-8.04, m, 8H; 7.00-7.04, m, 1H; 4.32-4.56, m, 4H; 4.12-4.17, m, 1H; 3.35, s, 3H; 2.55, s, 3H.

The following compounds were generated using method similar to Method M.

| Structure | Obs. Mass | Structure | Obs. Mass |
|---|---|---|---|
| | 430.2 | | |
| | 430.2 | | 470.3 |

-continued
| Structure | Obs. Mass | Structure | Obs. Mass |
|---|---|---|---|
| 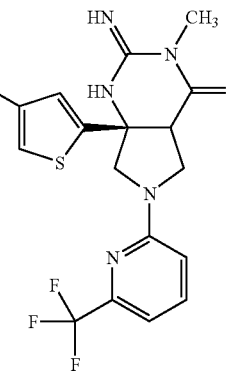 | 497.3 | 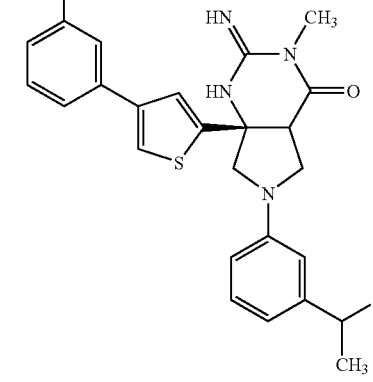 | 470.3 |
| 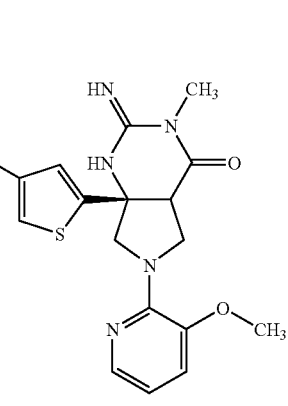 | 459.3 | 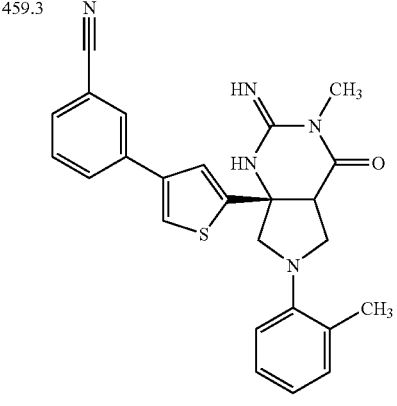 | 442.2 |
| 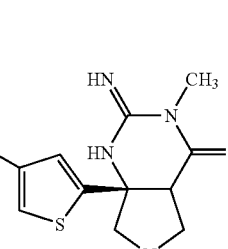 | 459.3 | 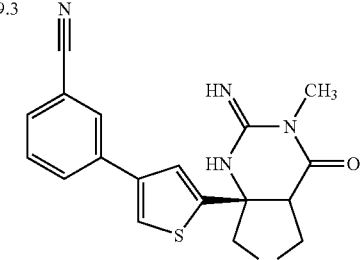 | 430.2 |

-continued

| Structure | Obs. Mass | Structure | Obs. Mass |
|---|---|---|---|
| 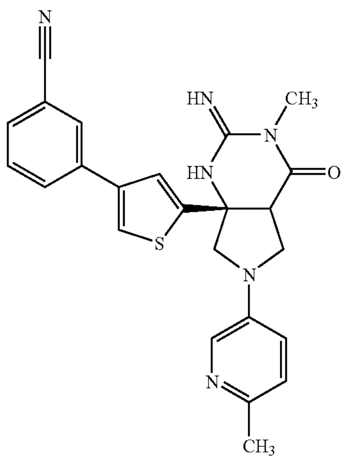 | 443.2 | 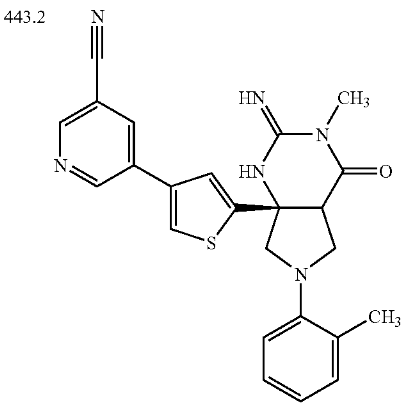 | 443.2 |
| 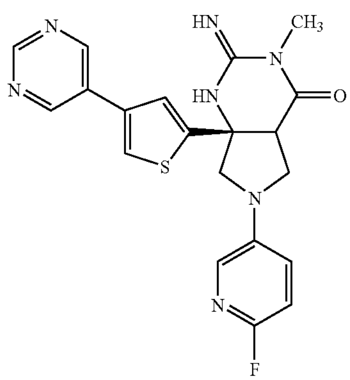 | 424.2 | 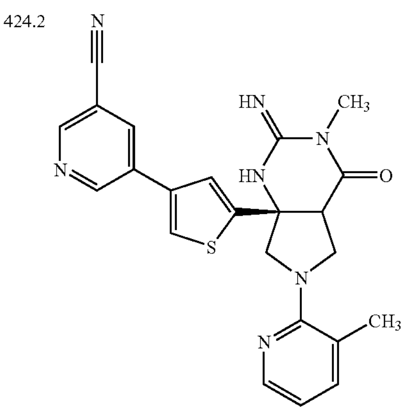 | 444.2 |
| 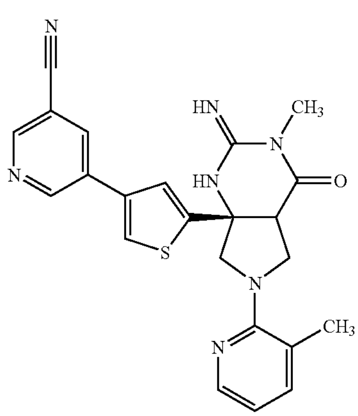 | 429.2 | 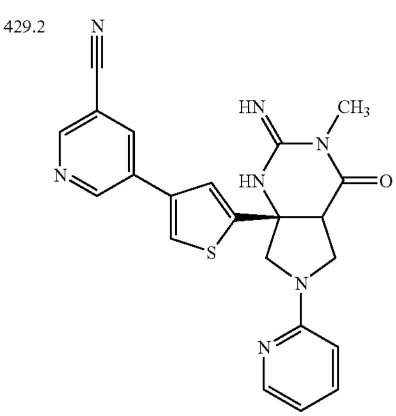 | 430.2 |

-continued

| Structure | Obs. Mass | Structure | Obs. Mass |
|---|---|---|---|
| | 443.2 | | 448.3 |
| | 443.2 | | 460.3 |
| | | | 419.2 |

| Structure | Obs. Mass | Structure | Obs. Mass |
|---|---|---|---|
| 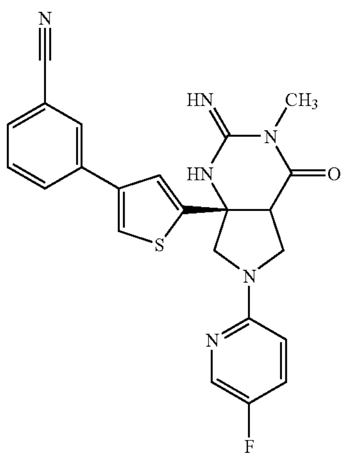 | 447.3 | 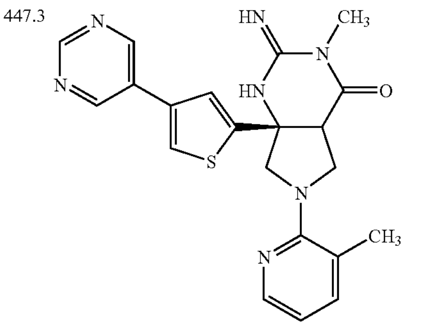 | 420.2 |
| 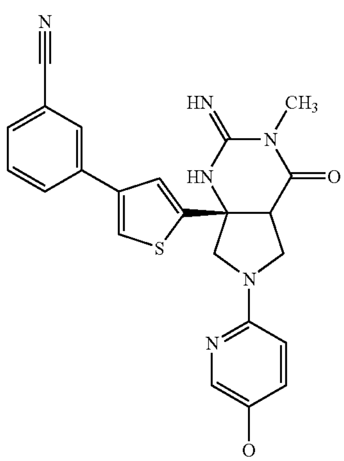 | 463.3 | 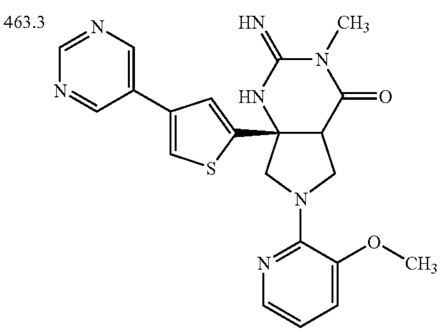 | 436.2 |
| 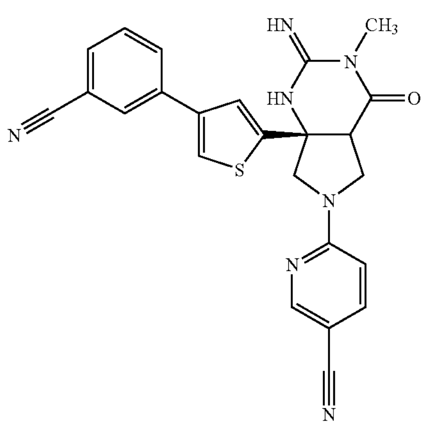 | 454.3 | 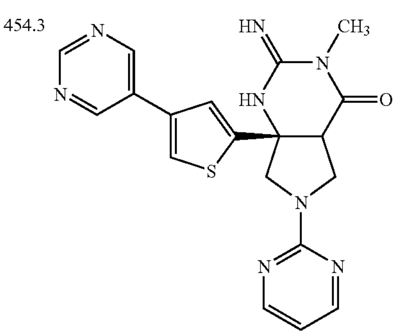 | 407.2 |

| Structure | Obs. Mass | Structure | Obs. Mass |
|---|---|---|---|
| 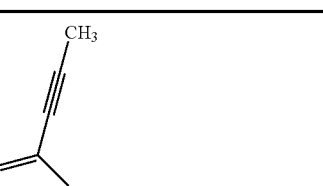 | 443.2 | | |

Human Cathepsin D FRET Assay

The substrate used below has been described (Y. Yasuda et al., J. Biochem., 125, 1137 (1999)). Substrate and enzyme are commercially available.

The assay can be run in a 30 µl final volume using a 384 well Nunc black plate. 8 concentrations of compound can be pre-incubated with enzyme for 30 mins at 37° C. followed by addition of substrate with continued incubation at 37° C. for 45 mins. The rate of increase in fluorescence is linear for over 1 h and is measured at the end of the incubation period using a Molecular Devices FLEX station plate reader. Kis are interpolated from the $IC_{50}s$ using a Km value of 4 µM and the substrate concentration of 2.5 µM.

Reagents
Na-Acetate pH 5
1% Brij-35 from 10% stock (Calbiochem)
DMSO
Purified (>95%) human liver Cathepsin D (Athens Research & Technology Cat# 16-12-030104)
Peptide substrate (Km=4 uM) Mca-Gly-Lys-Pro-Ile-Leu-Phe-Phe-Arg-Leu-Lys(Dnp)-D-Arg-$NH_2$ Bachem Cat # M-2455
Pepstatin is used as a control inhibitor (Ki~0.5 nM) and is available from Sigma.
Nunc 384 well black plates Final Assay Buffer Conditions
100 mM Na Acetate pH 5.0
0.02% Brij-35
1% DMSO Compound can be diluted to 3× final concentration in assay buffer containing 3% DMSO. 10 µl of compound will be added to 10 µl of 2.25 nM enzyme (3×) diluted in assay buffer without DMSO, mixed briefly, spun, and can be incubated at 37° C. for 30 mins. 3× substrate (7.5 µM) is prepared in 1× assay buffer without DMSO. 10 µl of substrate will be added to each well mixed and spun briefly to initiate the reaction. Assay plates can be incubated at 37 C for 45 mins and read on 384 compatible fluorescence plate reader using a 328 nm Ex and 393 nm Em.

BACE-1 Cloning, Protein Expression and Purification

A predicted soluble form of human BACE1 (sBACE1, corresponding to amino acids 1-454) can be generated from the full length BACE1 cDNA (full length human BACE1 cDNA in pCDNA4/mycHisA construct; University of Toronto) by PCR using the advantage-GC cDNA PCR kit (Clontech, Palo Alto, Calif.). A HindIII/PmeI fragment from pCDNA4-sBACE1 myc/His can be blunt ended using Klenow and subcloned into the Stu I site of pFASTBACI(A) (Invitrogen). A sBACE1 mycHis recombinant bacmid can be generated by transposition in DH10Bac cells(GIBCO/BRL). Subsequently, the sBACE1mycHis bacmid construct can be transfected into sf9 cells using CellFectin (Invitrogen, San Diego, Calif.) in order to generate recombinant baculovirus. Sf9 cells are grown in SF 900-II medium (Invitrogen) supplemented with 3% heat inactivated FBS and 0.5× penicillin/streptomycin solution (Invitrogen). Five milliliters of high titer plaque purified sBACEmyc/His virus is used to infect 1 L of logarithmically growing sf9 cells for 72 hours. Intact cells are pelleted by centrifugation at 3000×g for 15 minutes. The supernatant, containing secreted sBACE1, is collected and diluted 50% v/v with 100 mM HEPES, pH 8.0. The diluted medium is loaded onto a Q-sepharose column. The Q-sepharose column is washed with Buffer A (20 mM HEPES, pH 8.0, 50 mM NaCl).

Proteins, can be eluted from the 0-sepharose column with Buffer B (20 mM HEPES, pH 8.0, 500 mM NaCl). The protein peaks from the Q-sepharose column are pooled and loaded onto a Ni-NTA agarose column. The Ni-NTA column can be then washed with Buffer C (20 mM HEPES, pH 8.0, 500 mM NaCl). Bound proteins are then eluted with Buffer D (Buffer C+250 mM imidazole). Peak protein fractions as determined by the Bradford Assay (Biorad, Calif.) are concentrated using a Centricon 30 concentrator (Millipore). sBACE1 purity is estimated to be ~90% as assessed by SDS-PAGE and Commassie Blue staining. N-terminal sequencing indicates that greater than 90% of the purified sBACE1 contained the prodomain; hence this protein is referred to as sproBACE1.

Peptide Hydrolysis Assay

The inhibitor, 25 nM EuK-biotin labeled APPsw substrate (EuK-KTEEISEVNLDAEFRHDKC-biotin (SEQ ID NO: 1); CIS-Bio International, France), 5 µM unlabeled APPsw peptide (KTEEISEVNLDAEFRHDK; (SEQ ID NO: 2) American Peptide Company, Sunnyvale, Calif.), 7 nM sproBACE1, 20 mM PIPES pH 5.0, 0.1% Brij-35 (protein grade, Calbiochem, San Diego, Calif.), and 10% glycerol were pre-incubated for 30 min at 30° C. Reactions were initiated by addition of substrate in a 5 µl aliquot resulting in a total volume of 25 µl. After 3 hr at 30° C. reactions were terminated by addition of an equal volume of 2× stop buffer containing 50 mM Tris-HCl pH 8.0, 0.5 M KF, 0.001% Brij-35, 20 µg/ml SA-XL665 (cross-linked allophycocyanin protein coupled to streptavidin; CIS-Bio International, France) (0.5 µg/well). Plates were shaken briefly and spun at 1200×g for 10 seconds to pellet all liquid to the bottom of the plate before the incubation. HTRF measurements were made on a Packard Discovery® HTRF plate reader using 337 nm laser light to excite the sample followed by a 50 µs delay and simultaneous measurements of both 620 nm and 665 nm emissions for 400 µs.

$IC_{50}$ determinations for inhibitors, (I), are determined by measuring the percent change of the relative fluorescence at 665 nm divided by the relative fluorescence at 620 nm, (665/620 ratio), in the presence of varying concentrations of I and a fixed concentration of enzyme and substrate. Nonlinear regression analysis of this data can be performed using GraphPad Prism 3.0 software selecting four parameter logistic equation, that allows for a variable slope. Y=Bottom+(Top-Bottom)/(1+10^((LogEC50−X)*Hill Slope)); X is the logarithm of concentration of I, Y is the percent change in ratio and Y starts at bottom and goes to top with a sigmoid shape.

Using the above assay, the $K_i$ values of some of the compounds were determined. The $K_i$ values ranged from 0.1 to 100,000 nM.

Human Mature Renin Enzyme Assay

Human Renin can be cloned from a human kidney cDNA library and C-terminally epitope-tagged with the V5-6His sequence into pCDNA3.1. pCNDA3.1-Renin-V5-6His is stably expressed in HEK293 cells and purified to >80% using standard Ni-Affinity chromatography. The prodomain of the recombinant human renin-V5-6His can be removed by limited proteolysis using immobilized TPCK-trypsin to give mature-human renin. Renin enzymatic activity can be monitored using a commercially available fluorescence resonance energy transfer (FRET) peptide substrate, RS-1 (Molecular Probes, Eugene, Oreg.) in 50 mM Tris-HCl pH 8.0, 100 mM NaCl, 0.1% Brij-35 and 5% DMSO buffer for 40 mins at 30° Celsius in the presence or absence of different concentrations of test compounds. Mature human Renin is present at approximately 200 nM. Inhibitory activity is defined as the percent decrease in renin induced fluorescence at the end of the 40 min incubation compared to vehicle controls and samples lacking enzyme.

In the aspect of the invention relating to a combination of at least one compound of formula I with at least one cholinesterase inhibitor, acetyl- and/or butyrylcholinesterase inhibitors can be used. Examples of cholinesterase inhibitors are tacrine, donepezil, rivastigmine, galantamine, pyridostigmine and neostigmine, with tacrine, donepezil, rivastigmine and galantamine being preferred. Preferably, these combinations are directed to the treatment of Alzheimer's Disease.

In one aspect of the invention, a combination of at least one compound of formula I with at least one muscarinic $m_1$ agonist or $m_2$ antagonist can be used. Examples of $m_1$ agonists are known in the art. Examples of $m_2$ antagonists are also known in the art; in particular, $m_2$ antagonists are disclosed in U.S. Pat. Nos. 5,883,096; 6,037,352; 5,889,006; 6,043,255; 5,952,349; 5,935,958; 6,066,636; 5,977,138; 6,294,554; 6,043,255; and 6,458,812; and in WO 03/031412, all of which are incorporated herein by reference.

In other aspects of the invention relating to a combination of at least one compound of formula I and at least one other agent, for example a beta secretase inhibitor; a gamma secretase inhibitor; an HMG-CoA reductase inhibitor such as atorvastatin, lovastatin, simvastatin, pravastatin, fluvastatin and rosuvastatin; non-steroidal anti-inflammatory agents such as, but not necessarily limited to ibuprofen, relafen or naproxen; N-methyl-D-aspartate receptor antagonists such as memantine; anti-amyloid antibodies including humanized monoclonal antibodies; vitamin E; nicotinic acetylcholine receptor agonists; CB1 receptor inverse agonists or CB1 receptor antagonists; antibiotics such as doxycycline; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity. Preferably, these combinations are directed to the treatment of Alzheimer's Disease.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 300 mg/day, preferably 1 mg/day to 50 mg/day, in two to four divided doses.

When a compound of formula I is used in combination with a cholinesterase inhibitor to treat cognitive disorders, these two active components may be co-administered simultaneously or sequentially, or a single pharmaceutical composition comprising a compound of formula I and a cholinesterase inhibitor in a pharmaceutically acceptable carrier can be administered. The components of the combination can be administered individually or together in any conventional oral or parenteral dosage form such as capsule, tablet, powder, cachet, suspension, solution, suppository, nasal spray, etc. The dosage of the cholinesterase inhibitor can be determined from published material, and may range from 0.001 to 100 mg/kg body weight.

When separate pharmaceutical compositions of a compound of formula I and a cholinesterase inhibitor are to be administered, they can be provided in a kit comprising in a single package, one container comprising a compound of formula I in a pharmaceutically acceptable carrier, and a separate container comprising a cholinesterase inhibitor in a pharmaceutically acceptable carrier, with the compound of formula I and the cholinesterase inhibitor being present in amounts such that the combination is therapeutically effective. A kit is advantageous for administering a combination when, for example, the components must be administered at different time intervals or when they are in different dosage forms.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:
1. A compound having the following structure:

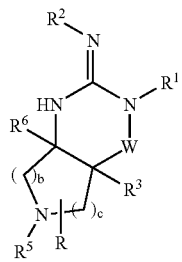

or a stereoisomer, tautomer, or pharmaceutically acceptable salt of said compound, said stereoisomer, or said tautomer, wherein:
b is 1;
c is 1,
W is —C(=S)—, —C(=O)—, —C($R^6$)($R^7$)—, —C($R^6$)($R^7$)C(=O)—, or —C(=N($R^5$))—;
R is absent or 1 to 5 $R^{21}$ groups;
$R^1$, and $R^5$ are independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, —$OR^{15}$, —CN, —C(=N$R^{11}$)$R^8$, —C(O)$R^8$, —C(O)O$R^9$, —S(O)$R^{10}$, —S(O)$_2R^{10}$, —C(O)N($R^{11}$)($R^{12}$), —S(O)N($R^{11}$)($R^{12}$), —S(O)$_2$N($R^{11}$)($R^{12}$), —NO$_2$, —N=C($R^8$)$_2$ and —N($R^{11}$)($R^{12}$),
wherein each of the alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl in $R^5$ is unsubstituted or substituted by 1 to 5 $R^{21}$ groups;
$R^2$ is selected from the group consisting of H, aryl, and aryl substituted by 1 to 5 $R^{21}$ groups;
$R^3$ and $R^7$ are independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, halo, —CH$_2$—O—Si($R^9$)($R^{10}$)($R^{19}$), —SH, —CN, —$OR^9$, —C(O)$R^8$, —C(O)O$R^9$, —C(O)N($R^{11}$)($R^{12}$), —$SR^{19}$, —S(O)N($R^{11}$)($R^{12}$), —S(O)$_2$N($R^{11}$)($R^{12}$), —N($R^{11}$)($R^{12}$), —($R^{11}$)C(O)$R^8$, —N($R^{11}$)S(O)$R^{10}$, —N($R^{11}$)S(O)$_2R^{10}$, —N($R^{11}$)C(O)N($R^{12}$)($R^{13}$), —N($R^{11}$)C(O)O$R^9$ and —C(=NOH)$R^8$;
$R^6$ is selected from the group consisting of aryl, ($R^{21}$)$_{1-5}$-aryl, thiophenyl, and ($R^{21}$)$_{1-3}$-thiophenyl;
$R^8$ is independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, —$OR^{15}$, —N($R^{15}$)($R^{16}$), —N($R^{15}$)C(O)$R^{16}$, —N($R^{15}$)S(O)$R^{16}$, —N($R^{15}$)S(O)$_2R^{16}$, —N($R^{15}$)S(O)$_2$N($R^{16}$)($R^{17}$), —N($R^{15}$)S(O)N($R^{16}$)($R^{17}$), —N($R^{15}$)C(O)N($R^{16}$)($R^{17}$) and —N($R^{15}$)C(O)O$R^{16}$;
$R^9$ is independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, and heterocycloalkenylheteroaryl;
$R^{10}$ is independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, aryl heterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl and —N($R^{15}$)($R^{16}$);
$R^{11}$, $R^{12}$, and $R^{13}$ are independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, —C(O)R$^8$, —C(O)OR$^9$, —S(O)R$^{10}$, —S(O)$_2$R$^{10}$, —C(O)N(R$^{15}$)(R$^{16}$), —S(O)N(R$^{15}$)(R$^{16}$), —S(O)$_2$N(R$^{15}$)(R$^{16}$) and —CN;

R$^{15}$, R$^{16}$ and R$^{17}$ are independently selected from the group consisting of H, alkyl, arylalkyl, heteroarylalkyl, cycloalkylalkyl, heterocycloalkylalkyl, arylcycloalkylalkyl, heteroarylcycloalkylalkyl, aryl heterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, R$^{18}$-alkyl, R$^{18}$-arylalkyl, R$^{18}$-heteroarylalkyl, R$^{18}$-cycloalkylalkyl, R$^{18}$-heterocycloalkylalkyl, R$^{18}$-arylcycloalkylalkyl, R$^{18}$-heteroarylcycloalkylalkyl, R$^{18}$-arylheterocycloalkylalkyl, R$^{18}$-heteroarylheterocycloalkylalkyl, R$^{18}$-cycloalkyl, R$^{18}$-arylcycloalkyl, R$^{18}$-heteroarylcycloalkyl, R$^{18}$-heterocycloalkyl, R$^{18}$-arylheterocycloalkyl, R$^{18}$-heteroarylheterocycloalkyl, R$^{18}$-alkenyl, R$^{18}$-arylalkenyl, R$^{18}$-cycloalkenyl, R$^{18}$-arylcycloalkenyl, R$^{18}$-heteroarylcycloalkenyl, R$^{18}$-heterocycloalkenyl, R$^{18}$-arylheterocycloalkenyl, R$^{18}$-heteroarylheterocycloalkenyl, R$^{18}$-alkynyl, R$^{18}$-arylalkynyl, R$^{18}$-aryl, R$^{18}$-cycloalkylaryl, R$^{18}$-heterocycloalkylaryl, R$^{18}$-cycloalkenylaryl, R$^{18}$-heterocycloalkenylaryl, R$^{18}$-heteroaryl, R$^{18}$-cycloalkylheteroaryl, R$^{18}$-heterocycloalkylheteroaryl, R$^{18}$-cycloalkenylheteroaryl, and R$^{18}$-heterocycloalkenylheteroaryl; or R$^{15}$, R$^{16}$ and R$^{17}$ are

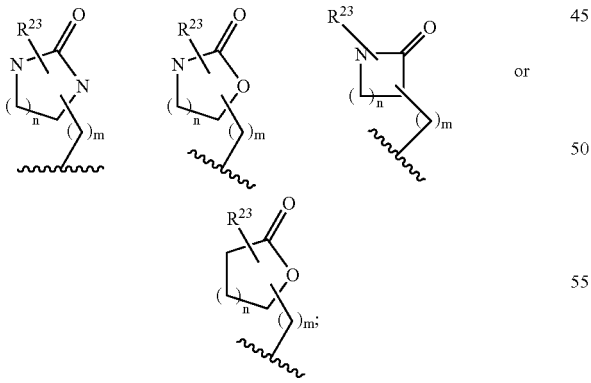

wherein R$^{23}$ numbers 0 to 5 substituents, m is 0 to 6 and n is 0 to 5;

R$^{18}$ is 1-5 substituents independently selected from the group consisting of alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, —NO$_2$, halo, HO-alkoxyalkyl, —CF$_3$, —ON, alkyl-CN, —C(O)R$^{19}$, —C(O)OH, —C(O)OR$^{19}$, —C(O)NHR$^{20}$, —C(O)NH$_2$, —C(O)NH$_2$—C(O)N(alkyl)$_2$, —C(O)N(alkyl)(aryl), —C(O)N(alkyl)(heteroaryl), —SR$^{19}$, —S(O)$_2$R$^{20}$, —S(O)NH$_2$, —S(O)NH(alkyl), —S(O)N(alkyl)(alkyl), —S(O)NH(aryl), —S(O)$_2$NH$_2$, —S(O)$_2$NHR$^{19}$, —S(O)$_2$NH(heterocycloalkyl), —S(O)$_2$N(alkyl)$_2$, —S(O)$_2$N(alkyl)(aryl), —OCF$_3$, —OH, —OR$^{20}$, —O-heterocycloalkyl, —O-cycloalkylalkyl, —O-heterocycloalkylalkyl, —NH$_2$, —NHR$^{20}$, —N(alkyl)$_2$, —N(arylalkyl)$_2$, —N(arylalkyl)-(heteroarylalkyl), —NHC(O)R$^{20}$, —NHC(O)NH$_2$, —NHC(O)NH(alkyl), —NHC(O)N(alkyl)(alkyl), —N(alkyl)C(O)NH(alkyl), —N(alkyl)C(O)N(alkyl)(alkyl), —NHS(O)$_2$R$^{20}$, —NHS(O)$_2$NH(alkyl), —NHS(O)$_2$N(alkyl)(alkyl), —N(alkyl)S(O)$_2$NH(alkyl) and —N(alkyl)S(O)$_2$N(alkyl)(alkyl);

or two R$^{18}$ moieties on adjacent carbons can be linked together to form

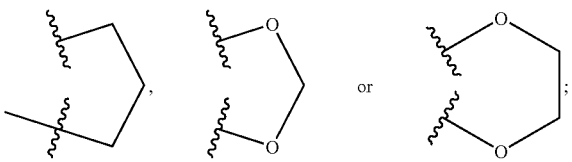

R$^{19}$ is alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl or heterocycloalkenylheteroaryl;

R$^{20}$ is halo substituted aryl, alkyl, arylalkyl, heteroarylalkyl, cycloalkylalkyl, heterocycloalkylalkyl, arylcycloalkylalkyl, heteroarylcycloalkylalkyl, aryl heterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl or heterocycloalkenylheteroaryl;

each $R^{21}$ group is independently selected from the group consisting of alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroaryl heterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, halo, —CN, —C(=NR$^{11}$)R$^{15}$, —OR$^{15}$, —C(O)R$^{15}$, —C(O)OR$^{15}$, —C(O)N(R$^{15}$)(R$^{16}$), —SR$^{15}$, S(O)N(R$^{15}$)(R$^{16}$), —CH(R$^{15}$)(R$^{16}$), —S(O)$_2$N(R$^{15}$)(R$^{16}$), —C(=NOR$^{15}$)R$^{16}$, —P(O)(OR$^{15}$)(OR$^{16}$), —N(R$^{15}$)(R$^{16}$), -alkyl-N(R$^{15}$)(R$^{16}$), —N(R$^{15}$)C(O)R$^{16}$, —CH$_2$—N(R$^{15}$)C(O)R$^{16}$, —CH$_2$—N(R$^{15}$)C(O)N(R$^{16}$)(R$^{17}$), —CH$_2$—R$^{15}$; —CH$_2$N(R$^{15}$)(R$^{16}$), —N(R$^{15}$)S(O)R$^{16}$, —N(R$^{15}$)S(O)$_2$R$^{16}$, —CH$_2$—N(R$^{15}$)S(O)$_2$R$^{16}$, —N(R$^{15}$)S(O)$_2$N(R$^{16}$)(R$^{17}$), N(R$^{15}$)S(O)N(R$^{16}$)(R$^{17}$), —N(R$^{15}$)C(O)N(R$^{16}$)(R$^{17}$), —CH$_2$—N(R$^{15}$)C(O)N(R$^{16}$)(R$^{17}$), —N(R$^{15}$)C(O)OR$^{16}$, —CH$_2$—N(R$^{15}$)C(O)OR$^{16}$, —S(O)R$^{15}$, —N$_3$, —NO$_2$ and —S(O)$_2$R$^{15}$;

and wherein each of the alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroaryl heterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl and heterocycloalkenylheteroaryl groups in R$^{21}$ are independently unsubstituted or substituted by 1 to 5 R$^{22}$ groups;

each $R^{22}$ group is independently selected from the group consisting of alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, halo, —CF$_3$, —CN, —C(=NR$^{11}$)R$^{15}$, —OR$^{15}$, —C(O)R$^{15}$, —C(O)OR$^{15}$, -alkyl-C(O)OR$^{15}$, —C(O)N(R$^{15}$)(R$^{16}$), —SR$^{15}$, —S(O)N(R$^{15}$)(R$^{16}$), —S(O)$_2$N(R$^{15}$)(R$^{16}$), —C(=NOR$^{15}$)R$^{16}$, —(P(O)(OR$^{15}$)(OR$^{16}$), —N(R$^{15}$)(R$^{16}$), -alkyl-N(R$^{15}$)(R$^{16}$), —N(R$^{15}$)C(O)R$^{16}$, —CH$_2$—N(R$^{15}$)C(O)R$^{16}$, —N(R$^{15}$)S(O)R$^{16}$, —N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$), —CH$_2$—N(R$^{15}$)C(O)N(R$^{16}$)(R$^{17}$), —N(R$^{15}$)C(O)OR$^{16}$, —CH$_2$—N(R$^{15}$)C(O)OR$^{16}$, —N$_3$, —NO$_2$, —S(O)R$^{15}$ and —S(O)$_2$R$^{15}$;

or two $R^{21}$ or two $R^{22}$ moieties on adjacent carbons can be linked together to form

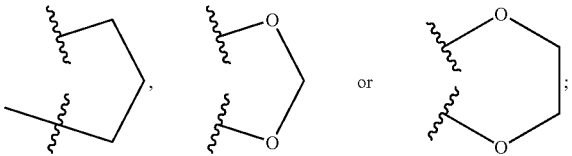

and when $R^{21}$ or $R^{22}$ are selected from the group consisting of —C(=NOR$^{15}$)R$^{16}$, —N(R$^{15}$)C(O)R$^{16}$, —CH$_2$—N(R$^{15}$)C(O)R$^{16}$, —N(R$^{15}$)S(O)R$^{16}$, —N(R$^{15}$)S(O)$_2$R$^{16}$, —CH$_2$—N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$), —CH$_2$—N(R$^{15}$)C(O)N(R$^{16}$)(R$^{17}$), —N(R$^{15}$)C(O)OR$^{16}$ and —CH$_2$—N(R$^{15}$)C(O)OR$^{16}$, $R^{15}$ and $R^{16}$ together can be a $C_2$ to $C_4$ chain wherein, optionally, one, two or three ring carbons can be replaced by —C(O)— or —N(H)— and $R^{15}$ and $R^{16}$, together with the atoms to which they are attached, form a 5 to 7 membered ring, optionally substituted by $R^{23}$;

$R^{23}$ is 0 to 5 groups independently selected from the group consisting of alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, aryl heterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, halo, —CN, —OR$^{24}$, —C(O)R$^{24}$, —C(O)OR$^{24}$, —C(O)N(R$^{24}$)(R$^{25}$), —SR$^{24}$, —S(O)N(R$^{24}$)(R$^{25}$) —S(O)$_2$N(R$^{24}$)(R$^{25}$), —C(=NOR$^{24}$)R$^{25}$, —P(O)(OR$^{24}$)(OR$^{25}$), —N(R$^{24}$)(R$^{25}$), -alkyl-N(R$^{24}$)(R$^{25}$), —N(R$^{24}$)C(O)R$^{25}$, —CH$_2$—N(R$^{24}$)C(O)R$^{25}$, —N(R$^{24}$)S(O)R$^{25}$, —N(R$^{24}$)S(O)$_2$R$^{25}$, —CH$_2$—N(R$^{24}$)S(O)$_2$R$^{25}$, —N(R$^{24}$)S(O)$_2$N(R$^{25}$)(R$^{26}$), —N(R$^{24}$)S(O)N(R$^{25}$)(R$^{26}$), —N(R$^{24}$)C(O)N(R$^{25}$)(R$^{26}$), —CH$_2$—N(R$^{24}$)C(O)N(R$^{25}$)(R$^{26}$), —N(R$^{24}$)C(O)OR$^{25}$, —CH$_2$—N(R$^{24}$)C(O)OR$^{25}$, —S(O)R$^{24}$ and —S(O)$_2$R$^{24}$; and wherein each of the alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl and heterocycloalkenylheteroaryl groups in R$^{23}$ are independently unsubstituted or substituted by R$^{27}$;

$R^{24}$, $R^{25}$ and $R^{26}$ are independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, $R^{27}$-alkyl, $R^{27}$-arylalkyl, $R^{27}$-heteroarylalkyl, $R^{27}$-cycloalkylalkyl, $R^{27}$-heterocycloalkylalkyl, $R^{27}$-arylcycloalkylalkyl, $R^{27}$-heteroarylcycloalkylalkyl, $R^{27}$-arylheterocycloalkylalkyl, $R^{27}$-heteroarylheterocycloalkylalkyl, $R^{27}$-cycloalkyl, $R^{27}$-arylcycloalkyl, $R^{27}$-heteroarylcycloalkyl, $R^{27}$-heterocycloalkyl, $R^{27}$-aryl heterocycloalkyl, $R^{27}$-heteroarylheterocycloalkyl, $R^{27}$-alkenyl, $R^{27}$-arylalkenyl, $R^{27}$-cycloalkenyl, $R^{27}$-arylcycloalkenyl, $R^{27}$-heteroarylcycloalkenyl, $R^{27}$-heterocycloalkenyl, $R^{27}$-arylheterocycloalkenyl, $R^{27}$-heteroarylheterocycloalkenyl, $R^{27}$-alkynyl, $R^{27}$-arylalkynyl, $R^{27}$-aryl, $R^{27}$-cycloalkylaryl, $R^{27}$-heterocycloalkylaryl, $R^{27}$-cycloalkenylaryl, $R^{27}$-heterocycloalkenylaryl, $R^{27}$-heteroaryl, $R^{27}$-cycloalkylheteroaryl, $R^{27}$-heterocycloalkylheteroaryl, $R^{27}$-cycloalkenylheteroaryl and $R^{27}$-heterocycloalkenylheteroaryl;

$R^{27}$ is 1-5 substituents independently selected from the group consisting of alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, —NO$_2$, halo, —CF$_3$, —CN, alkyl-CN, —C(O)R$^{28}$, —C(O)OH, —C(O)OR$^{28}$, —C(O)NHR$^{29}$, —C(O)N(alkyl)$_2$, —C(O)N(alkyl)(aryl), —C(O)N(alkyl)(heteroaryl), —SR$^{28}$, —S(O)$_2$R$^{29}$, —S(O)NH$_2$, —S(O)NH(alkyl), —S(O)N(alkyl)(alkyl), —S(O)NH(aryl), —S(O)$_2$NH$_2$, —S(O)$_2$NHR$^{28}$, —S(O)$_2$NH(aryl), —S(O)$_2$NH(heterocycloalkyl), —S(O)$_2$N(alkyl)$_2$, —S(O)$_2$N(alkyl)(aryl), —OH, —OR$^{29}$, —O-heterocycloalkyl, —O-cycloalkylalkyl, —O-heterocycloalkylalkyl, —NH$_2$, —NHR$^{29}$, —N(alkyl)$_2$, —N(arylalkyl)$_2$, —N(arylalkyl)(heteroarylalkyl), —NHC(O)R$^{29}$, —NHC(O)NH$_2$, —NHC(O)NH(alkyl), —NHC(O)N(alkyl)(alkyl), —N(alkyl)C(O)NH(alkyl), —N(alkyl)C(O)N(alkyl)(alkyl), —NHS(O)$_2$R$^{29}$, —NHS(O)$_2$NH(alkyl), —NHS(O)$_2$N(alkyl)(alkyl), —N(alkyl)S(O)$_2$NH(alkyl) and —N(alkyl)S(O)$_2$N(alkyl)(alkyl);

$R^{28}$ is alkyl, arylalkyl, heteroarylalkyl, cycloalkylalkyl, heterocycloalkylalkyl, arylcycloalkylalkyl, heteroarylcycloalkylalkyl, aryl heterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl or heterocycloalkenylheteroaryl;

$R^{29}$ is alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl or heterocycloalkenylheteroaryl, wherein:

"heteroaryl" means a moiety selected from pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, and benzothiazolyl;

"heterocyclyl" (or "heterocycloalkyl") means a moiety selected from piperidyl, pyrrolidinyl, pyrazolidinyl, imidazolinyl, piperazinyl, morpholinyl, thiomorpholinyl, dithianyl, trithianyl, thiazolidinyl, 1,3-dioxolanyl, 1,4-dioxanyl, tetrahydrofuranyl, tetrahydrothiophenyl, and tetrahydrothiopyranyl; and "heterocyclenyl" (or "hetocyloalkenyl") means a heterocyclyl moiety as defined above which contains at least one carbon-carbon double bond and/or at least one carbon-nitrogen double bond.

2. A compound of claim 1, wherein: R is absent.
3. A compound of claim 1, wherein: R is 1 to 5 $R^{21}$ groups.
4. A compound of claim 1, wherein: $R^1$ is alkyl.
5. A compound of claim 1, wherein: $R^1$ is methyl.
6. A compound of claim 1, wherein: $R^2$ is H.
7. A compound of claim 1, wherein: $R^3$ is H.
8. A compound having the following structure:

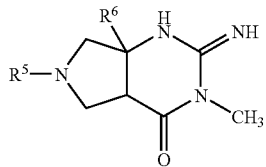

or a stereoisomer, tautomer, or pharmaceutically acceptable salt of said compound, said stereoisomer, or said tautomer, wherein:

$R^5$ is selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, —OR$^{15}$, —CN, —C(=NR$^{11}$)R$^8$, —C(O)R$^8$, —C(O)OR$^9$, —S(O)R$^{10}$, —S(O)$_2$R$^{10}$, —C(O)N(R$^{11}$)(R$^{12}$), —S(O)N(R$^{11}$)(R$^{12}$), —S(O)$_2$N(R$^{11}$)(R$^{12}$), —NO$_2$, —N=C(R$^8$)$_2$ and —N(R$^{11}$)(R$^{12}$), wherein each of the alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, aryl heterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl in R$^5$ is unsubstituted or substituted by 1 to 5 R$^{21}$ groups;

R$^6$ is selected from the group consisting of aryl, (R$^{21}$)$_{1-5}$-aryl, thiophenyl, and (R$^{21}$)$_{1-3}$-thiophenyl;

R$^8$ is independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, —OR$^{15}$, —N(R$^{15}$)(R$^{16}$), —N(R$^{15}$)C(O)R$^{16}$, —N(R$^{15}$)S(O)R$^{16}$, —N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$) and —N(R$^{15}$)C(O)OR$^{16}$;

R$^9$ is independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, and heterocycloalkenylheteroaryl;

R$^{10}$ is independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl and —N(R$^{15}$)(R$^{16}$);

R$^{11}$ and R$^{12}$ are each independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, —C(O)R$^8$, —C(O)OR$^9$, —S(O)R$^{10}$, —S(O)$_2$R$^{10}$, —C(O)N(R$^{15}$)(R$^{16}$), —S(O)N(R$^{15}$)(R$^{16}$), —S(O)$_2$N(R$^{15}$)(R$^{16}$) and —CN;

R$^{15}$, R$^{16}$ and R$^{17}$ are independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, R$^{18}$-alkyl, R$^{18}$-arylalkyl, R$^{18}$-heteroarylalkyl, R$^{18}$-cycloalkylalkyl, R$^{18}$-heterocycloalkylalkyl, R$^{18}$-arylcycloalkylalkyl, R$^{18}$-heteroarylcycloalkylalkyl, R$^{18}$-arylheterocycloalkylalkyl, R$^{18}$-heteroarylheterocycloalkylalkyl, R$^{18}$-cycloalkyl, R$^{18}$-arylcycloalkyl, R$^{18}$-heteroarylcycloalkyl, R$^{18}$-heterocycloalkyl, R$^{18}$-arylheterocycloalkyl, R$^{18}$-heteroarylheterocycloalkyl, R$^{18}$-alkenyl, R$^{18}$-arylalkenyl, R$^{18}$-cycloalkenyl, R$^{18}$-arylcycloalkenyl, R$^{18}$-heteroarylcycloalkenyl, R$^{18}$-heterocycloalkenyl, R$^{18}$-arylheterocycloalkenyl, R$^{18}$-heteroarylheterocycloalkenyl, R$^{18}$-alkynyl, R$^{18}$-arylalkynyl, R$^{18}$-aryl, aryl, R$^{18}$-cycloalkylaryl, R$^{18}$-heterocycloalkylaryl, R$^{18}$-cycloalkenylaryl, R$^{18}$-heterocycloalkenylaryl, R$^{18}$-heteroaryl, R$^{18}$-cycloalkylheteroaryl, R$^{18}$-heterocycloalkylheteroaryl, R$^{18}$-cycloalkenylheteroaryl, and R$^{18}$-heterocycloalkenylheteroaryl; or R$^{15}$, R$^{16}$ and R$^{17}$ are

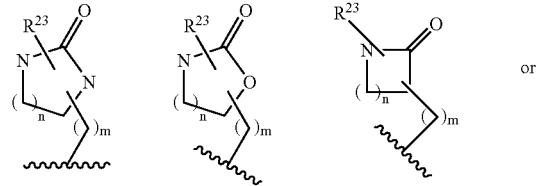

or

-continued

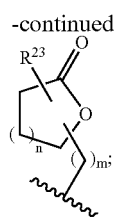

wherein $R^{23}$ numbers 0 to 5 substituents, m is 0 to 6 and n is 0 to 5;

$R^{18}$ is 1-5 substituents independently selected from the group consisting of alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, —$NO_2$, halo, HO-alkoxyalkyl, —$CF_3$, —CN, alkyl-CN, —C(O)$R^{19}$, —C(O)OH, —C(O)O$R^{19}$, —C(O)NH$R^{20}$, —C(O)NH$_2$, —C(O)NH$_2$—C(O)N(alkyl)$_2$, —C(O)N(alkyl)(aryl), —C(O)N(alkyl)(heteroaryl), —S$R^{19}$, —S(O)$_2R^{20}$, —S(O)NH$_2$, —S(O)NH(alkyl), —S(O)N(alkyl)(alkyl), —S(O)NH(aryl), —S(O)$_2$NH$_2$, —S(O)$_2$NH$R^{19}$, —S(O)$_2$NH(heterocycloalkyl), —S(O)$_2$N(alkyl)$_2$, —S(O)$_2$N(alkyl)(aryl), —OCF$_3$, —OH, —O$R^{20}$, —O-heterocycloalkyl, —O-cycloalkylalkyl, —O-heterocycloalkylalkyl, —NH$_2$, —NH$R^{20}$, —N(alkyl)$_2$, —N(arylalkyl)$_2$, —N(arylalkyl)-(heteroarylalkyl), —NHC(O)$R^{20}$, —NHC(O)NH$_2$, —NHC(O)NH(alkyl), —NHC(O)N(alkyl)(alkyl), —N(alkyl)C(O)NH(alkyl), —N(alkyl)C(O)N(alkyl)(alkyl), —NHS(O)$_2R^{20}$, —NHS(O)$_2$NH(alkyl), —NHS(O)$_2$N(alkyl)(alkyl), —N(alkyl)S(O)$_2$NH(alkyl) and —N(alkyl)S(O)$_2$N(alkyl)(alkyl);

or two $R^{18}$ moieties on adjacent carbons can be linked together to form

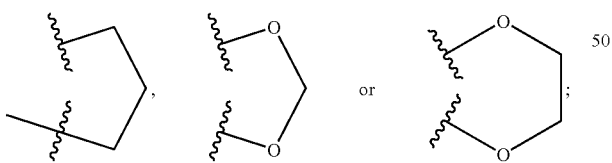

$R^{19}$ is alkyl, arylalkyl, heteroarylalkyl, cycloalkylalkyl, heterocycloalkylalkyl, arylcycloalkylalkyl, heteroarylcycloalkylalkyl, aryl heterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl or heterocycloalkenylheteroaryl;

$R^{20}$ is halo substituted aryl, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl or heterocycloalkenylheteroaryl;

each $R^{21}$ group is independently selected from the group consisting of alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, aryl heterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, halo, —CN, —C(=N$R^{11}$)$R^{15}$, —O$R^{15}$, —C(O)$R^{15}$, —C(O)O$R^{15}$, —C(O)N($R^{15}$)($R^{16}$), —S$R^{15}$, —S(O)N($R^{15}$)($R^{16}$), —CH($R^{15}$)($R^{16}$), —S(O)$_2$N($R^{15}$)($R^{16}$), —C(=NO$R^{15}$)$R^{16}$, —P(O)(O$R^{15}$)(O$R^{16}$), —N($R^{15}$)($R^{16}$), -alkyl-N($R^{15}$)($R^{16}$), —N($R^{15}$)C(O)$R^{16}$, —CH$_2$—N($R^{15}$)C(O)$R^{16}$, —CH$_2$—N($R^{15}$)C(O)N($R^{16}$)($R^{17}$), —CH$_2$—$R^{15}$; —CH$_2$N($R^{15}$)($R^{16}$), —N($R^{15}$)S(O)$R^{16}$, —N($R^{15}$)S(O)$_2R^{16}$, —CH$_2$—N($R^{15}$)S(O)$_2R^{16}$, —N($R^{15}$)S(O)$_2$N($R^{16}$)($R^{17}$), —N($R^{15}$)S(O)N($R^{16}$)($R^{17}$), —N($R^{15}$)C(O)N($R^{16}$)($R^{17}$), —CH$_2$—N($R^{15}$)C(O)N($R^{16}$)($R^{17}$), —N($R^{15}$)C(O)O$R^{16}$, —CH$_2$—N($R^{15}$)C(O)O$R^{16}$, —S(O)$R^{15}$, —$N_3$, —$NO_2$ and —S(O)$_2R^{15}$;

and wherein each of the alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl and heterocycloalkenylheteroaryl groups in $R^{21}$ are independently unsubstituted or substituted by 1 to 5 $R^{22}$ groups;

each $R^{22}$ group is independently selected from the group consisting of alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, halo, —$CF_3$, —CN, —C(=$NR^{11}$)$R^{15}$, —$OR^{15}$, C(O)$R^{15}$, —C(O)$OR^{15}$, -alkyl-C(O)$OR^{15}$, —C(O)N($R^{15}$)($R^{16}$), —$SR^{15}$, —S(O)N($R^{15}$)($R^{16}$), —S(O)$_2$N($R^{15}$)($R^{16}$), —C(=$NOR^{15}$)$R^{16}$, —P(O)($OR^{15}$)($OR^{16}$), —N($R^{15}$)($R^{16}$), -alkyl-N($R^{15}$)($R^{16}$), —N($R^{15}$)C(O)$R^{16}$, —CH$_2$—N($R^{15}$)C(O)$R^{16}$, —N($R^{15}$)S(O)$R^{16}$, —N($R^{15}$)S(O)$_2$$R^{16}$, —CH$_2$—N($R^{15}$)S(O)$_2$$R^{16}$, —N($R^{15}$)S(O)$_2$N($R^{16}$)($R^{17}$), —N($R^{15}$)S(O)N($R^{16}$)($R^{17}$), —N($R^{15}$)C(O)N($R^{16}$)($R^{17}$), —CH$_2$—N($R^{15}$)C(O)N($R^{16}$)($R^{17}$), —N($R^{15}$)C(O)$OR^{16}$, —CH$_2$—N($R^{15}$)C(O)$OR^{16}$, —N$_3$, —NO$_2$, —S(O)$R^{15}$ and —S(O)$_2$$R^{15}$;

or two $R^{21}$ or two $R^{22}$ moieties on adjacent carbons can be linked together to form

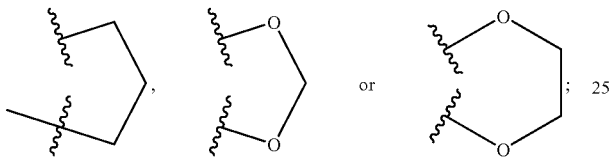

and when $R^{21}$ or $R^{22}$ are selected from the group consisting of —C(=$NOR^{15}$)$R^{16}$, —N($R^{15}$)C(O)$R^{16}$, —CH$_2$—N($R^{15}$)C(O)$R^{16}$, —N($R^{15}$)S(O)$R^{16}$, —N($R^{15}$)S(O)$_2$$R^{16}$, —CH$_2$—N($R^{15}$)S(O)$_2$$R^{16}$, —N($R^{15}$)S(O)$_2$N($R^{16}$)($R^{17}$), —N($R^{15}$)S(O)N($R^{16}$)($R^{17}$), —N($R^{15}$)C(O)N($R^{16}$)($R^{17}$), —CH$_2$—N($R^{15}$)C(O)N($R^{16}$)($R^{17}$), —N($R^{15}$)C(O)$OR^{16}$ and —CH$_2$—N($R^{15}$)C(O)$OR^{16}$, $R^{15}$ and $R^{16}$ together can be a $C_2$ to $C_4$ chain wherein, optionally, one, two or three ring carbons can be replaced by —C(O)— or —N(H)— and $R^{15}$ and $R^{16}$, together with the atoms to which they are attached, form a 5 to 7 membered ring, optionally substituted by $R^{23}$;

$R^{23}$ is 0 to 5 groups independently selected from the group consisting of alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, halo, —CN, —$OR^{24}$, —C(O)$R^{24}$, —C(O)$OR^{24}$, —C(O)N($R^{24}$)($R^{25}$), —$SR^{24}$, —S(O)N($R^{24}$)($R^{25}$), —S(O)$_2$N($R^{24}$)($R^{25}$), —C(=$NOR^{24}$)$R^{25}$, —P(O)($OR^{24}$)($OR^{25}$), —N($R^{24}$)($R^{25}$), -alkyl-N($R^{24}$)($R^{25}$), —N($R^{24}$)C(O)$R^{25}$, —CH$_2$—N($R^{24}$)C(O)$R^{25}$, —N($R^{24}$)S(O)$R^{25}$, —N($R^{24}$)S(O)$_2$$R^{25}$, —CH$_2$—N($R^{24}$)S(O)$_2$$R^{25}$, —N($R^{24}$)S(O)$_2$N($R^{25}$)($R^{26}$), —N($R^{24}$)S(O)N($R^{25}$)($R^{26}$), —N($R^{24}$)C(O)N($R^{25}$)($R^{26}$), —CH$_2$—N($R^{24}$)C(O)N($R^{25}$)($R^{26}$), —N($R^{24}$)C(O)$OR^{25}$, —CH$_2$—N($R^{24}$)C(O)$OR^{25}$, —S(O)$R^{24}$ and —S(O)$_2$$R^{24}$; and wherein each of the alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroaryl heterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl and heterocycloalkenylheteroaryl groups in $R^{23}$ are independently unsubstituted or substituted by $R^{27}$;

$R^{24}$, $R^{25}$ and $R^{26}$ are independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, $R^{27}$-alkyl, $R^{27}$-arylalkyl, $R^{27}$-heteroarylalkyl, $R^{27}$-cycloalkylalkyl, $R^{27}$-heterocycloalkylalkyl, $R^{27}$-arylcycloalkylalkyl, $R^{27}$-heteroarylcycloalkylalkyl, $R^{27}$-arylheterocycloalkylalkyl, $R^{27}$-heteroarylheterocycloalkylalkyl, $R^{27}$-cycloalkyl, $R^{27}$-arylcycloalkyl, $R^{27}$-heteroarylcycloalkyl, $R^{27}$-heterocycloalkyl, $R^{27}$-arylheterocycloalkyl, $R^{27}$-heteroarylheterocycloalkyl, $R^{27}$-alkenyl, $R^{27}$-arylalkenyl, $R^{27}$-cycloalkenyl, $R^{27}$-arylcycloalkenyl, $R^{27}$-heteroarylcycloalkenyl, $R^{27}$-heterocycloalkenyl, $R^{27}$-arylheterocycloalkenyl, $R^{27}$-heteroarylheterocycloalkenyl, $R^{27}$-alkynyl, $R^{27}$-arylalkynyl, $R^{27}$-aryl, $R^{27}$-cycloalkylaryl, $R^{27}$-heterocycloalkylaryl, $R^{27}$-cycloalkenylaryl, $R^{27}$-heterocycloalkenylaryl, $R^{27}$-heteroaryl, $R^{27}$-cycloalkylheteroaryl, $R^{27}$-heterocycloalkylheteroaryl, $R^{27}$-cycloalkenylheteroaryl and $R^{27}$-heterocycloalkenylheteroaryl;

$R^{27}$ is 1-5 substituents independently selected from the group consisting of alkyl, aryl alkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, —NO$_2$, halo, —$CF_3$, —CN, alkyl-CN, —C(O)$R^{28}$, —C(O)OH, —C(O)$OR^{28}$, —C(O)NH$R^{29}$, —C(O)N(alkyl)$_2$, —C(O)N(alkyl)(aryl), —C(O)N(alkyl)(heteroaryl), —SR²⁸, —S(O)₂R²⁹, —S(O)NH₂, —S(O)NH(alkyl), —S(O)N(alkyl)(alkyl), —S(O)NH(aryl), —S(O)₂NH₂, —S(O)₂NHR²⁸, —S(O)₂NH(aryl), —S(O)₂NH(heterocycloalkyl), —S(O)₂N(alkyl)₂, —S(O)₂N(alkyl)(aryl), —OH, —OR²⁹, —O-heterocycloalkyl, —O-cycloalkylalkyl, —O-heterocycloalkylalkyl, —NH₂, —NHR²⁹, —N(alkyl)₂, —N(arylalkyl)₂, —N(arylalkyl)(heteroarylalkyl), —NHC(O)R²⁹, —NHC(O)NH₂, —NHC(O)NH(alkyl), —NHC(O)N(alkyl)(alkyl), —N(alkyl)C(O)NH(alkyl), —N(alkyl)C(O)N(alkyl)(alkyl), —NHS(O)₂R²⁹, —NHS(O)₂NH(alkyl), —NHS(O)₂N(alkyl)(alkyl), —N(alkyl)S(O)₂NH(alkyl) and —N(alkyl)S(O)₂N(alkyl)(alkyl);

R²⁸ is alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl or heterocycloalkenylheteroaryl;

R²⁹ is alkyl, arylalkyl, heteroarylalkyl, cycloalkylalkyl, heterocycloalkylalkyl, arylcycloalkylalkyl, heteroarylcycloalkylalkyl, aryl heterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl or heterocycloalkenylheteroaryl, wherein:

"heteroaryl" means a moiety selected from pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, and benzothiazolyl;

"heterocyclyl" (or "heterocycloalkyl") means a moiety selected from piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, and tetrahydrothiopyranyl; and "heterocyclenyl" (or "hetocyloalkenyl") means a heterocyclyl moiety as defined above which contains at least one carbon-carbon double bond and/or at least one carbon-nitrogen double bond.

9. A compound of claim 8, wherein:
R²¹ is

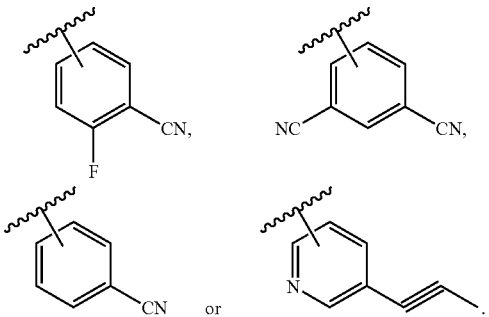

10. A compound of claim 8, wherein:
R⁶ is

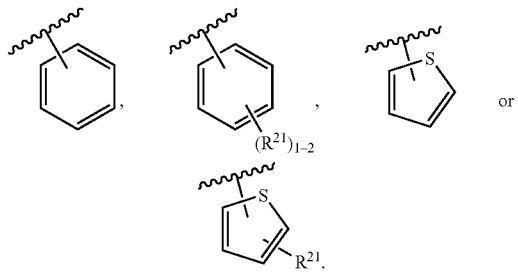

11. A compound of claim 8, wherein:
R⁶ is aryl.

12. A compound of claim 8, wherein:
R⁶ is (R²¹)₁₋₅-aryl.

13. A compound of claim 12, wherein:
R²¹ is —CN, halo, aryl, (R²²)-aryl, heteroaryl, or (R²²)₁₋₂-heteroaryl.

14. A compound of claim 13, wherein:
R²² is —CN, halo or alkyne.

15. A compound of claim 14, wherein:
R²² is F or

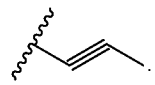

16. A compound of claim 13, wherein:
R²¹ is halo.

17. A compound of claim 8, wherein:
R⁶ is

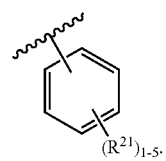

18. A compound of claim 8, wherein:

$R^6$ is

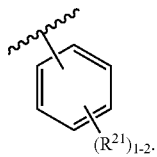

19. A compound of claim 18, wherein:

$R^{21}$ is —CN, halo, aryl, $(R^{22})$-aryl, heteroaryl, or $(R^{22})_{1-2}$-heteroaryl.

20. A compound of claim 19, wherein:

$R^{21}$ is halo.

21. A compound of claim 8, wherein:

$R^6$ is selected from the group consisting of thiophenyl and $(R^{21})_{1-3}$-thiophenyl.

22. A compound of claim 8, wherein:

$R^6$ is

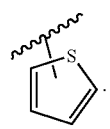

23. A compound of claim 8, wherein:

$R^6$ is $(R^{21})_{1-3}$-thiophenyl.

24. A compound of claim 23, wherein:

$R^{21}$ is —CN, halo, aryl, $(R^{22})$-aryl, heteroaryl, or $(R^{22})_{1-2}$-heteroaryl.

25. A compound of claim 24, wherein:

$R^{21}$ is halo.

26. A compound of claim 8, wherein:

$R^6$ is

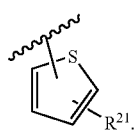

27. A compound of claim 26, wherein:

$R^{21}$ is —CN, halo, aryl, $(R^{22})$-aryl, heteroaryl, or $(R^{22})_{1-2}$-heteroaryl.

28. A compound of claim 27, wherein:

$R^{21}$ is halo.

29. A compound of claim 8, wherein:

$R^5$ is selected from the group consisting of arylalkyl, aryl, heteroaryl, —C(=NR$^{11}$)R$^8$, —C(O)R$^8$, C(O)OR$^9$, aryl-R$^{21}$ and heteroaryl-R$^{21}$.

30. A compound of claim 29, wherein $R^5$ is

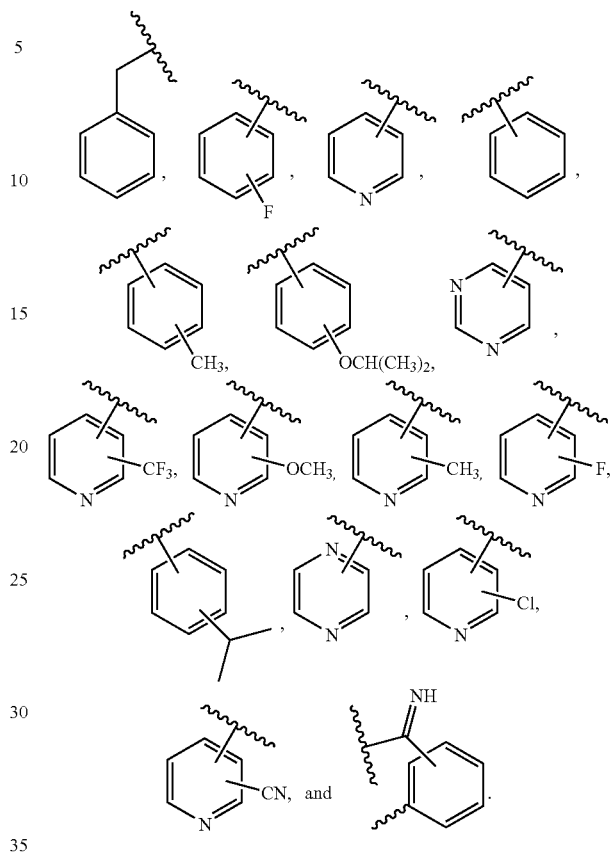

31. A compound of claim 29, wherein $R^8$ and $R^9$ are independently selected from the group consisting of: alkyl, cycloalkyl, aryl, arylalkyl, heteroaryl, $R^{18}$-alkyl, $R^{18}$-aryl, and $R^{18}$-heteroaryl.

32. A compound of claim 30, wherein $R^8$ and $R^9$ are independently selected from the group consisting of:

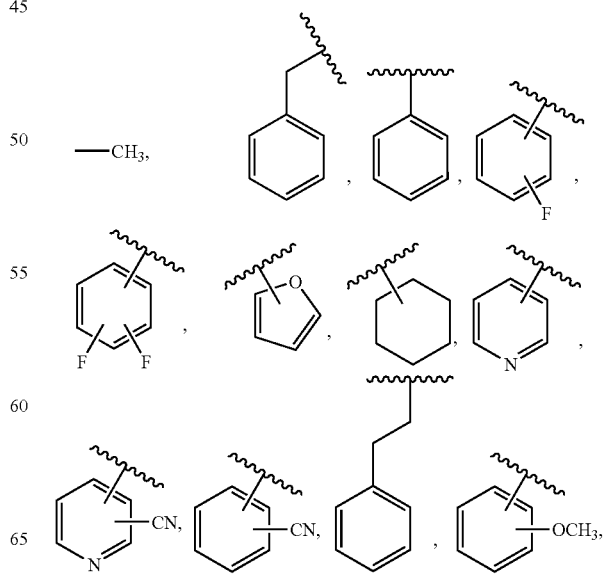

-continued

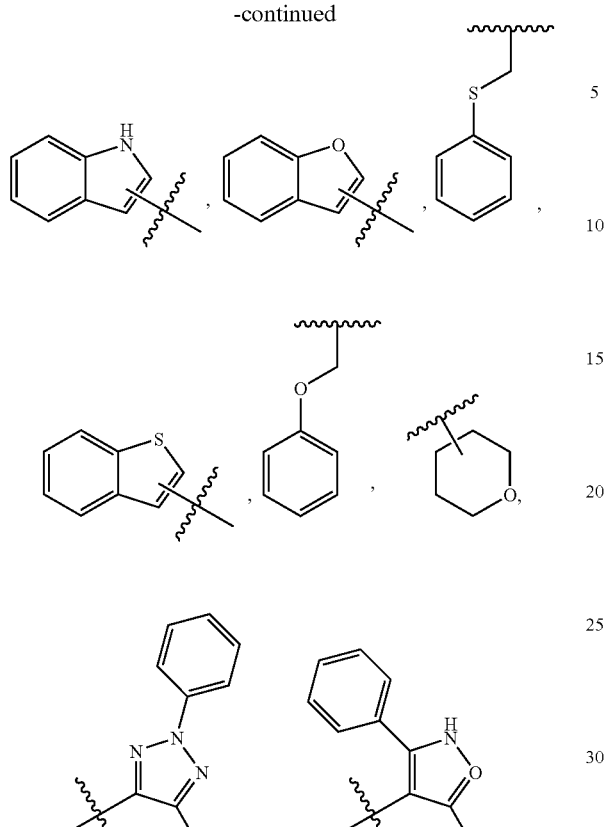

33. A compound of claim 31, wherein $R^{18}$ is 1-5 substituents independently selected from the group consisting of alkyl, halo, —$CF_3$, —CN, —$SR^{19}$ and —$OR^{20}$.

34. A compound of claim 31, wherein $R^{18}$ is 1-5 substituents independently selected from the group consisting of halo, —CN, —$OCH(CH_3)_2$, —$OCH_3$, —$CH_3$,

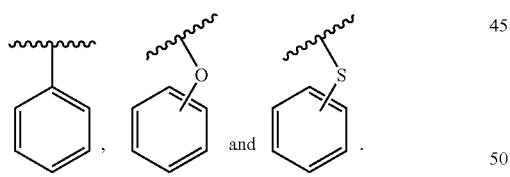

35. A compound of claim 29, wherein $R^5$ is aryl-$R^{21}$.

36. A compound of claim 35, wherein $R^{21}$ is 1-5 substituents independently selected from the group consisting of halo, —$OCH(CH_3)_2$, —$CH_3$, —$CF_3$, —$OCH_3$, —$CH(CH_3)_2$ and —CN.

37. A compound of claim 29, wherein $R^5$ is heteroaryl-$R^{21}$.

38. A compound of claim 37, wherein $R^{21}$ is 1-5 substituents independently selected from the group consisting of halo, —$OCH(CH_3)_2$, —$CH_3$, —$CF_3$, —$OCH_3$, —$CH(CH_3)_2$ and —CN.

39. A compound, or a stereoisomer, tautomer, or pharmaceutically acceptable salt of said compound, said stereoisomer, or said tautomer, selected from the group consisting of:

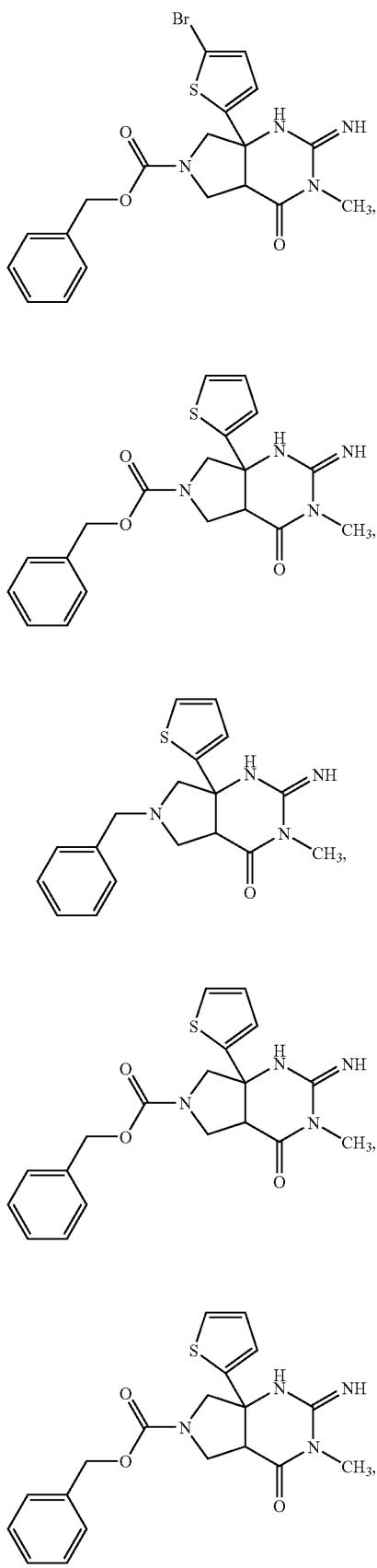

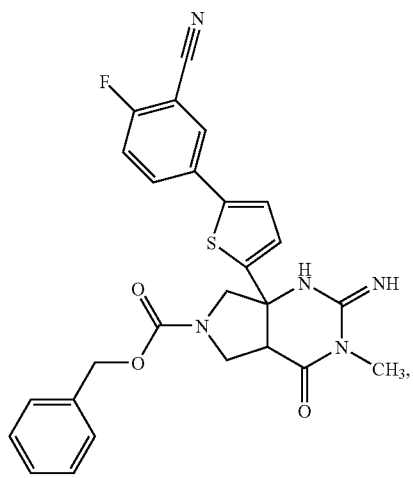
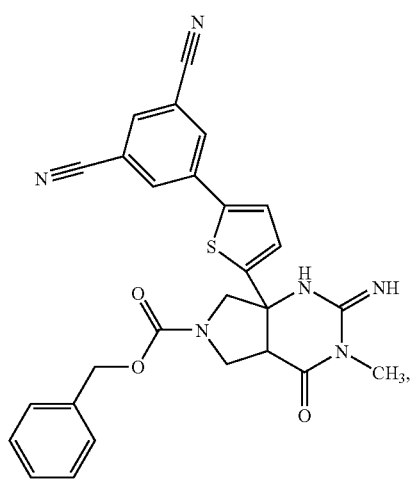
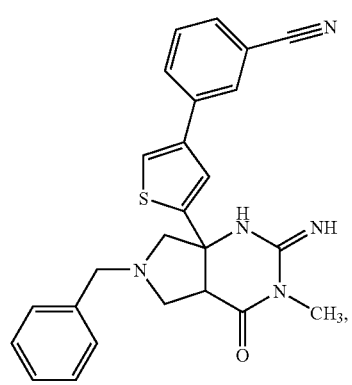
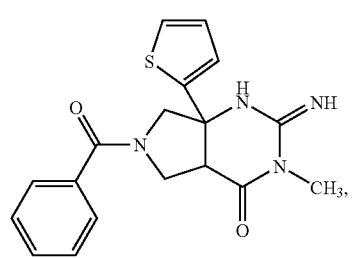
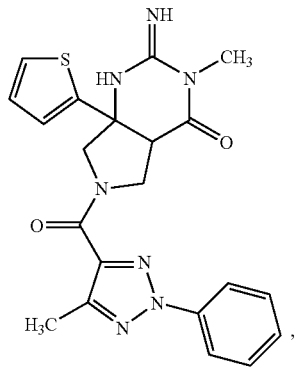
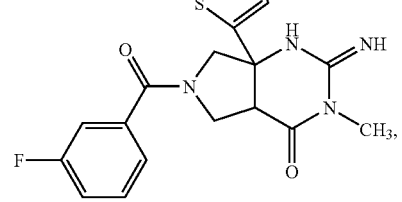
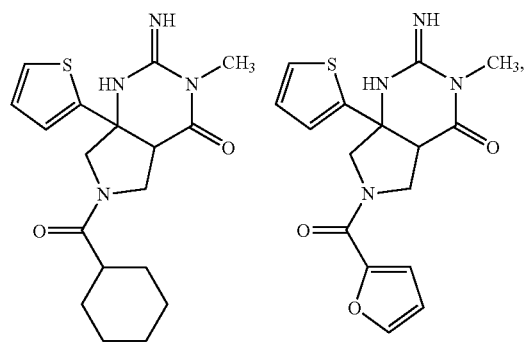
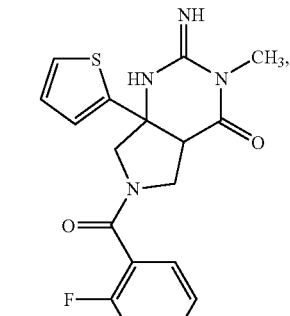
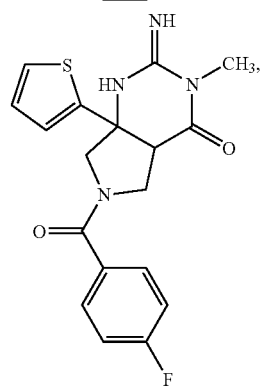

111
-continued
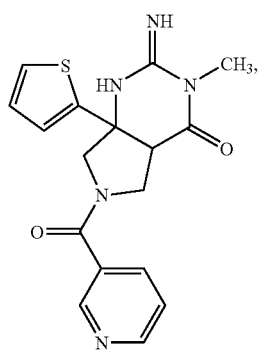
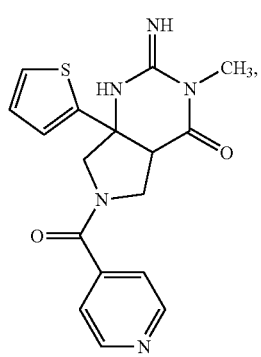
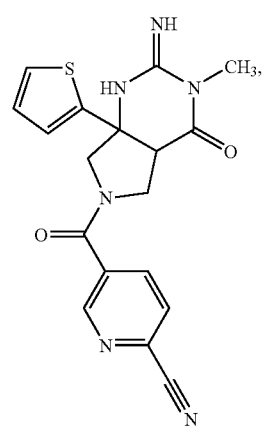
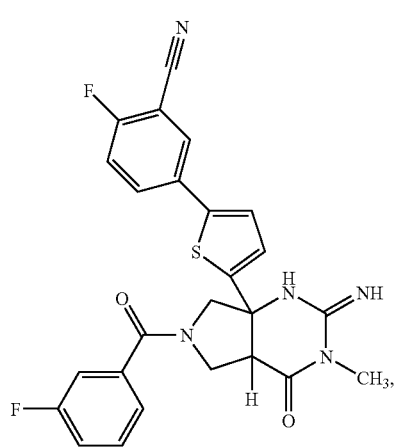
112
-continued
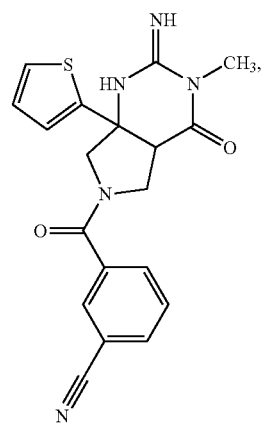
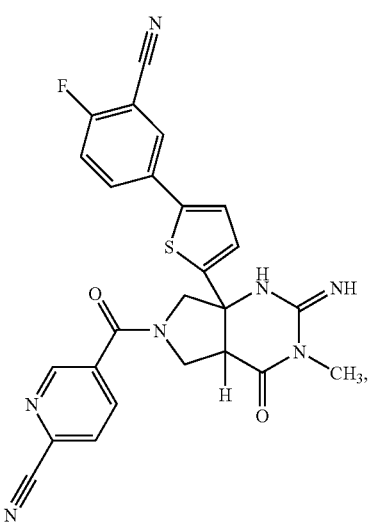
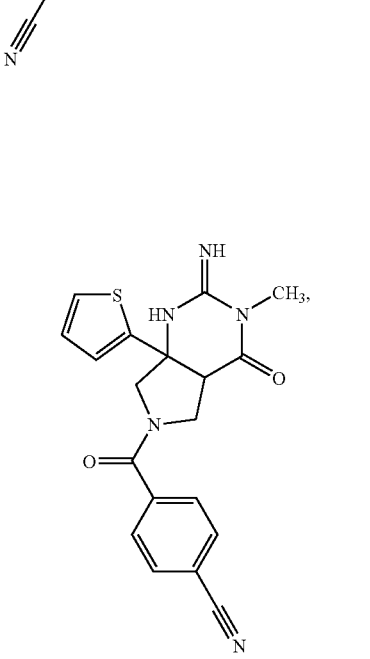

-continued
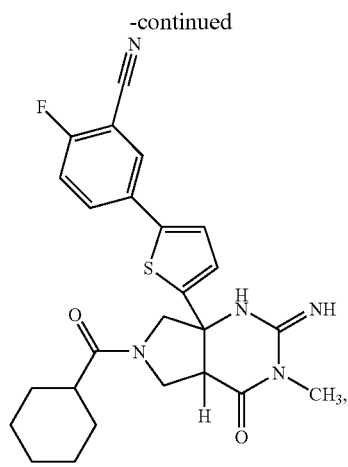
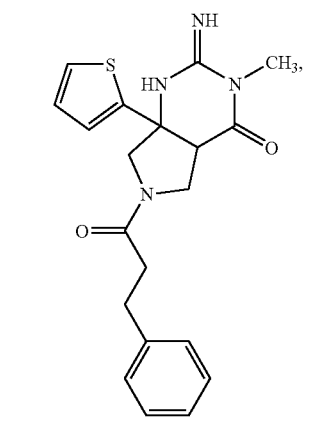
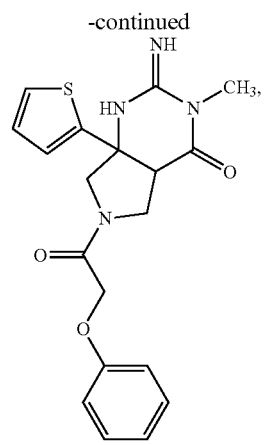
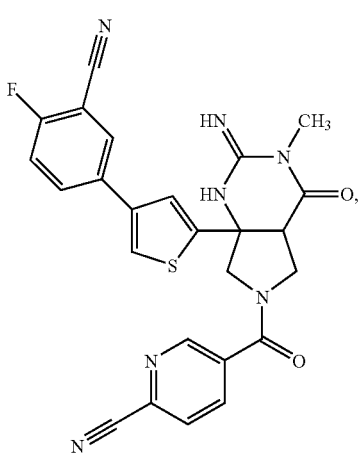
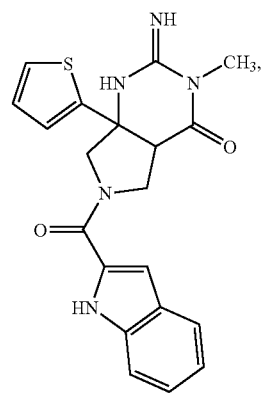
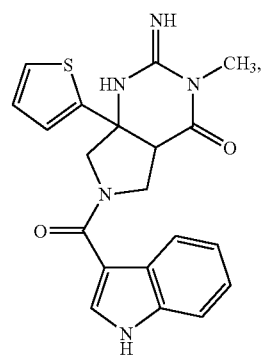

-continued
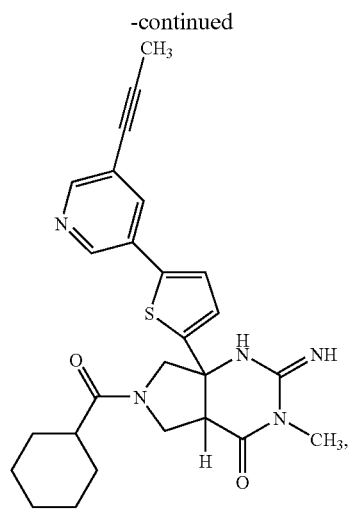
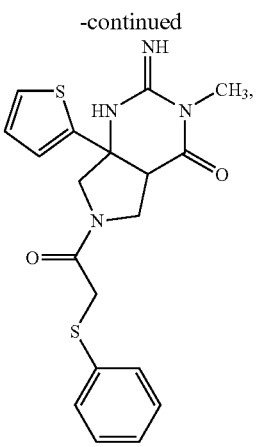
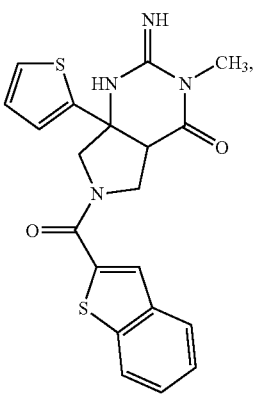
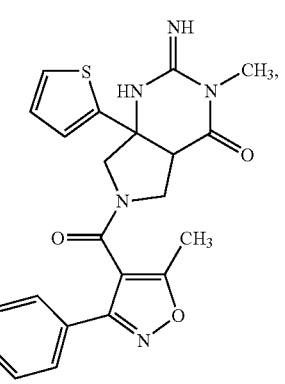
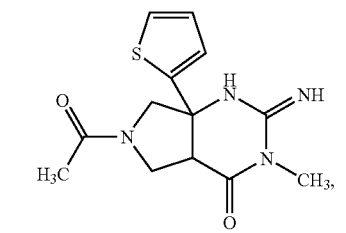
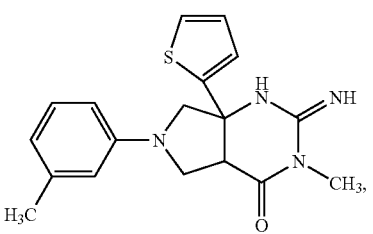

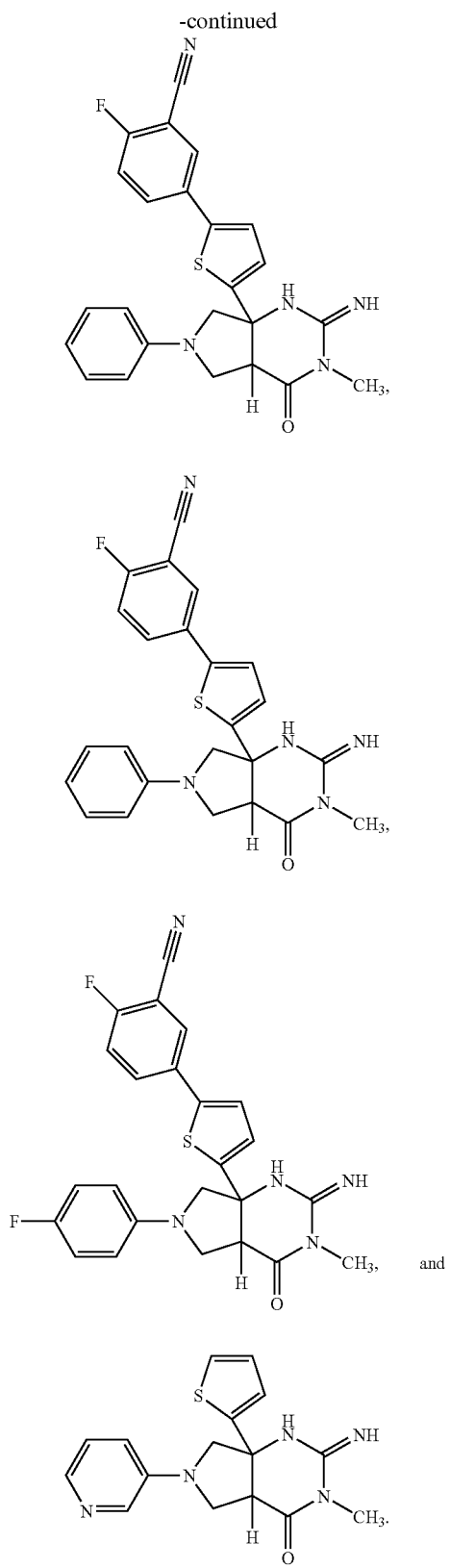
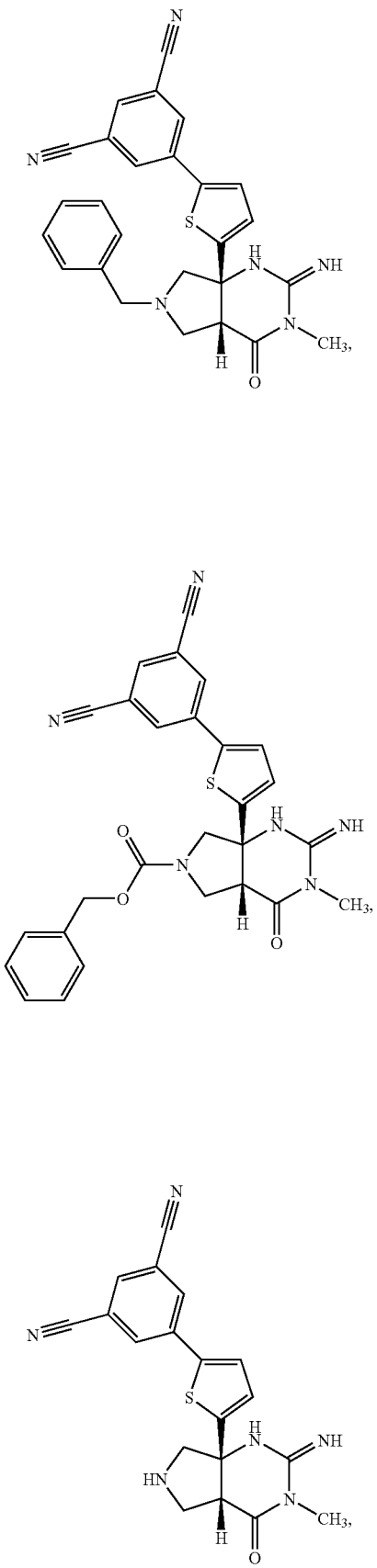
40. A compound, or a stereoisomer, tautomer, or pharmaceutically acceptable salt of said compound, said stereoisomer, or said tautomer, selected from the group consisting of:

119
-continued
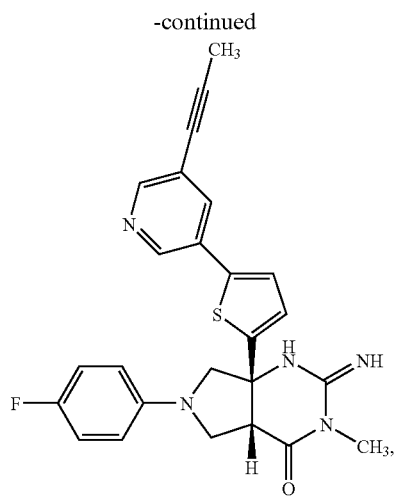
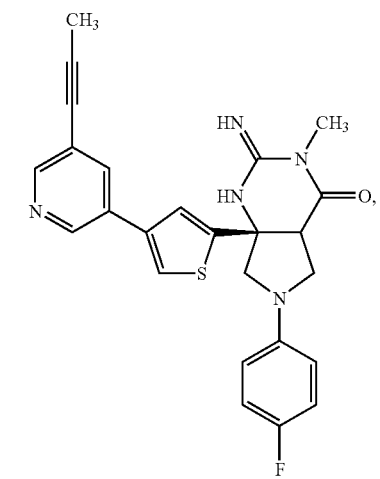
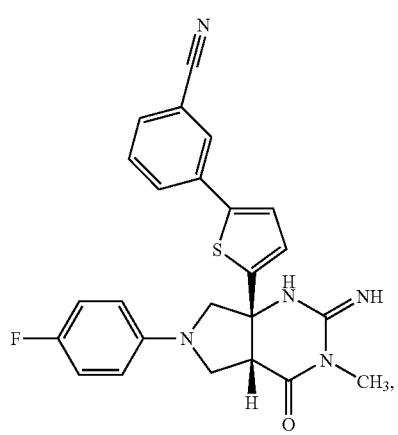
120
-continued
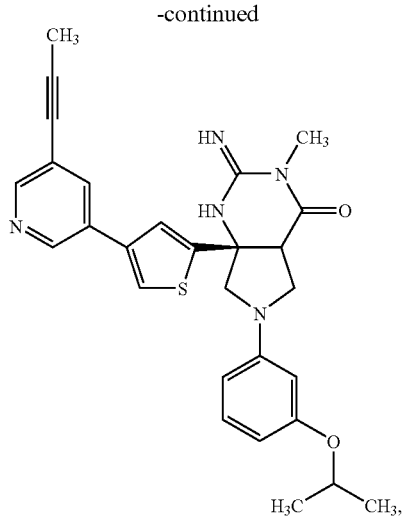
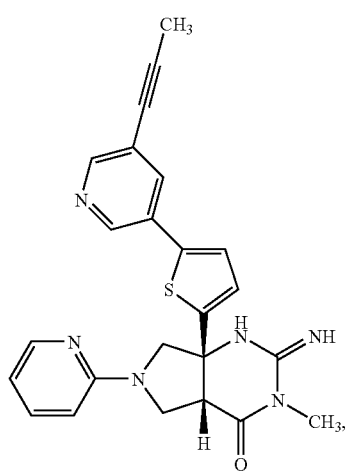
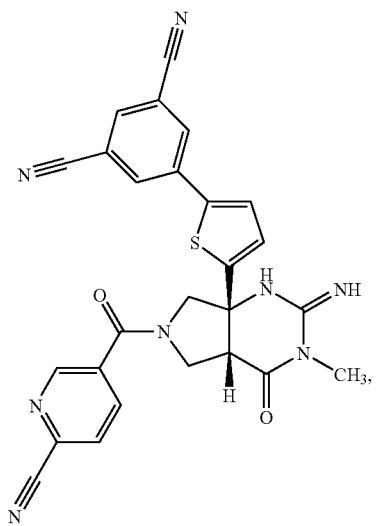

-continued
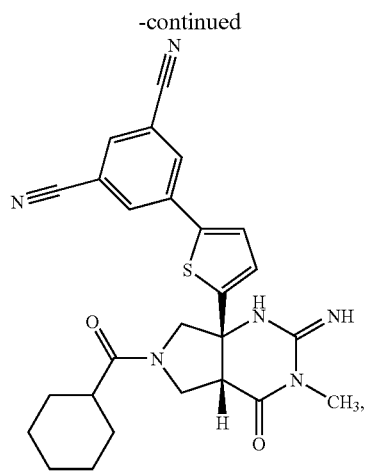
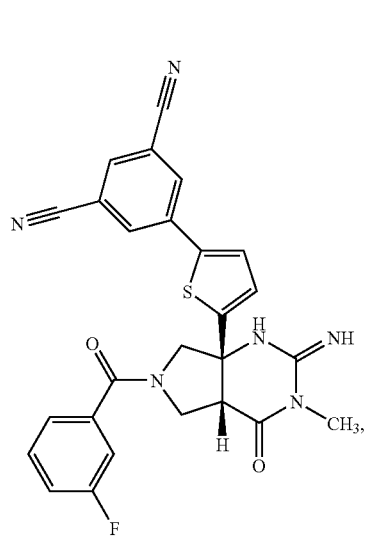
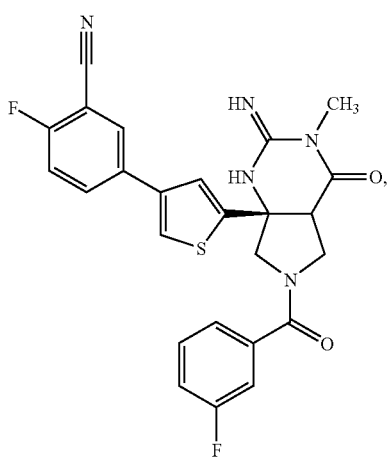
-continued
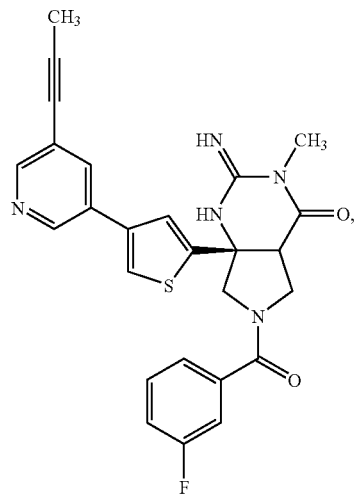
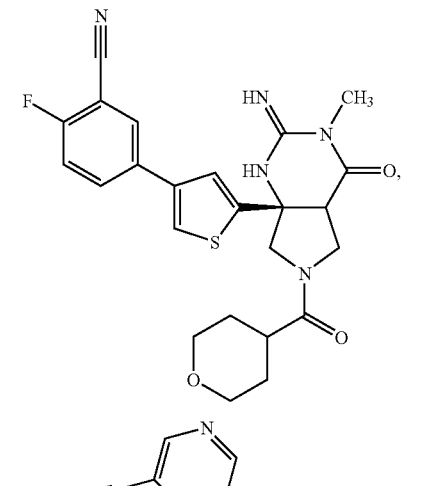
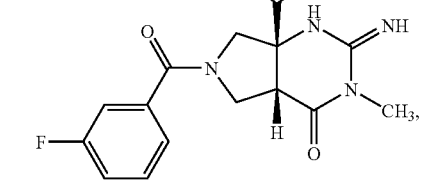
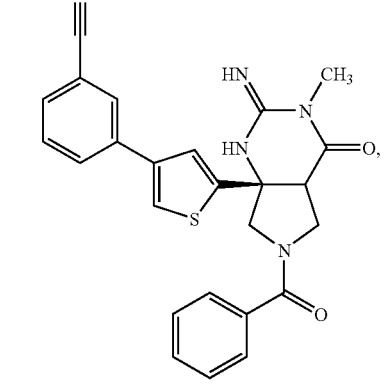

123
-continued
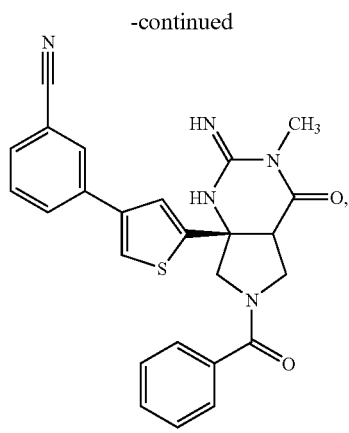
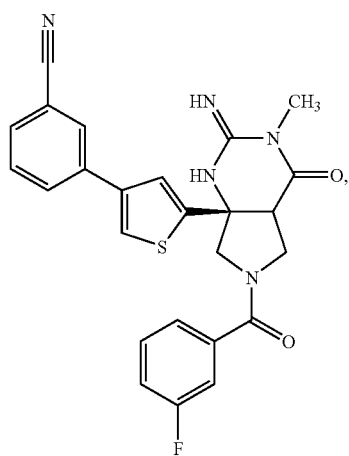
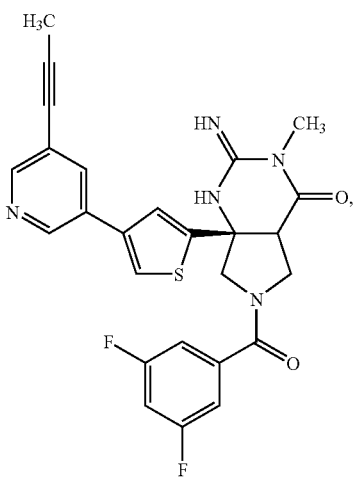
124
-continued
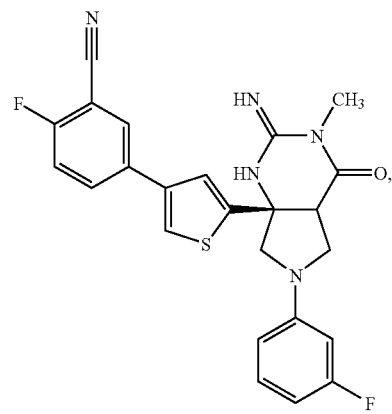
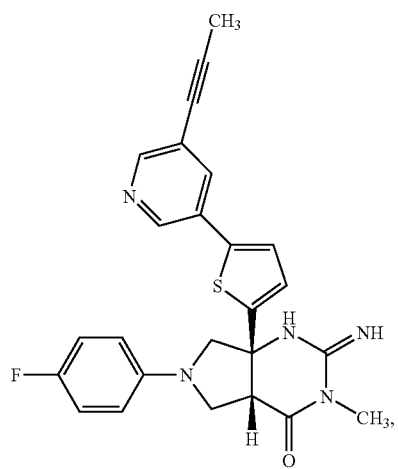
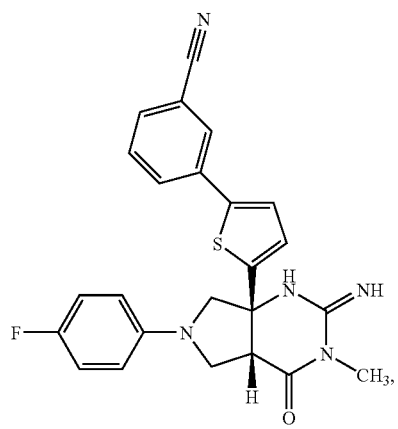

125
-continued
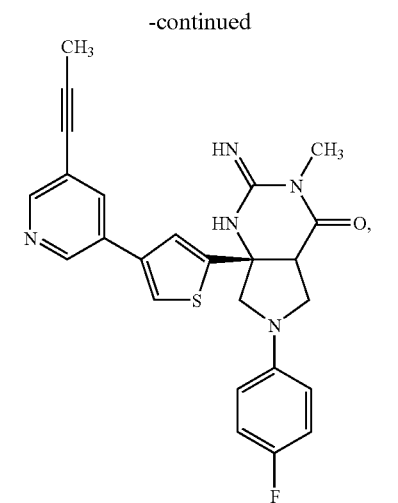
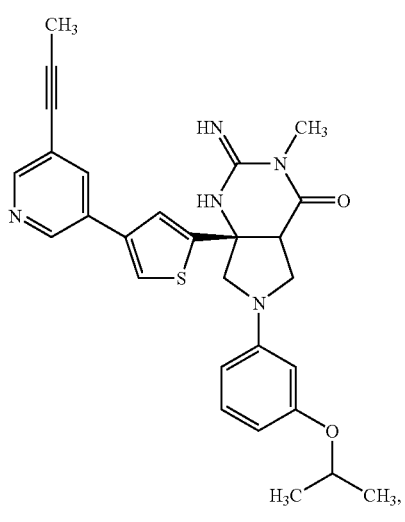
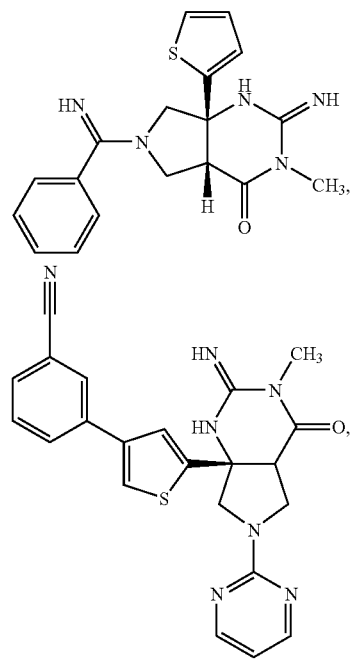
126
-continued
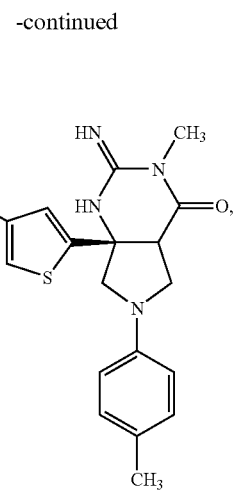
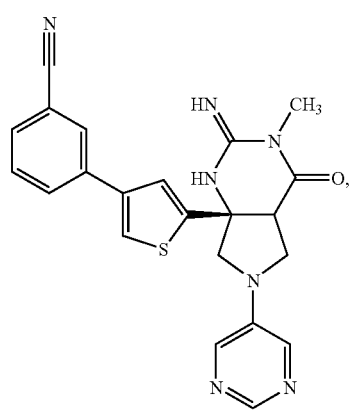
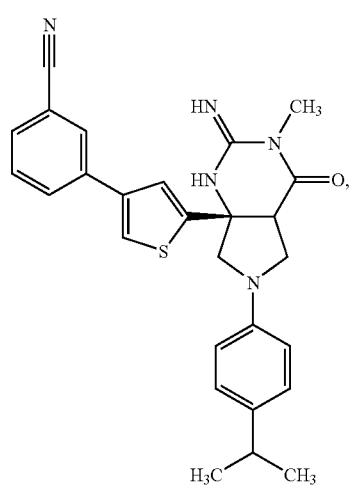

127
-continued
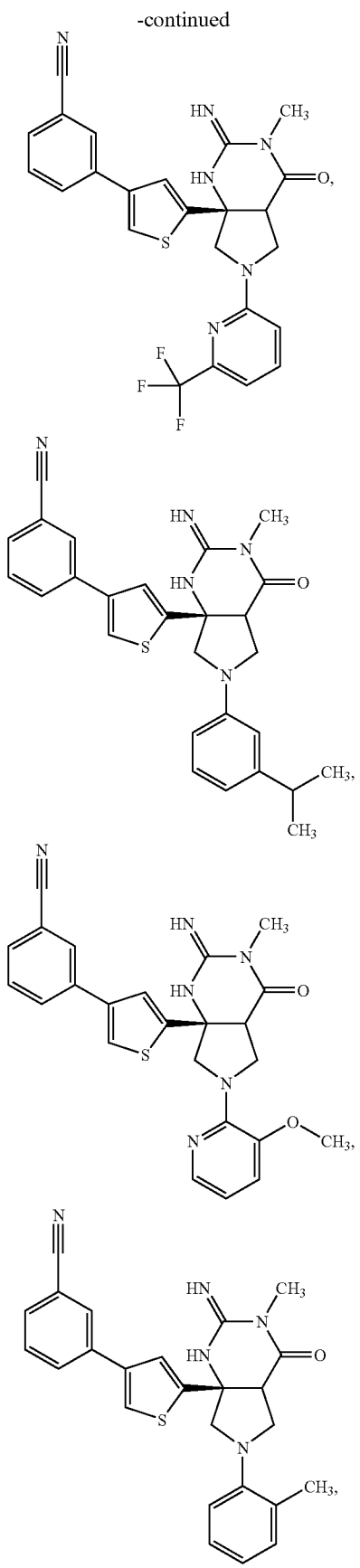
128
-continued
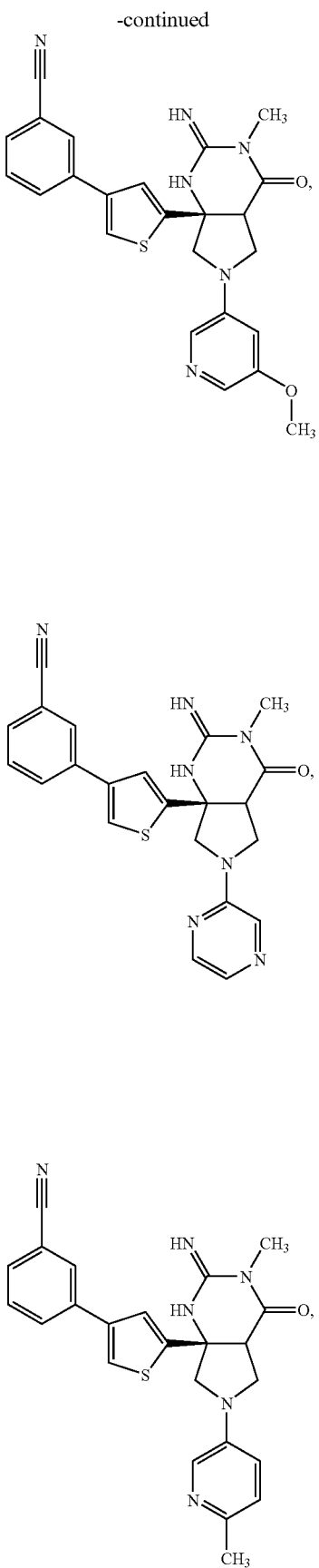

-continued
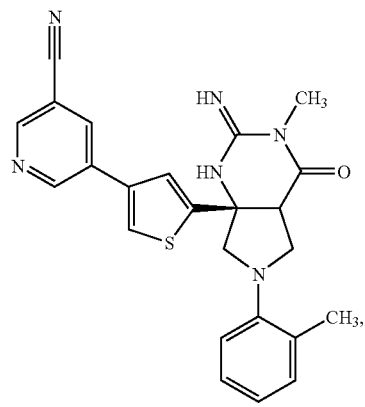
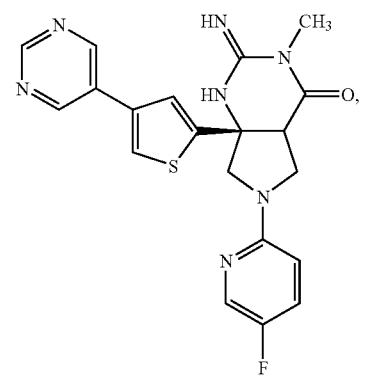
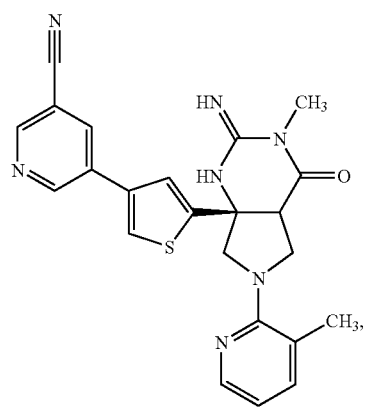
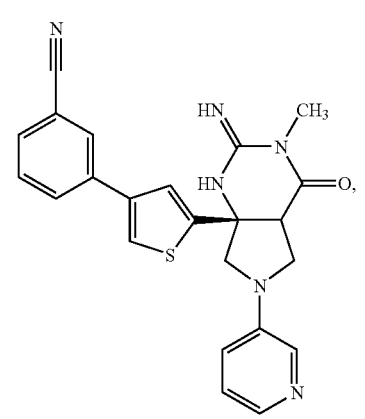
-continued
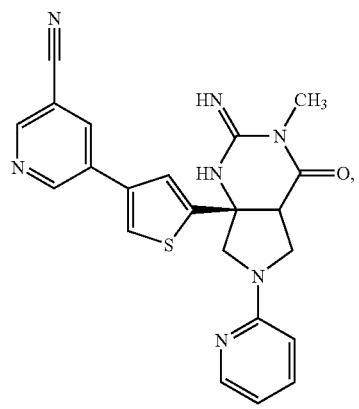
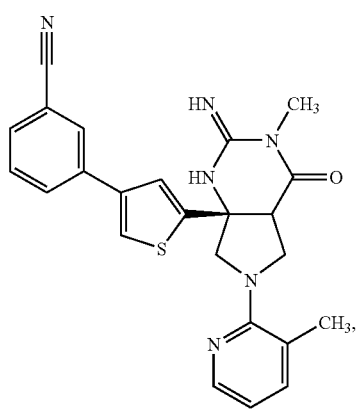
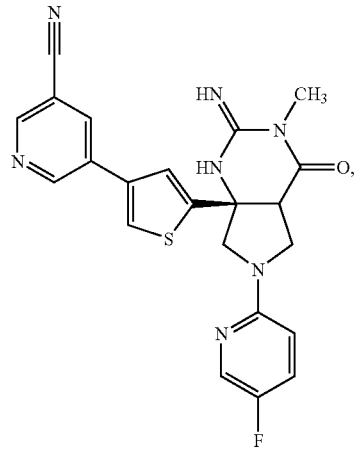

-continued
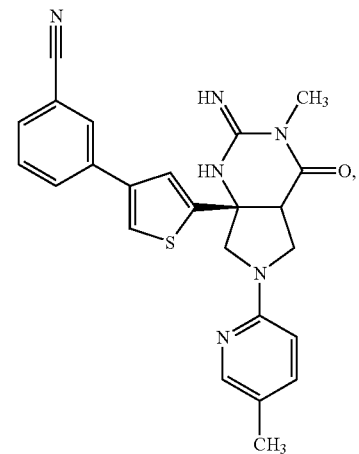
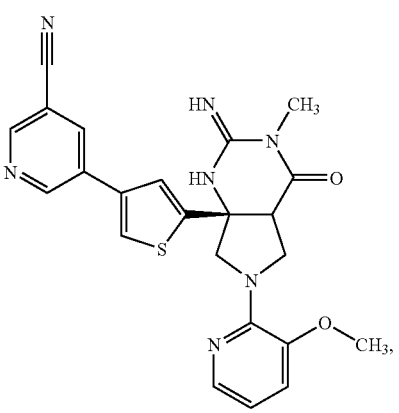
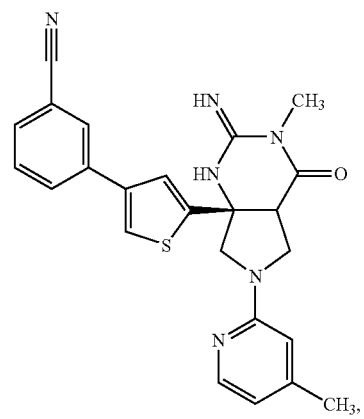
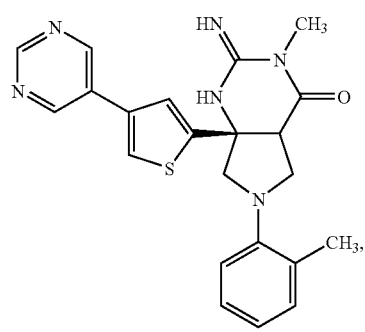
-continued
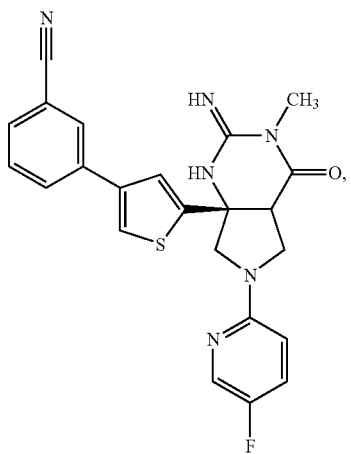
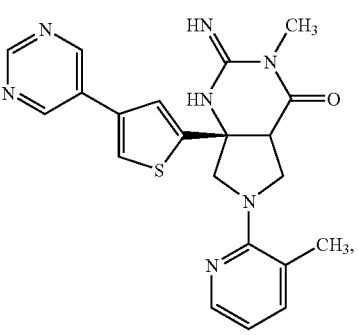
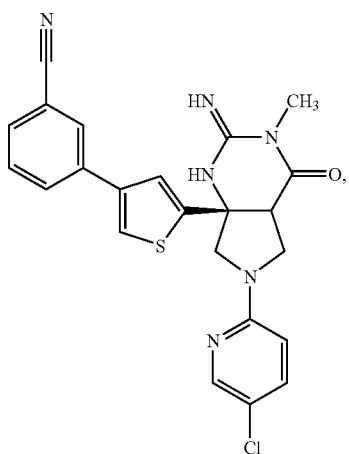
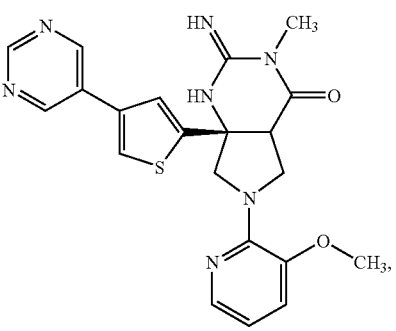

-continued

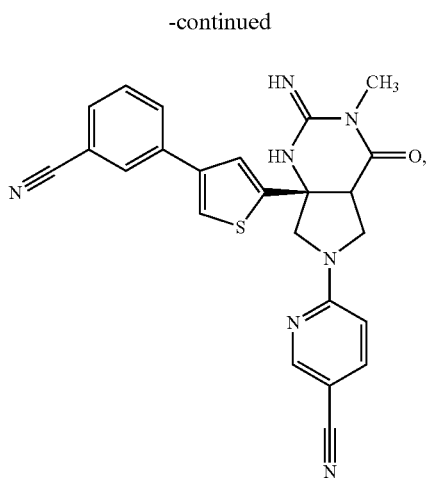

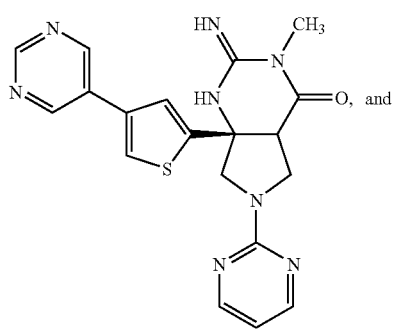

-continued

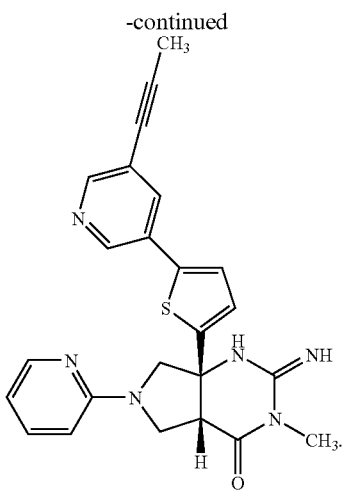

41. A pharmaceutical composition comprising at least one compound of claim 1 and a pharmaceutically effective carrier.

42. A pharmaceutical composition comprising at least one compound of claim 8 and a pharmaceutically effective carrier.

43. A pharmaceutical composition comprising at least one compound of claim 29 and a pharmaceutically effective carrier.

44. A pharmaceutical composition comprising at least one compound of claim 39 and a pharmaceutically effective carrier.

45. A pharmaceutical composition comprising at least one compound of claim 40 and a pharmaceutically effective carrier.

\* \* \* \* \*

SEQUENCE LISTING

```
<160> NUMBER OF SEQ ID NOS: 2

<210> SEQ ID NO 1
<211> LENGTH: 19
<212> TYPE: PRT
<213> ORGANISM: Artificial Sequence
<220> FEATURE:
<223> OTHER INFORMATION: EuK-biotin labeled APPsw substrate
<220> FEATURE:
<221> NAME/KEY: MISC_FEATURE
<222> LOCATION: (1)..(1)
<223> OTHER INFORMATION: -EuK labeled residue
<220> FEATURE:
<221> NAME/KEY: MISC_FEATURE
<222> LOCATION: (19)..(19)
<223> OTHER INFORMATION: -biotinylated residue

<400> SEQUENCE: 1

Lys Thr Glu Glu Ile Ser Glu Val Asn Leu Asp Ala Glu Phe Arg His
1               5                   10                  15

Asp Lys Cys

<210> SEQ ID NO 2
<211> LENGTH: 18
<212> TYPE: PRT
<213> ORGANISM: Artificial Sequence
<220> FEATURE:
<223> OTHER INFORMATION: unlabeled APPsw peptide

<400> SEQUENCE: 2

Lys Thr Glu Glu Ile Ser Glu Val Asn Leu Asp Ala Glu Phe Arg His
1               5                   10                  15

Asp Lys
```